US011458168B2

(12) United States Patent
Metelitsa et al.

(10) Patent No.: US 11,458,168 B2
(45) Date of Patent: Oct. 4, 2022

(54) NKT-CELL SUBSET FOR IN VIVO PERSISTENCE AND THERAPEUTIC ACTIVITY AND PROPAGATION OF SAME

(71) Applicant: Baylor College of Medicine, Houston, TX (US)

(72) Inventors: Leonid S. Metelitsa, Sugar Land, TX (US); Amy N. Courtney, Houston, TX (US); Gengwen Tian, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 15/987,724

(22) Filed: May 23, 2018

(65) Prior Publication Data

US 2018/0264040 A1    Sep. 20, 2018

Related U.S. Application Data

(63) Continuation of application No. 15/135,453, filed on Apr. 21, 2016.

(60) Provisional application No. 62/309,525, filed on Mar. 17, 2016, provisional application No. 62/151,690, filed on Apr. 23, 2015.

(51) Int. Cl.
| | |
|---|---|
| *A61K 35/17* | (2015.01) |
| *C07K 16/28* | (2006.01) |
| *C12N 5/0783* | (2010.01) |
| *A61K 38/17* | (2006.01) |
| *A61P 35/00* | (2006.01) |
| *C07K 16/30* | (2006.01) |
| *A61K 39/00* | (2006.01) |
| *C12N 5/10* | (2006.01) |
| *A61K 35/12* | (2015.01) |
| *A61P 37/00* | (2006.01) |

(52) U.S. Cl.
CPC ............ *A61K 35/17* (2013.01); *A61K 38/178* (2013.01); *A61K 39/0011* (2013.01); *A61P 35/00* (2018.01); *C07K 16/2803* (2013.01); *C07K 16/3084* (2013.01); *C12N 5/0646* (2013.01); *C12N 5/10* (2013.01); *A61K 2035/124* (2013.01); *A61K 2039/5156* (2013.01); *A61P 37/00* (2018.01); *C12N 2501/599* (2013.01); *C12N 2510/00* (2013.01)

(58) Field of Classification Search
CPC .. A61K 35/17; A61K 38/178; A61K 39/0011; A61K 2035/124; A61K 2039/5156; A61P 35/00; A61P 37/00; C07K 16/2803; C07K 16/3084; C12N 5/0646; C12N 5/10; C12N 2501/599; C12N 2510/00
USPC .............. 424/93.21; 435/325, 373, 386, 455
See application file for complete search history.

(56) References Cited

U.S. PATENT DOCUMENTS

| | | |
|---|---|---|
| 9,487,800 B2 | 11/2016 | Schonfeld et al. |
| 10,040,846 B2 | 8/2018 | Frigault et al. |
| 2008/0050341 A1 | 2/2008 | Morgan et al. |
| 2011/0286980 A1 | 11/2011 | Brenner |
| 2013/0001376 A1 | 1/2013 | Peled et al. |
| 2013/0011376 A1 | 1/2013 | Peled et al. |
| 2013/0309213 A1 | 11/2013 | Manjili et al. |
| 2014/0255363 A1 | 9/2014 | Metelitsa et al. |
| 2014/0322216 A1 | 10/2014 | Kaplan |
| 2015/0086584 A1 | 3/2015 | Gilboa et al. |
| 2017/0183407 A1 | 6/2017 | Cooper et al. |

FOREIGN PATENT DOCUMENTS

| | | |
|---|---|---|
| CN | 102781449 A | 1/2012 |
| CN | 104159909 A | 11/2014 |
| WO | WO 94/20627 A1 | 9/1994 |
| WO | WO 2014/138315 A1 | 9/2014 |
| WO | 2015/051247 A1 | 4/2015 |
| WO | WO 2015/051247 * | 4/2015 |

OTHER PUBLICATIONS

Harada et al. (2005) J. Immunother., vol. 28(4),314-321.*
Heczey et al. (2014) Blood, vol. 124(18), 2824-2833.*
Sun et al. (2012) J. Interferon & Cytokine Res., vol. 32 (11), 505-516.*
Coquet et al. (2007) J. Immunol., vol. 178, 2827-2834.*
Rogers et al. (2004) J. Immunol. Methods, vol. 285, 197-214.*
Tangye et al. (2015) Curr. Opin. Immunol., vol. 34, 107-115, available online Mar. 23, 2015, http://dx.doi.org/10.1016/j.coi.2015.02.010.*
Tian et al. (2013) J. Immunol., vol. 190 (1 Supplement) 45.3, 1 page meeting abstract.*
Exley et al. (2010) Curr. Protoc. Immunol., 90:14.11.1-14.11.17, pp. 1-17.*
Yang et al. (2003) J. Immunol., vol. 171, 5913-5920.*
Li et al. (2015) Immunobiology, vol. 220, 876-888, published online Jan. 31, 2015.*
Kalas M, June CH. "Adoptive T cell transfer for cancer immunotherapy in the era of synthetic biology," Immunity 2013;39(1):49-60.
Sommermeyer D, et al. "Chimeric antigen receptor-modified T cells derived from defined COB and CD4 subsets confer superior anti-tumor reactivity in vivo," Leukemia 2015.
Wang X, et al. "Phenotypic and functional attributes oflentivims-modified CD19-specific human COB+central memory T cells manufactured at clinical scale," J Immunother. 2012;35(9):689-701.

(Continued)

*Primary Examiner* — Anne Marie S Wehbe
(74) *Attorney, Agent, or Firm* — Arnold & Porter Kaye Scholer

(57) ABSTRACT

Embodiments of the disclosure include methods and compositions for producing NKT cells effective for immunotherapy and also methods and compositions for providing an effective amount of NKT cells to an individual in need of immunotherapy. In specific embodiments, the NKT cells are CD62L+ and have been exposed to one or more costimulatory agents to maintain CD62L expression. The NKT cells may be modified to incorporate a chimeric antigen receptor, in some cases.

35 Claims, 34 Drawing Sheets

(56) References Cited

OTHER PUBLICATIONS

Coquet et al., "IL-21 Modulates Activation of NKT Cells in Patients with Stage IV Malignant Melanoma." Clinical & Translational Immunology, 2(10), p. e6. (2013).

Coquet, "IL-21 Is Produced by NKT Cells and Modulates NKT Cell Activation and Cytokine Production." The Journal of Immunology, 178(5), pp. 2827-2834. (2007).

Singh et al. "Reprogramming CD 19-Specific T Cells with IL-21 Signaling Can ImproveCIO Adoptive Immunotherapy ofB-Lineage Malignancies." Cancer Research, 71(10), pp. 3516-3527. (2011).

Werner et al. (2011) BMC Immunology, vol. 12:26, pp. 1-11.

Yang et al., J. Immunol (2003), "Control of NKT Cell Differentiation by Tissue-Specific Microenvironments", vol. 171, pp. 5913-5920.

Chan et al,. Clinical and Experimental Immunololgy, Ex-Vivo Analysis of human Natural Killer T cells demonstrates heterogeneity between tissues and within established CD4+ and CD4-subsets, vol. 172, pp. 129-137.

Redmond, W. L. et al., "The role of OX40-mediated co-stimulation in T-cell activation and survival", Crit Rev. Immunol., 2009; 29(3):187-201.

Sallusto, F. et al., "Central memory and effector memory T cell subsets: function, generation, and maintenance", Annu. Rev. Immunol., 2004; 22:745-763.

Savage, A. K. et al. "The transcription factor PLZF directs the effector program of the NKT cell lineage", Immunity, 2008; 29(3):391-403.

Savoldo, B. et al., "CD2S costimulation improves expansion and persistence of chimeric antigen receptor-modified T cells in lymphoma patients", J. C/in. Invest., 2011; 121(5):1S22-1S26.

Sommermeyer, D. et al., "Chimeric antigen receptor-modified T cells derived from defined COB and CD4 subsets confer superior antitumor reactivity in vivo", Leukemia, 2015; 30(2): 492-500.

Suhoski, M. M. et al., "Engineering artificial antigen-presenting cells to express a diverse array of co-stimulatory molecules", Mol. Ther., 2007; 15(5):981-988.

Tachibana, T. et al., "Increased intratumor Valpha24-positive natural killer T cells: a prognostic factor for primary colorectal carcinomas", Clin. Cancer Res., 2005; 11(20):7322-7327.

Tahir, S. M. et al., "Loss of IFN-gamma production by invariant NKT cells in advanced cancer", J. Immunol., 2001; 167(7):4046-4050.

Taniguchi, M. et al., "Discovery of NKT cells and development of NKT cell-targeted anti-tumor immunotherapy", Proc. Jpn. Acad. Ser. B Phys. Bio/.Sci., 2015; 91(7):292-304.

Torikai, H. et al., "Toward eliminating HLA class I expression to generate universal cells from allogeneic donors" Blood, 2013; 122(8):1341-1349.

Uldrich, A. P. et al., "NKT cell stimulation with glycolipid antigen in vivo: costimulation-dependent expansion, Bim-dependent contraction, and hyporesponsiveness to further antigenic challenge", J. Immunol., 2005; 175(5):3092-3101.

Van Den Heuvel, M. J. et al., "NKT cell costimulation: experimental progress and therapeutic promise", Trends Mo/.Med., 2011; 17(2):65-77.

Vera, J. et al., "T lymphocytes redirected against the kappa light chain of human immunoglobulin efficiently kill mature B lymphocyte-derived malignant cells", Blood, 2006; 108(12):3890-3897.

Vivier, E. et al., Targeting natural killer cells and natural killer Tcells in cancer. Nat. Rev. Immunol. 2012; 12(4):239-252.

Wang, X. et al., "Phenotypic and functional attributes of lentivirus-modified CD19-specific human COB+central memory T cells manufactured at clinical scale", J. Immunother., 2012; 35(9):689-701.

Xu Y. et al., "Closely related T-memory stem cells correlate with in vivo expansion of CAR.CD19-T cells and are preserved by IL-7 and IL-15", Blood, 2014; 123(24):3750-3759.

Acuto, O et al., "CD28-mediated co-stimulation: a quantitative support for TCR signaling", Nat. Rev. Immunol. 2003; 3(12):939-951.

McEwen-Smith, R. M. et al., "The regulatory role of invariant NKT cells in tumor immunity", Cancer Immunoi. Res., 2015; 3(5):425-435.

Ara, T. et al., "Critical role of STAT3 in IL-6-mediated drug resistance in human neuroblastoma", Cancer Res., 2013; 73(13), pp. 3852-3864.

Baev, D. V. et al., "Distinct homeostatic requirements of CD4+ and CD4-subsets of Valpha24-invariant natural killer T cells in humans", Blood, 2004; 104(13):4150-4156.

Barakonyi, A. et al., "Cutting edge: engagement of CD160 by its HLA-C physiological ligand triggers a unique cytokine profile secretion in the cytotoxic peripheral blood NK cell subset", J. Immunol., 2004; 173(9):5349-5354.

Metelitsa, L. S. et al., "Human NKT cells mediate antitumor cytotoxicity directly by recognizing target cell CD1d with bound ligand or indirectly by producing IL-2 to activate NK cells", J. Immunol., 2001; 167(6):3114-3122.

Brentjens, R. J. et al., "CD19-targeted T cells rapidly induce molecular remissions in adults with chemotherapy-refractory acute lymphoblastic leukemia", Sci. Transi. Med., 2013; 5(177):177ra38, 19 pages.

Cariani, E. et al., "Immunological and molecular correlates of disease recurrence after liver resection for hepatocellular carcinoma", PLoS. One. 2012; 7(3):e32493, 8 pages.

Carr, T. et al., "The transcription factor lymphoid enhancer factor 1 controls invariant natural killer T cell expansion and Th2-type effector differentiation", J. Exp. Med., 2015; 212(5):793-807.

Casorati, G. et al., "Invariant natural killer T cells reconstitution and the control of leukemia relapse in pediatric haploidentical hematopoietic stem cell transplantation", Oncoimmunology, 2012; 1(3):355-357.

Chan, W. K. et al., "Chimeric antigen receptor-redirected CD45RA-negative T cells have potent antileukemia and pathogen memory response without graft-versus-host activity", Leukemia, 2015; 29(2):387-395.

Cohen, N. R. et al., "Shared and distinct transcriptional programs underlie the hybrid nature of iNKT cells", Nat. Immunol., 2013; 14(1):90-99.

Constantinides, M. G. et al., "Transcriptional regulation of the NKT cell lineage", Curr. Opin. Immunol., 2013; 25(2):161-167.

Constantinides, M. G. et al., "A naive-like population of human CD1d-restricted T cells expressing intermediate levels of promyelocytic leukemia zinc finger", J. Immunol., 2011; 187(1):309-315.

Croft, M., "Control of immunity by the TNFR-related molecule OX40 (CD134)", Annu. Rev. Immunol., 2010; 28:57-78.

D'Andrea, A. et al., "Neonatal invariant Valpha24+ NKT lymphocytes are activated memory cells", Eur. J. Immunol., 2000; 30(6):1544-1550.

De Lalla, et al., "Invariant NKT cell reconstitution in pediatric leukemia patients given HLA-haploidentical stem cell transplantation defines distinct CD4+ and CD4-subset dynamics and correlates with remission state", J. Immunol., 2011; 186(7):4490-4499.

Metelitsa, L S. , "Anti-tumor potential of type I NKT cells against CD1d-positive and CD1d-negative tumors in humans", Clin. Immunol., 2011; 140(2):119-129.

Der Vliet, H. J. et al., "Human natural killer T cells acquire a memory-activated phenotype before birth", Blood, 2000; 95(7):2440-2442.

Dhodapkar, M. V. et al., "A Reversible Defect in Natural Killer T Cell Function Characterizes the Progression of Premalignant to Malignant Multiple Myeloma", J. Exp. Med., 2003; 197(12):1667-1676.

Dhodapkar, M. V. "Harnessing human CD1d restricted T cells for tumor immunity: progress and challenges", Front Biosci., 2009; 14:796-807.

Dotti, G. et al., "Design and development of therapies using chimeric antigen receptor-expressing T cells", Immunol. Rev., 2014; 257(1):107-126.

Eger, K. A. et al., Human natural killer T cells are heterogeneous in their capacity to reprogram their effector functions. PLoS. One. 2006; 1:e50, 9 pages.

Metelitsa, L S. et al., "Natural killer T cells infiltrate neuroblastomas expressing the chemokine CCL2", J. Exp. Med., 2004; 199(9):1213-1221.

(56) References Cited

OTHER PUBLICATIONS

Exley, M. A. et al., Selective activation, expansion, and monitoring of human iNKT cells with a monoclonal antibody specific for the TCR alpha-chain CDR3 loop. Eur. J. Immunol. 2008; 38(6):1756-1766.

Molling, J. W. et al., "Low levels of circulating invariant natural killer T cells predict poor clinical outcome in patients with head and neck squamous cell carcinoma", J. Clin. Oncol., 2007; 25(7):862-868.

Gattinoni, L. et al., "Acquisition of full effector function in vitro paradoxically impairs the in vivo antitumor efficacy of adoptively transferred CDS+ T cells", J. Ciin. Invest, 2005; 115(6):1616-1626.

Graef, P. et al., "Serial transfer of single-cell-derived immunocompetence reveals sternness of CDS(+)central memory T cells", Immunity, 2014; 41(1):116-126.

Grupp, S. A. et al.,". et al.,". et al., "Chimeric antigen receptor-modified T cells for acute lymphoid leukemia", N. Engi. J. Med., 2013; 365(16): 1509-1515.

Heczey, A. et al., "Invariant NKT cells with chimeric antigen receptor provide a novel platform for safe and effective cancer immunotherapy", Blood, 2014; 124(18):2824-2833.

Jena, B. et al., "Chimeric antigen receptor (CAR)-specific monoclonal antibody to detect CD19-specific T cells in clinical trials", PLoS. One, 2013; 8(3):e57838, 12 pages.

Kalos, M. et al., "Adoptive T cell transfer for cancer immunotherapy in the era of synthetic biology", Immunity, 2013; 39(1):49-60.

Kim, E. Y. et al., "The transcriptional programs of iNKT cells", Semin. Immunol., 2015; 27(1):26-32.

King, M. A. et al., "Human peripheral blood leucocyte non-obese diabetic-severe combined immunodeficiency interleukin-2 receptor gamma chain gene mouse model of xenogeneic graft-versus-host-like disease and the role of host major histocompatibility complex", Clin. Exp. Immunol., 2009; 157(1):104-118.

Klebanoff, C. A,. et al., "Central memory self/tumor-reactive CDS+ T cells confer superior antitumor immunity compared with effector memory T cells", Proc. Nati. Acad. Sci. U.S.A, 2005; 102(27):9571-9576.

Kochenderfer, J. N. et al., "B-cell depletion and remissions of malignancy along with cytokine-associated toxicity in a clinical trial of anti-CD19 chimeric-antigen-receptor-transduced T cells", Blood, 2012; 119(12):2709-2720.

Pule, M. A. et al., "A chimeric T cell antigen receptor that augments cytokine release and supports clonal expansion of primary human T cells", Mol. Ther., 2005; 12(5):933-941.

Ramos, C. A. et al., "CAR-T Cell Therapy for Lymphoma", Annu. Rev. Med., 2016; 67:165-183.

Lantz, O. et al., "An invariant T cell receptor alpha chain is used by a unique subset of major histocompatibility complex class I-specific CD4+ and CD4-8-T cells in mice and humans", J. Exp. Med., 1994; 180(3):1097-1106.

Lee, P. T. et al., "Distinct functional lineages of human V(alpha)24 natural killer T cells", J. Exp. Med., 2002; 195(5):637-641.

Liu, D. et al., "Medulloblastoma expresses CD1d and can be targeted for immunotherapy with NKT cells", Clin. Immunol., 2013; 149(1):55-64.

Loza, M. J. et al., "NKT and T cells: coordinate regulation of NK-like phenotype and cytokine production", Eur. J. Immunol., 2002; 32(12):3453-3462.

Morris, E. S. et al., "NKT cell-dependent leukemia eradication following stem cell mobilization with potent G-CSF analogs", J. Ciin. Invest, 2005; 115(11):3093-3103.

Matsuda, J. L. et al., "Homeostasis of V alpha 14i NKT cells", Nat. Immunol., 2002; 3(10):966-974.

Okada, R. et al., "Phenotypic classification of human CD4+ T cell subsets and their differentiation", Int. Immunol., 2008; 20(9):1189-1199.

Pegram, H. J. et al., "CAR therapy for hematological cancers: can success seen in the treatment of 8-cell acute lymphoblastic leukemia be applied to other hematological malignancies?", Immunotherapy, 2015; 7(5):545-561.

Porcelli, S. et al., "Analysis of T cell antigen receptor (TCR) expression by human peripheral blood CD4-8-alpha/beta T cells demonstrates preferential use of several V beta genes and an invariant TCR alpha chain", J. Exp. Med., 1993; 178(1):1-16.

Pillai, A. B. et al., "Host NKT cells can prevent graft-versus-host disease and permit graft antitumor activity after bone marrow transplantation", J. Immunol., 2007; 178(10):6242-6251.

Porter, D. L. et al., "Chimeric antigen receptor-modified T cells in chronic lymphoid leukemia", N. Engl. J. Med., 2011; 365(S):725-733.

Bendelac et al., "CD1 Recognition by Mouse NK1+ T Lymphocytes" Science 268:863-865 (1995).

Cambridge Dictionary, available on the internet at dictionary(dot)cambridge(dot)org/us/dictionary/english/majority, definition of 'majority'.

DelaRosa et al., Vα24+ NKT cells are decreased in elderly humans, Experimental Gerontology 37:213-217 (2002).

Extended European Search Report dated Jan. 2, 2019 in European Application No. 16783876.

Gerdes et al., "Green fluorescent protein: applications in cell biology," FEBS Lett. 289:44-47 (1996).

Hammand et al., "CD1d-Restricted NKT Cells: An Interstrain Comparison," The Journal of Immunology 167:1164-1173 (2001).

Hartmann et al., "Two dominant-acting selectable markers for gene transfer studies in mammalian cells," Proc. Natl. Acad. Sci. USA, 85-80478051 (1988).

Herrera-Estrella et al., "Chimeric genes as dominant selectable markers in plant cells," EMBO J. 2(6):987-995 (1983).

International Search Report and Written Opinion issued in Application No. PCT/US16/28693, dated Jul. 21, 2016.

Jefferson et al., "GUS fusions: β-glucuronidase as a sensitive and versatile gene fusion marker in higher plants," EMBO J., 6(13):3901-3907 (1987).

Nakagome et al., "Antigen-sensitized CD4+CD62Llow memory/effector T helper 2 cells can induce airway hyperresponsiveness in an antigen free setting," Respiratory Research 6(1):46 (2005).

Kronenberg et al., "The Unconventional Lifestyle of NKT Cells," Nature Reviews, 2:557-568 (2002).

Li et al., "Multiple effects on IL-21 on human NK cells in ex vivo expansion," Immunobiology 220:876-888 (2015).

Lim et al., "Effect of exposure to interleukin-21 at various time points on human natural killer cell culture," Cytotherapy, 16:1419-1430 (2014).

Liu et al.; "Tumor-Associated Macrophages Suffocate NKT Cells: A Novel Tumor Escape Mechanism and a Target for Therapy," The Journal of Immunology Apr. 1, 2011; 186 (1 Supplement) 48. 7.

Liu et al., "Cooperation of Invariant NKT Cells and CD4 +CD25+ T Regulatory Cells in the Prevention of Autoimmune Myasthenia," Journal of Immunology 175:7898-7904 (2005).

Matsuda et al., "CD1 d-restricted iNKT Cells, the 'Swiss-Army Knife' of the Immune System," Current Opinion in Immunology 20:358-368 (2008).

Motohashi et al., "A Phase I-II Study of α-Galactosylceramide-Pulsed IL-2/GM-CSF-Cultured Peripheral Blood Mononuclear Cells in Patients with Advanced and Recurrent Non-Small Cell Lung Cancer," The Journal of Immunology 2492-2501 (2011).

Ngai et al., "IL-21 Selectively Protects CD62L + NKT Cells and Enhances Their Effector Functions for Adoptive Immunotherapy," The Journal of Immunology (2018).

Pellicci et al., "DX5/CD49b-Positive T Cells Are Not Synonymous with CD1d-Dependent NKT Cells," The Journal of Immunology 175:4416-4425 (2005).

Reiss et al., "A family of binary gene vectors with low intertransformant variation," Plant Physiol. (Life-Sci. Adv.), 13:143-149 (1994).

Tamura et al., "Blasticidin S Deaminase Gene (BSD): a New Selection Marker Gene for Transformation of Arabidopsis thaliana and Nicotiana tabacum," Biosci. Biotechnol. Biochem. 59(12):2336-2338 (1995).

Tian et al., "CD62L+ NKT cells have prolonged persistence and antitumor activity in vivo," J Clin Invest. 126(6):2341-2355 (2016).

(56) References Cited

OTHER PUBLICATIONS

Yvon et al., "Immunotherapy of Metastatic Melanoma Using Genetically Engineered GD2-Specific T Cells," *Clinical Cancer Research*; 15:5852-5860 (2009).

* cited by examiner

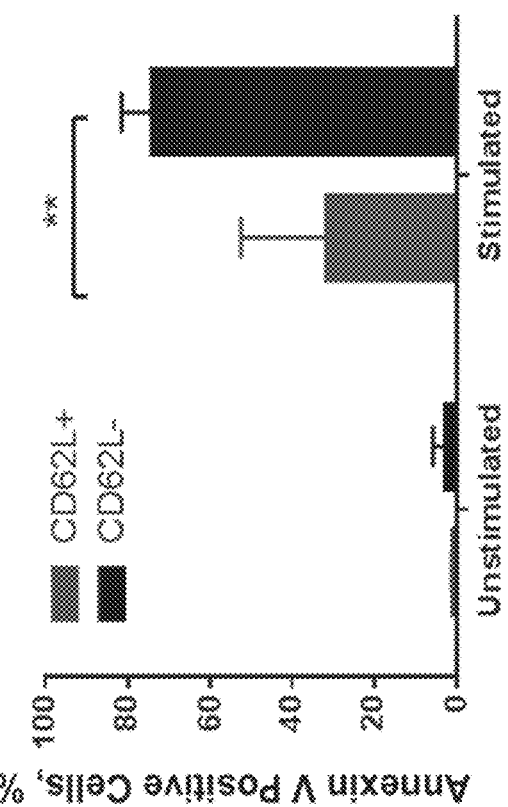
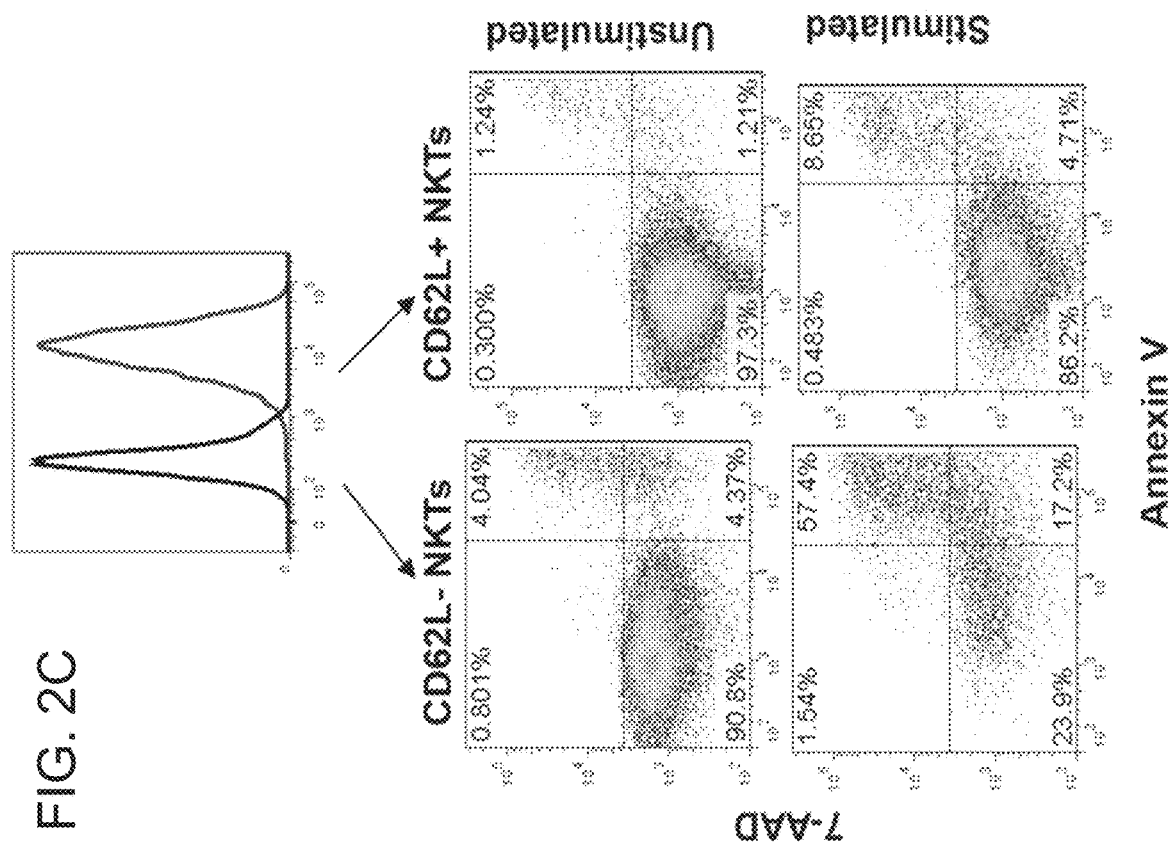
FIG. 2C

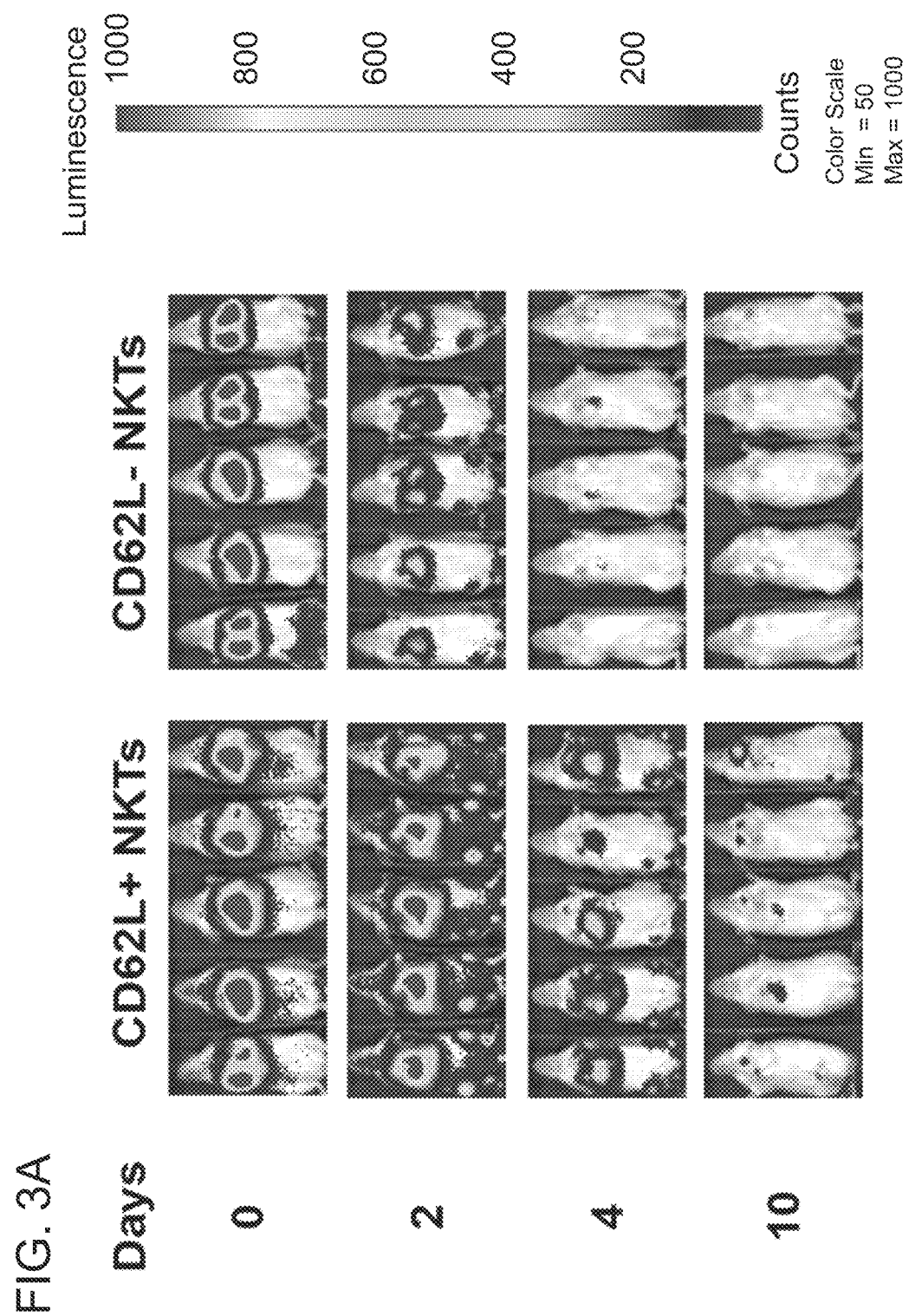

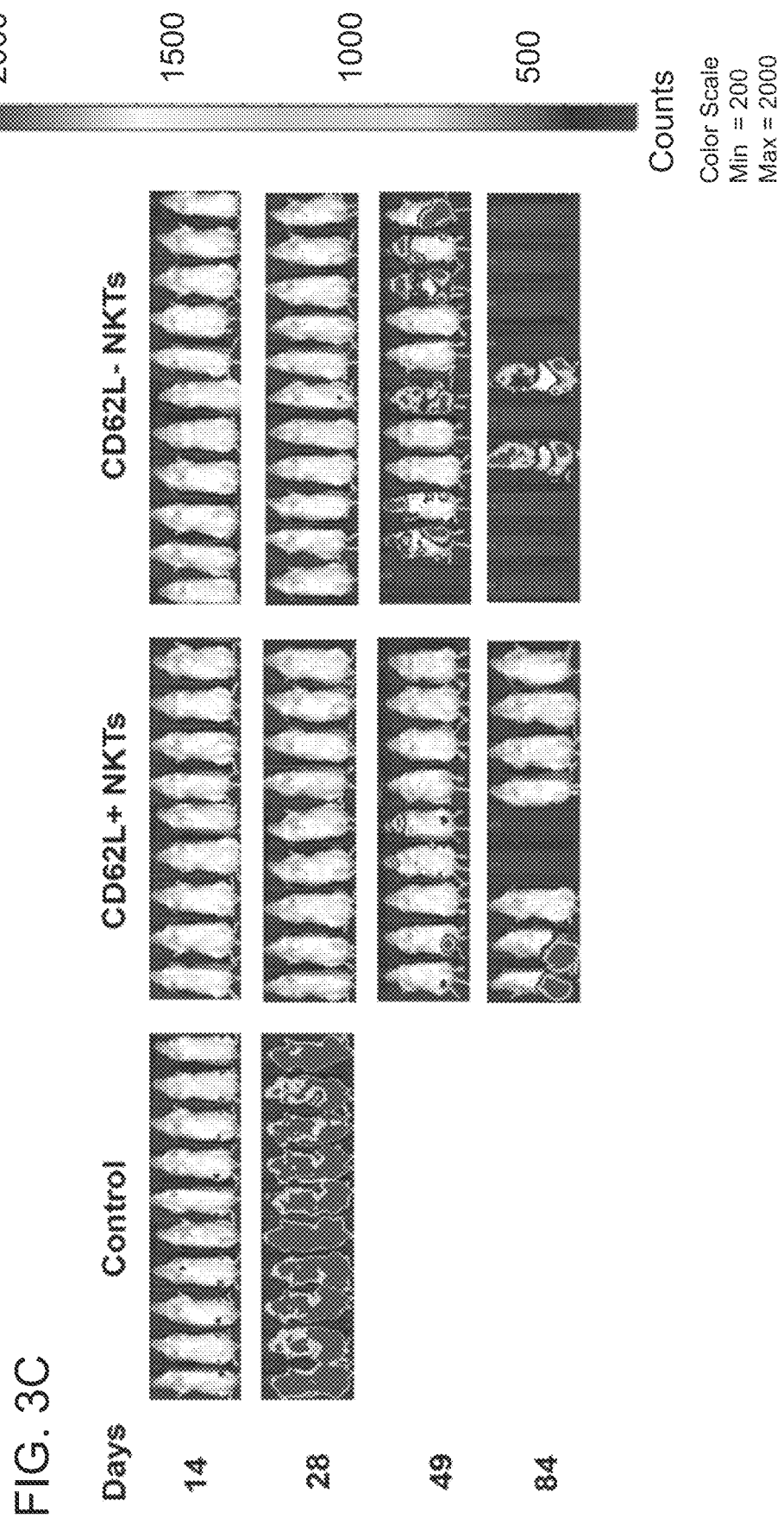

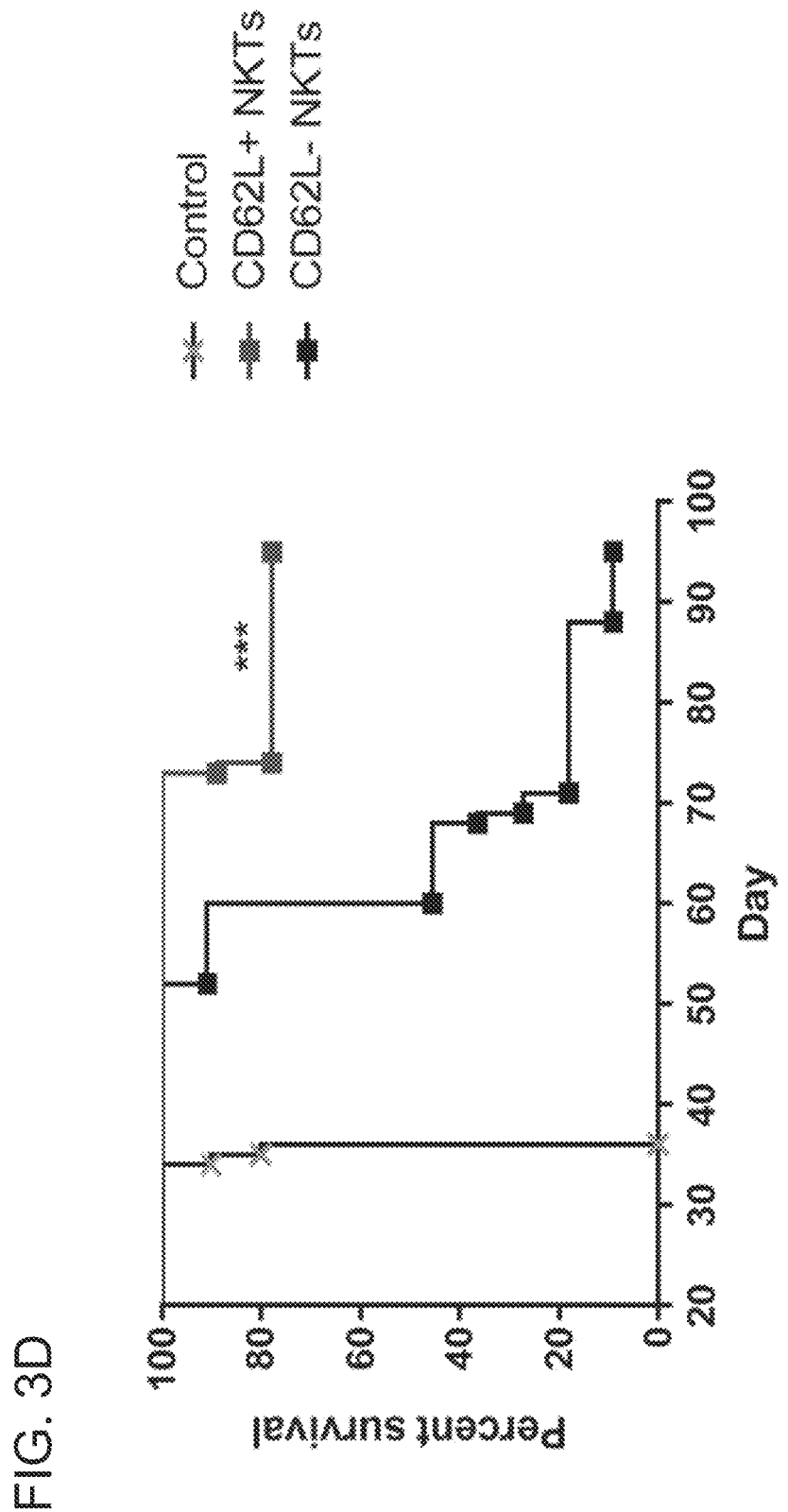

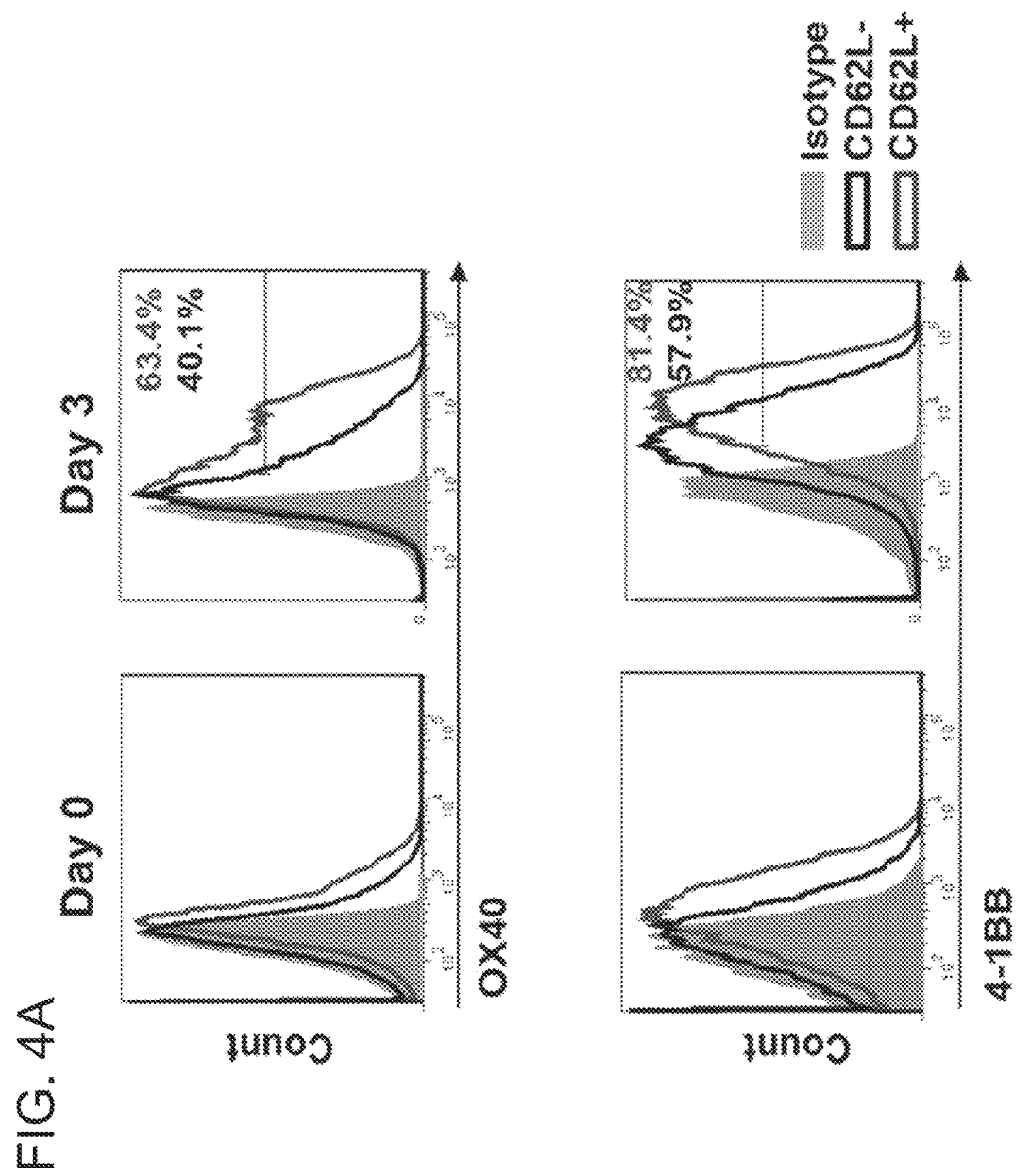

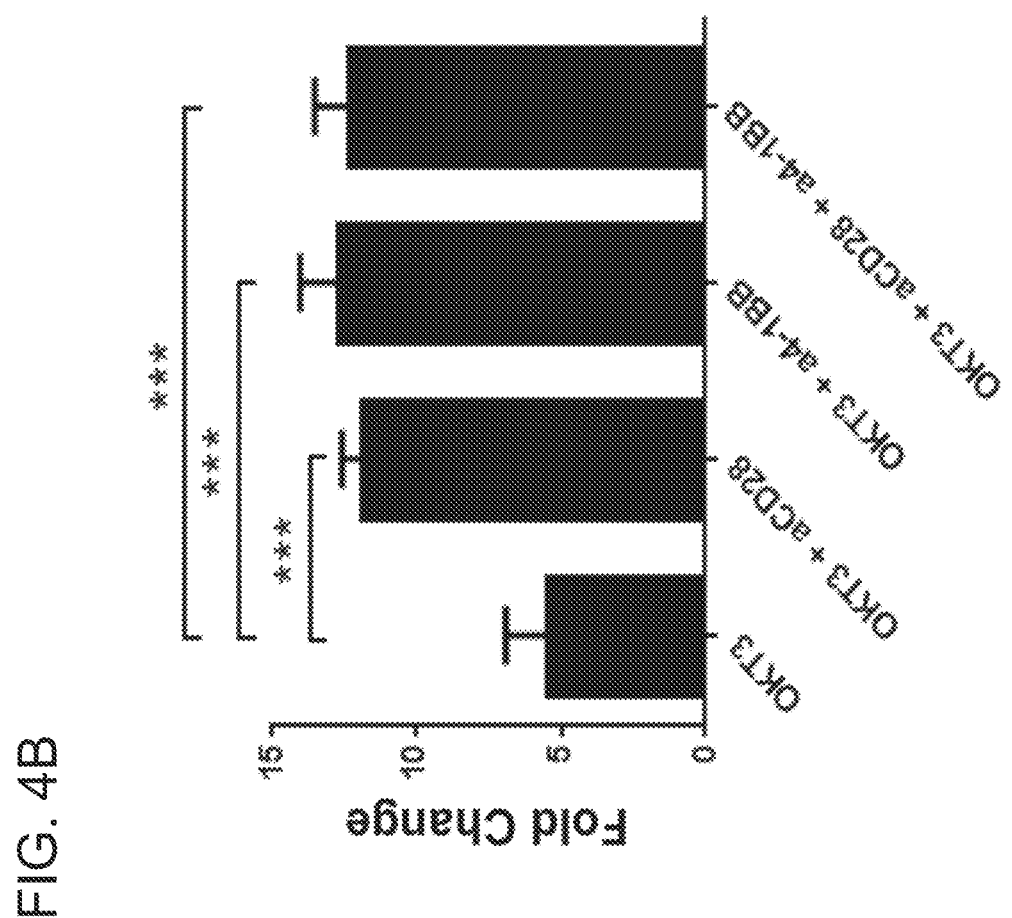

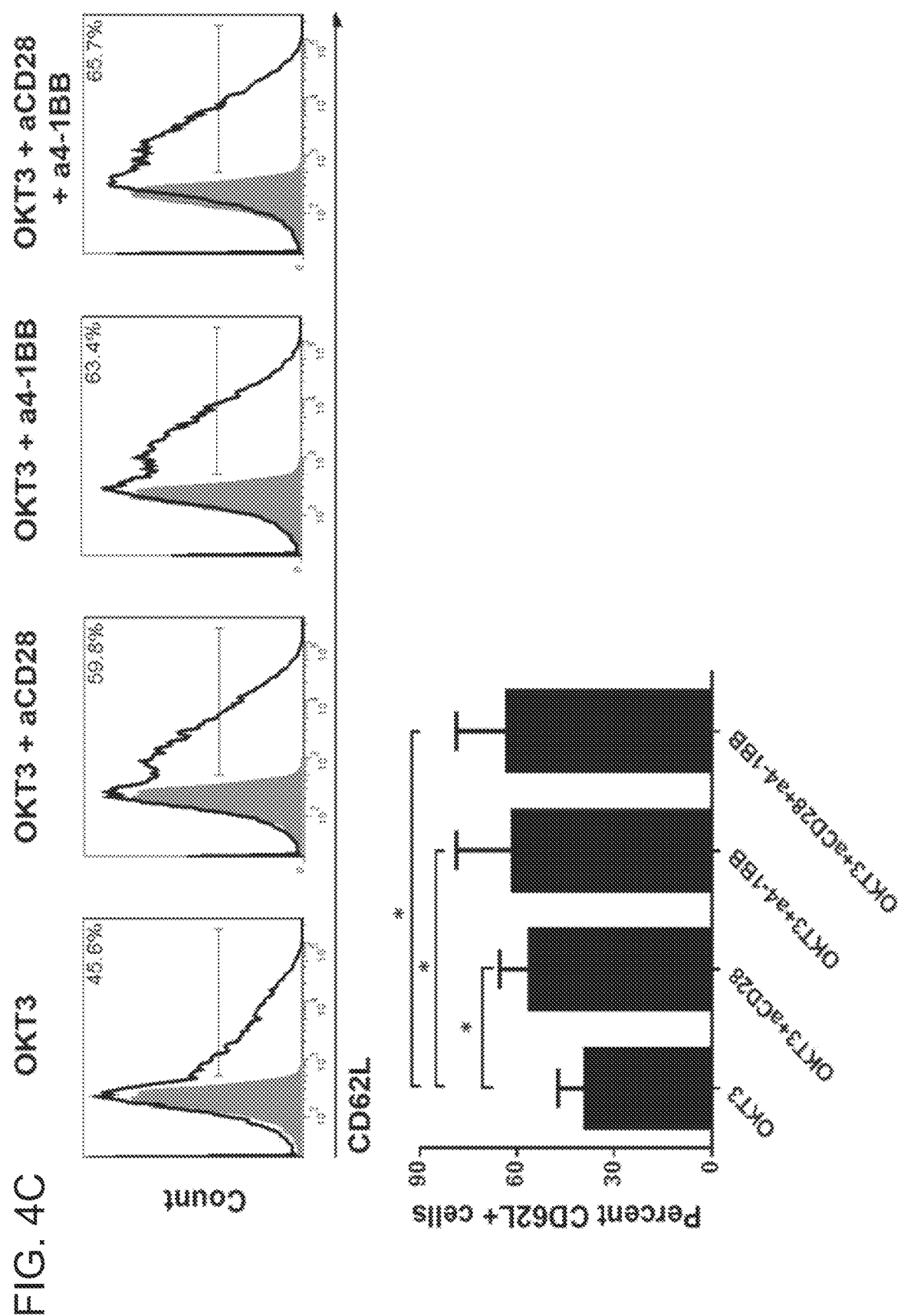

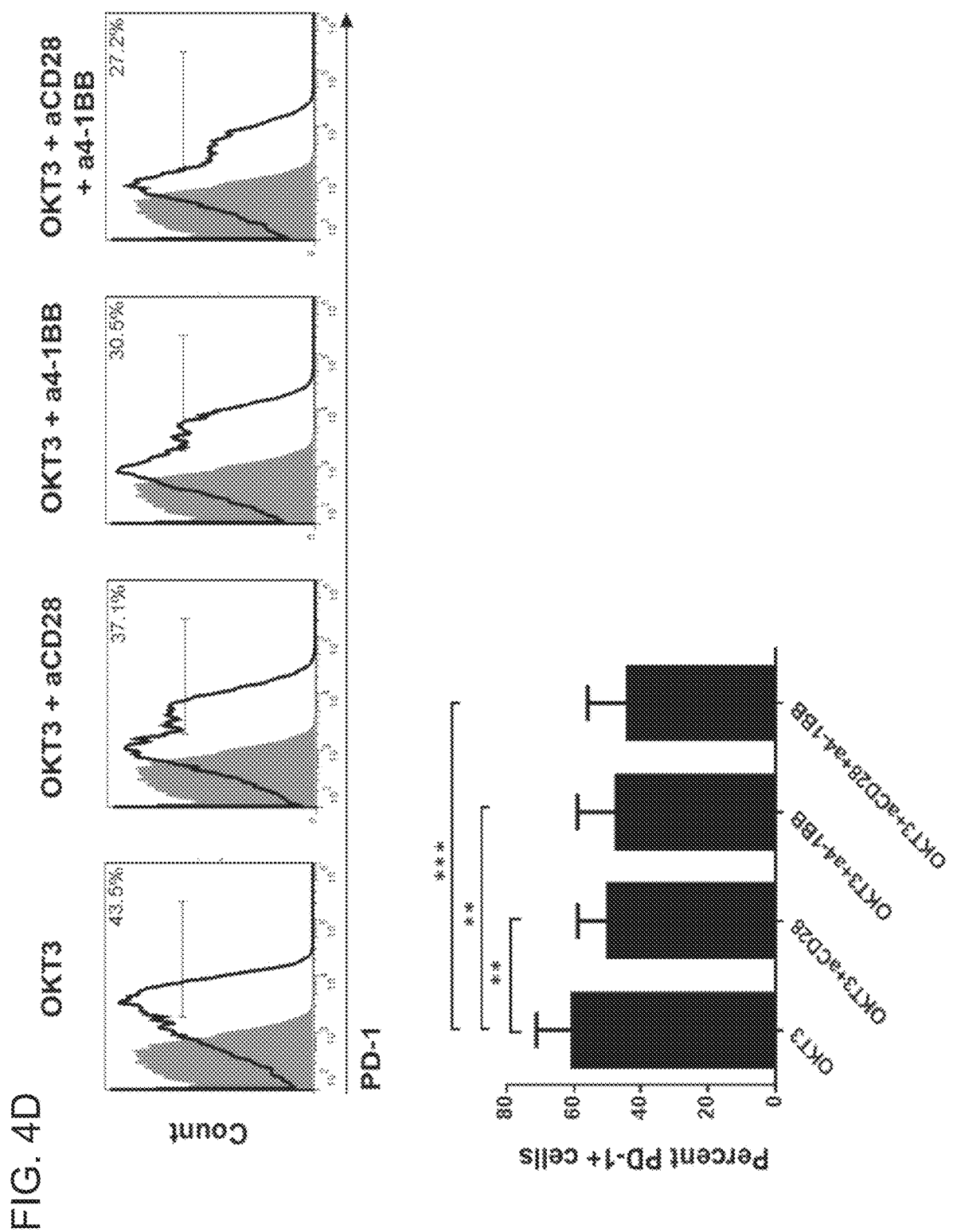

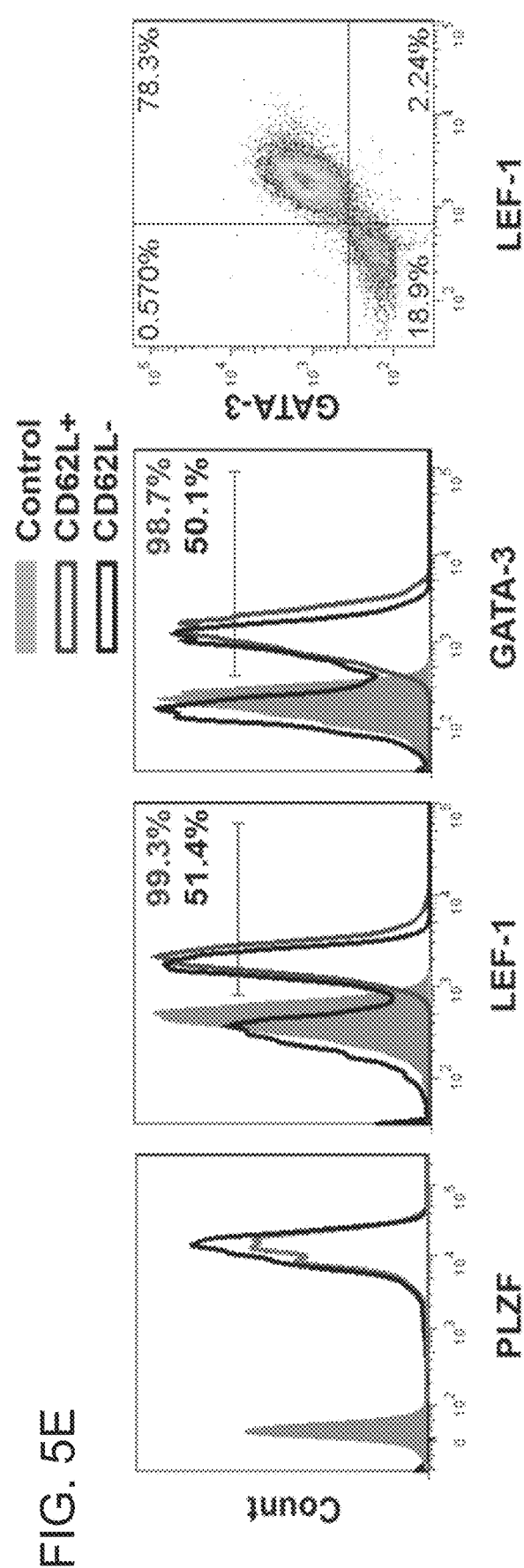

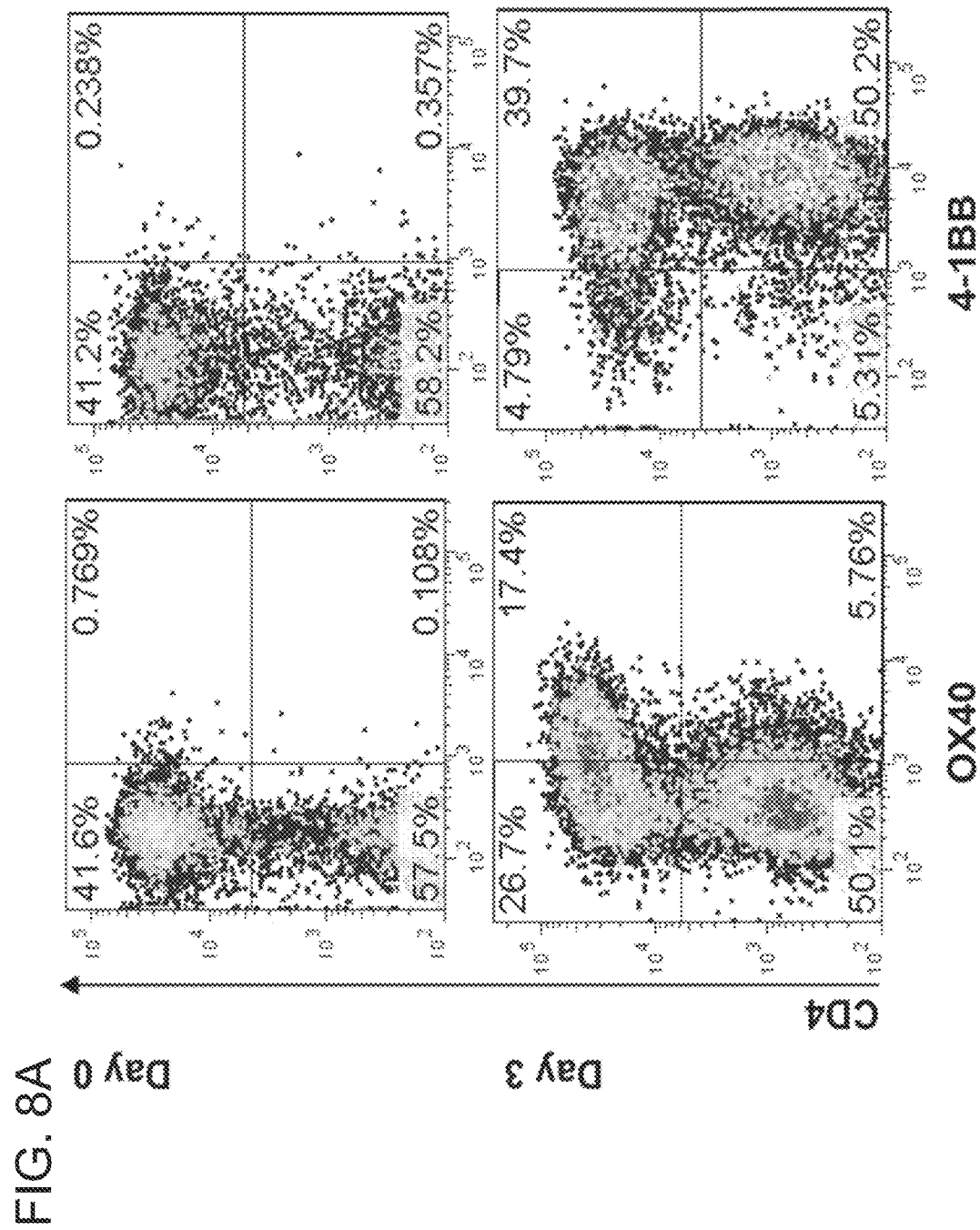

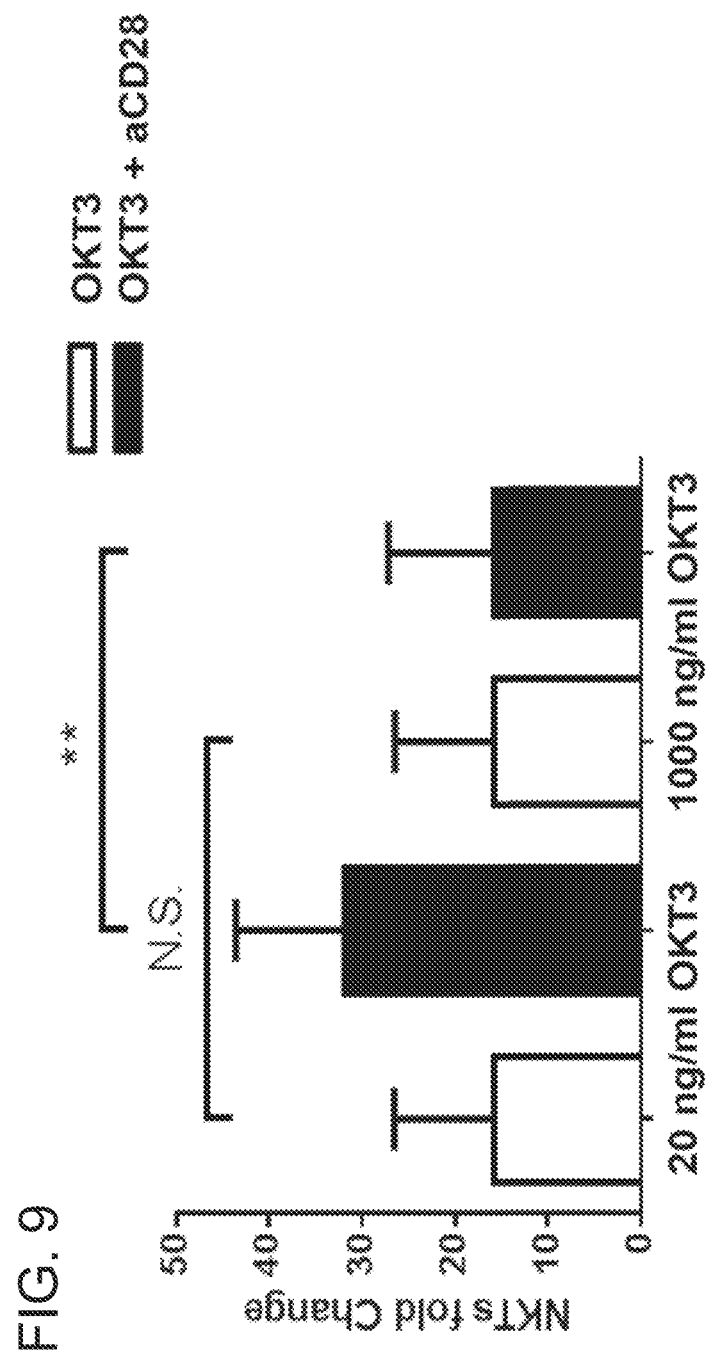

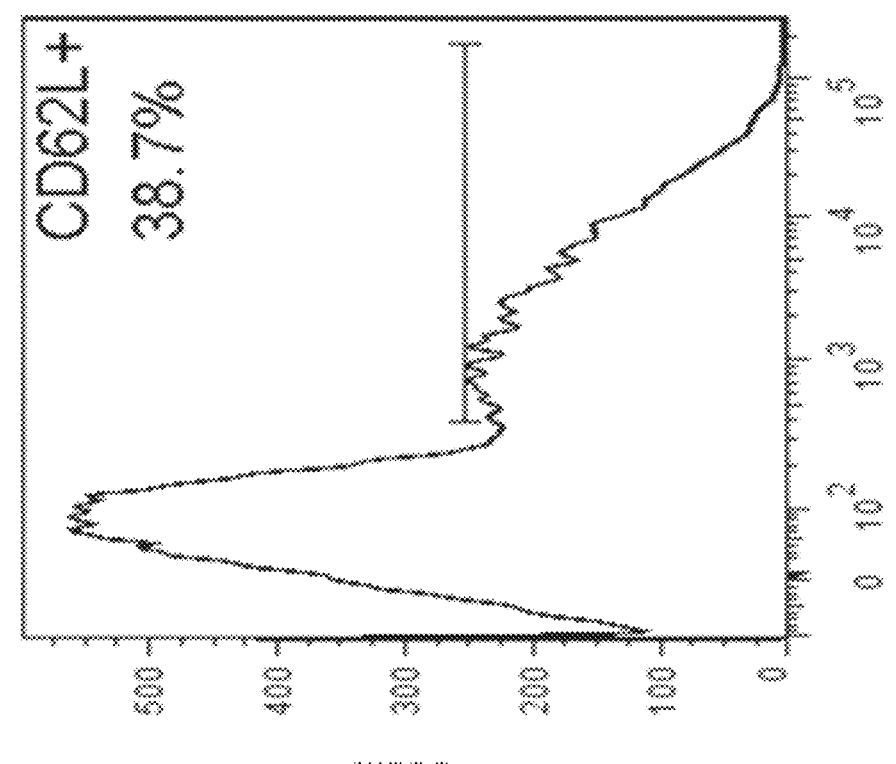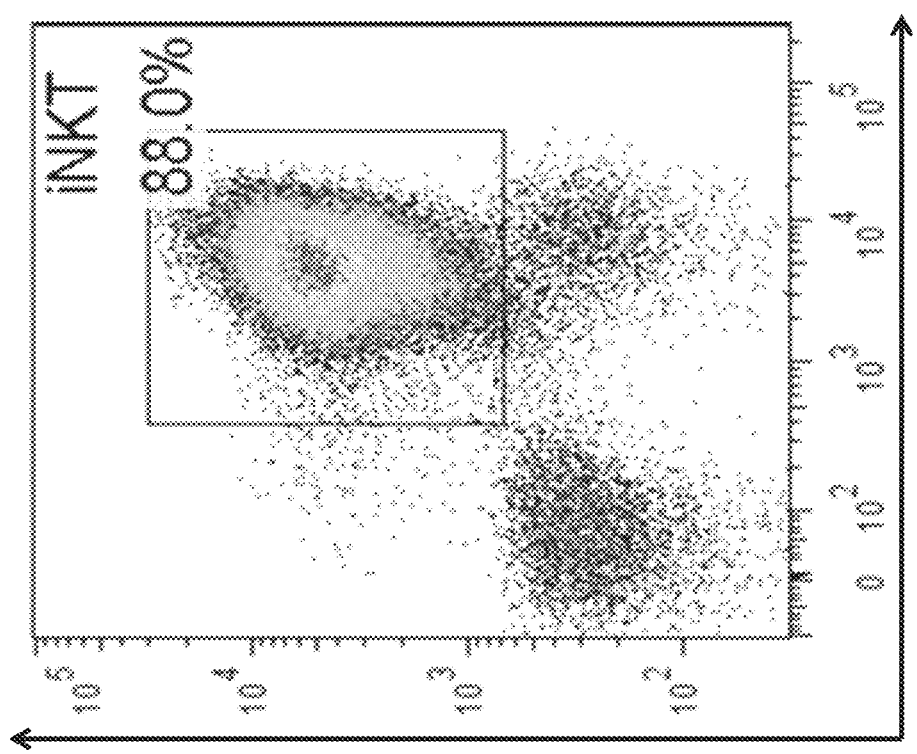
FIG. 14

NKT-CELL SUBSET FOR IN VIVO PERSISTENCE AND THERAPEUTIC ACTIVITY AND PROPAGATION OF SAME

This application is a continuation of U.S. Non-Provisional Patent Application Ser. No. 15/135,453 filed Apr. 21, 2016, which claims priority to U.S. Provisional Patent Application No. 62/151,690 filed Apr. 23, 2015, and to U.S. Provisional Patent Application No. 62/309,525 filed Mar. 17, 2016, all of which are incorporated herein by reference in their entirety.

STATEMENT REGARDING FEDERALLY SPONSORED RESEARCH OR DEVELOPMENT

This invention was made with government support under RO1 CA116548 and P50 CA126752 awarded by National Institutes of Health. The government has certain rights in the invention.

TECHNICAL FIELD

Embodiments of the disclosure encompass at least the fields of cell biology, molecular biology, immunology, and medicine, including at least cancer medicine.

BACKGROUND

Type-I NKT cells (NKTs) are an evolutionary conserved subset of innate lymphocytes that express invariant TCRα-chain Vα24-Jα18 and react to self- or microbial-derived glycolipids presented by monomorphic HLA class-I like molecule CD1d (Porcelli et al. (1993); Lantz and Bendelac, 1994; Bendelac et al., 1995; Kim et al., 2015). The potential importance of NKTs for tumor immunity and immunotherapy has been demonstrated in multiple models of cancer in mice and in early stage clinical trials in cancer patients (McEwen-Smith et al., 2015; Dhodapkar, 2009; Exley and Nakayama, 2011; Motohashi et al., 2011; Yamasaki, 2011; Taniguchi et al., 2015). In contrast to T cells, NKTs effectively traffic to the tumor site and can mediate anti-tumor responses either via direct killing of CD1d+ tumor cells, inhibition of tumor-supportive macrophages, or trans-activation of NK cells (Metelitsa, 2011). Several studies have revealed strong positive associations between the numbers of tumor-infiltrating or circulating NKTs and improved disease outcome in patients with diverse tumor types (Dhodapkar, 2009; Metelitsa et al., 2004; Tachibana et al., 2005; Molling et al., 2007; Cariani et al., 2012; Cariani et al., 2012). Conversely, tumor progression is often accompanied by a decrease in NKT-cell number or functional activity (16), or the downregulation of CD1d expression on malignant cells (Dhodapkar et al., 2003). To counteract these tumor escape mechanisms, methods were developed to expand primary human NKTs to clinical scale ex vivo and to redirect their cytotoxicity against tumor cells via transgenic expression of chimeric antigen receptors (CARs) (Heczey et al., 2014). Similar to the observations reported in CAR T-cell clinical trials (Kalos and June, 2013; Dotti et al., 2014), there is a strong correlation between the anti-tumor efficacy and in vivo persistence of CAR NKT-cell products in a xenogenic tumor model (Heczey et al., 2014). However, the mechanisms that govern ex vivo expansion and subsequent in vivo persistence of human NKTs remain largely unknown, impeding rational design of NKT cell-based cancer immunotherapy.

Recent global transcriptional profiling studies demonstrated that NKTs, though they share properties with T and NK cells, are a distinct population of lymphocytes (Cohen et al., 2013). In the mouse, the developmental program and functional differentiation of NKTs have been characterized quite extensively during the last decade, as summarized in recent reviews (Kim et al., 2015; Contantinides and Bendelac, 2013). Several key features of murine NKTs have also been confirmed in their human counterparts. Both in mice and humans, NKTs diverge from T cells at the stage of CD4+CD8+ (double positive, DP) thymocytes. Unlike T cells, which are positively selected by thymic epithelial cells, NKTs are selected by CD1d-expressing DP thymocytes (Gapin et al., 2001). The expression of promyelocytic leukemia zinc finger transcription factor (PLZF) immediately after positive selection enables intrathymic expansion and effector/memory-like differentiation of NKTs (Savage et al., 2008). Peripheral NKTs are long-lived lymphocytes and their post-thymic maintenance largely depends on slow IL-15-mediated homeostatic proliferation (Matsuda et al., 2002; Baev et al., 2004). In human peripheral blood, NKTs are divided into two major functional subsets based on CD4 expression: CD4+ and CD4− (mostly CD8/CD4-double negative, DN) (Lee et al., 2002). The CD4+ subset is highly enriched in neonate NKTs and undergoes fewer homeostatic divisions compared with the CD4− subset in adults (Baev et al., 2004), suggesting that CD4+ NKTs could contribute to the long-term persistence of adoptively transferred therapeutic NKTs under certain conditions. However, ex vivo expansion of human NKTs in response to antigenic stimulation, e.g. with αGalactosylceramide (αGalCer), produces similar numbers of CD4+ and DN NKTs (28). NKTs also exhibit an NK-like linear differentiation with acquisition of CD161 and then CD56 expression. Like in T cells, the expression of CD56 is associated with terminal differentiation and the loss of proliferative potential (Loza et al., 2002).

In contrast to peripheral T cells, which have a well-established developmental hierarchy from naïve to central memory to effector memory to terminal effector cells (Sallusto et al., 2004), NKTs are broadly described as cells with "activated/memory" phenotype without the naive state (D'Andrea et al., 2000; Kronenberg and Gapin, 2002). In cord blood, the majority of NKTs are CD4+ and co-express CD45RO with CD62L and CCR7 without immediate effector function (Baev et al., 2004; D'Andrea et al., 2000; Eger et al., 2006), thus resembling central-memory CD4 T cells. In adult peripheral blood, NKTs are equally split between CD4+ and CD4− subsets (albeit with significant inter-individual variability). Adult NKTs lack a clear demarcation between "memory" and "effector" states, as they variably express memory markers and have immediate effector functions such as cytokine production and cytotoxicity (Baev et al., 2004; Eger et al., 2006). The majority of adult NKTs even in the elderly express CD28 (DelaRosa et al., 2002), making them distinct from terminally differentiated T effector cells (Okada et al., 2008).

Recent reports have demonstrated that CD62L+ central memory T cells have stem cell properties and superior therapeutic activity in cell therapy products (Graef et al., 2014; Wang et al., 2012; Sommermeyer et al., 2015). The functional significance of CD62L expression in NKTs remains unknown. In this disclosure, the CD62L+ subset is required for NKT cell ex vivo expansion and in vivo persistence. Importantly, when engineered to express CD19-specific CAR (CAR.CD19), CD62L+ but not CD62L− CAR.CD19 NKTs produced sustained tumor regression in a B-cell lymphoma model in NSG mice. CD62L+ NKTs could be maintained during ex vivo expansion when provided with certain costimulatory ligands. With this knowledge, one can engineer co-stimulatory artificial antigen-presenting cells (aAPC) that can be used to generate NKTs and CAR-NKTs with superior therapeutic activity in patients with cancer, for example.

BRIEF SUMMARY

Methods and compositions of the present disclosure concern immunotherapies for an individual in need thereof. In some embodiments, the individual is in need of a therapy that targets a particular antigen-bearing cell for destruction, such as cancer, for example. The disclosure generally provides for the use of NKT cells for immunotherapy based upon improvements of methods to generate clinically useful amounts and efficacies of NKT cells.

Embodiments of the disclosure provide CD62L+ NKT cells that have superior in vivo persistence and anti-tumor activity. Embodiments of the disclosure allow for effective expansion of NKT cells such that they can be used for therapeutic applications. NKTs of the present disclosure have enhanced survival and expansion that are associated with the expression of CD62L. The expression of CD62L is present in the NKT cells and is maintained in the cells because of co-stimulation of the NKT cells. Embodiments of the disclosure include co-stimulation of NKT cells by any method to maintain CD62L expression. The NKT cells are exposed to co-stimulation using one or more methods, such as upon exposure to one or more cytokines (including at least IL-21), one or more agonistic antibodies that bind to a costimulatory receptor, and/or artificial antigen presenting cells that express CD1d and one or more costimulatory receptor ligands, for example. Thus, in specific embodiments one can utilize artificial antigen-presenting cells for the generation of CD62L-enriched NKTs for effective cancer immunotherapy.

In one embodiment, there is a method of preparing natural killer T (NKT) cells for use in immunotherapy, comprising the step of enriching a population of NKT cells for CD62L-positive NKT cells. In a specific embodiment, the CD62L-positive NKT cells are activated by stimulation of T-cell receptor and co-stimulation by costimulatory receptors and/or cytokines. In some cases, the method further comprises the step of delivering a therapeutically effective amount of the cells to an individual in need of therapy. In certain aspects, the cells are modified to express one or more chimeric antigen receptors, T-cell receptors, one or more cytokines, one or more cytokine receptors, one or more chimeric cytokine receptors, or a combination thereof.

In a certain embodiment, there is a method of treating an individual for a medical condition using immunotherapy, comprising the steps of a) enriching a population of NKT cells for CD62L-positive NKT cells or obtaining a population of NKT cells that are enriched for CD62L-positive NKT cells; and b) providing a therapeutically effective amount of the CD62L-positive NKT cells to the individual.

In an embodiment, there is a method of treating an individual for a medical condition using immunotherapy, comprising the steps of expanding CD62L+ NKT cells from a population mixture of CD62L+ NKT cells and CD62L– NKT cells by exposing the population mixture to one or more co-stimulatory agents to enrich for and produce co-stimulated CD62L+ NKT cells; and providing a therapeutically effective amount of the co-stimulated CD62L+ NKT cells to the individual. In specific embodiments, stimulatory agents and the co-stimulatory agents comprise a) one or more cytokines; b) a substrate that comprises an agonistic antibody or ligand for T-cell receptor (e.g. OKT3 mAb, 6B11 mAb, or recombinant human CD1d with bound agonistic glycolipid such as alpha-galactosylceramide) and one or more agonistic antibodies that target co-stimulatory receptors; or c) an antigen presenting cell that comprises CD1d expression and that comprises expression of one or more ligands of one or more costimulatory receptors. In certain embodiments, the cytokine is selected from the group consisting of IL-21, IL-2, IL-7, IL-15, IL-12, TNFalpha, and a combination thereof. The substrate may be a bead, plate, or a gel. In a specific embodiment, the antigen presenting cell is transduced with one or more polynucleotides to express one or more ligands of one or more co-stimulatory receptors. The co-stimulatory receptor may be CD28, OX40, 4-1BB, ICOS, CD40, CD30, CD27, or a combination thereof. The ligand of the co-stimulatory receptor may be CD80, CD86, OX40L, 4-1BBL, ICOS ligand, CD154, CD30L, or a combination thereof.

In particular embodiments, NKT cells encompassed by the disclosure comprise a genetic modification. In specific aspects, the genetic modification provides the cells with cancer cell-targeting activity, such as targeting of an antigen on cancer cells. The genetic modification may comprise a T-cell receptor and/or a chimeric antigen receptor. In some cases, the NKT cells are genetically modified after the exposing of the population to one or more co-stimulatory agents. The NKT cells may be genetically modified within 1, 2, 3, 4, 5, 6, or more days after the exposing of the population to one or more co-stimulatory agents.

In a certain embodiment, there are methods of producing NKT cells for immunotherapy, comprising the step of costimulating a population of NKT cells to maintain CD62L expression in at least some of the NKT cells. In some cases, the methods further comprise the step of providing an effective amount of the NKT cells to an individual in need thereof.

In one embodiment, there is a method of producing NKT cells for immunotherapy, comprising the step of exposing a pre-sorted population of CD62L+ NKT cells or a mixed population of CD62L+ NKT cells and CD62L– NKT cells to one or more co-stimulatory agents designed to purposely enrich or retain a population of CD62L+ NKT cells. In some cases, the method further comprises the step of obtaining the mixed population. In specific embodiments, the mixed population is from an individual to which the enriched population will be delivered. In certain aspects, the mixed population is from an individual that is different from the individual to which the enriched population will be delivered. The mixed population may be from a depository or obtained commercially.

In one embodiment, there is a composition of matter that comprises a non-natural cell expressing CD1d and expressing one or more ligands of one or more co-stimulatory receptors.

BRIEF DESCRIPTION OF THE DRAWINGS

FIGS. 2A-2E. Functional characterization of CD62L+ and CD62L− NKTs. (2A) Luciferase-transduced CD1d+ DAOY cells were pulsed with PBS (control) or αGalCer overnight followed by co-culture with CD62L+ or CD62L− magnetically sorted NKTs. Cytotoxicity was analyzed after 4 h by measuring luminescence intensity with a plate reader. Left plot is a representative of 3 donors with no difference in cytotoxicity between NKT subsets. Right plot is a representative of 3 donors with a significant difference in cytotoxicity between NKT subsets. (2B) The concentrations of IFN-γ and IL-4 were measured in 24-h supernatants of αGalCer-stimulated CD62L+ or CD62L− NKTs by the Luminex assay in 3 independent experiments with NKTs from 3 donors. (2C) CFSE-labeled NKTs were magnetically sorted into CD62L+ and CD62L− subsets as confirmed by post-sorting FACS (top plot) and stimulated with irradiated αGalCer-pulsed APC. On day 3 after stimulation, staining for Annexin V and 7-AAD was analyzed in NKTs by FACS after gating on CFSE-positive events. Results are from a representative of 5 donors tested (middle panel). The corresponding bar graph (lower panel) shows Mean±SD of percent Annexin V+ NKTs on day 3 (N=5). (2D) Cell proliferation was assessed on day 6 after stimulation as measured by CFSE dilution. Results are from a representative of 5 donors tested (upper panel) and Mean±SD of CFSE MFI for all 5 donors (lower panel). (2E) Total cell counts were performed at the indicated time intervals after NKT-cell stimulation. Shown are Mean±SD viable cells for a representative donor (upper panel) or fold change for each of 5 donors tested on day 6 after stimulation. *** $P<0.001$, paired t-test.

FIGS. 3A-3D. CD62L+ NKTs have superior in vivo persistence and anti-tumor activity. (3A) Luciferase-transduced NKTs were sorted into CD62L+ and CD62L− subsets and injected to NSG mice. NKT-cell in vivo persistence was monitored with bioluminescence imaging. (3B) Mean±SD of bioluminescence photon count on indicated days after injection of CD62L+ or CD62L− NKTs (P=0.008, paired t-test). (3C) Each mouse received i.v. injection of $2\times10^5$ luciferase-transduced Daudi lymphoma cells (day 0) followed by (day 4) i.v. injection of $10^7$ CAR.CD19-transduced NKTs with IL-2 (1000 U/mouse) or PBS as a control. Tumor growth was monitored using bioluminescent imaging once per week. (3D) Survival probability was analyzed by the Kaplan-Meier method (10 mice per group). The differences in survival were then compared using the Log-rank test.

FIGS. 4A-4D. Co-stimulation maintains CD62L+ NKTs and prevents exhaustion. (4A) NKTs were sorted into CD62L+ and CD62L− subsets and stimulated and examined for expression of 4-1BB and OX40 by FACS before and 3 days after stimulation with αGalCer. Shown are plots from a representative of 4 donors. (4B) CD62L+ NKTs were stimulated on plates coated with the indicated agonistic mAbs. Shown are Mean±SD (N=4) of fold change in absolute NKT-cell number on day 7 after stimulation compared to day 0. $P=0.001$, one-way ANOVA. (4C) CD62L+ NKTs were stimulated as in B and analyzed for CD62L expression (black) vs. isotype control (grey) on day 7. Shown are representative overlay histograms (upper panel) and Mean±SD of percent CD62L+ cells, N=4. (4D) CD62L+ NKTs were stimulated as in B and analyzed for the expression of PD-1 (black) vs. isotype control (grey) on day 12. Shown are representative overlay histograms (upper panel) and Mean±SD of percent PD-1+ cells.  or * $P<0.01$ or $0.001$, one-way ANOVA.;

FIGS. 5A-5E. Phenotypic analysis of freshly isolated and in vitro expanded NKTs. (5A) CD4 and CD62L expression was examined by FACS in primary NKTs (gating on CD3+ Vα24−Jα18+ subset) in freshly isolated cord blood mononuclear cells (CBMC). Plots are from a representative of 5 CBMC donors. (5B) CD4 and CD62L expression was examined in primary NKTs after gating as in A before (day 0) and 12 days after stimulation with αGalCer and in vitro expansion. Plots are from a representative of 10 PBMC donors. (5C) Expression of CCR7, CD27 and CD28 in relationship to CD62L expression in primary NKTs after gating as in A before (day 0) and 12 days after stimulation with αGalCer and in vitro expansion. Plots are from a representative of 6 PBMC donors. (5D) Expression of CD161, CD56 and IL7Rα in relationship to CD62L expression on day 12 after stimulation with αGalCer and in vitro expansion. Plots are from a representative of 3 PBMC donors. (5E) Expression of PLZF, LEF1, and GATA3 in relationship to CD62L expression and co-expression of LEF1 and GATA3 was analyzed using intracellular flow cytometry on day 12 after stimulation with αGalCer and in vitro expansion. Plots are from a representative of 4 PBMC donors.

FIGS. 8A-8B. Expression of co-stimulatory receptors on resting and activated NKTs. (8A) FACS analysis of OX40 and 4-1BB expression in relation to CD4 on resting NKTs (day 12 after primary stimulation) and 3 days after re-stimulation with αGalCer. Plots are from a representative of 6 PBMC donors. (8B) Magnetically sorted CD62L+ and CD62L− NKTs were analyzed for OX40 and 4-1BB expression in relation to CD4 3 days after NKT cell restimulation with αGalCer. Plots are from a representative of 4 PBMC donors.

FIG. 9. The comparison of NKT-cell expansion using low and high concentrations of plate-bound OKT3 mAb. In vitro expanded quiescent NKTs were stimulated with anti-CD3 OKT3 mAb at 20 ng/ml or 1 µg/ml alone or with 500 ng/ml anti-CD28 CD28.2 mAb. Cells were propagated in culture with the IL-2 (200 U/ml) added every other day. At day 12, NKT-cell absolute cell count was performed using trypan blue exclusion assay in triplicate and divided to the input number at day 0. Data are M±SD, N=4. ** P=0.01, paired t test.

FIG. 14 shows that Ramos cells expand NKTs upon secondary stimulation with significant retention of CD62L expression.

DETAILED DESCRIPTION

Figure 1A:
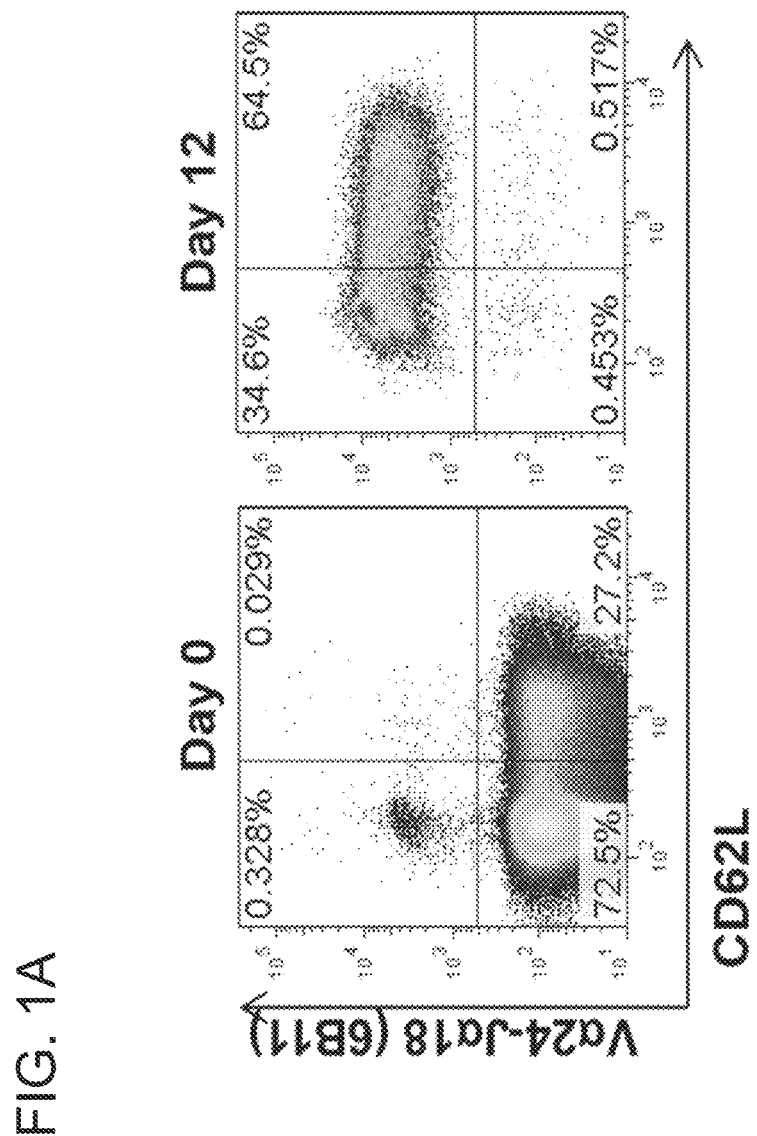
FIGS. 1A-1D. Accumulation of CD62L+ subset in culture after in vitro antigenic stimulation of primary NKTs. (1A) CD62L expression was examined by FACS in primary NKTs from freshly isolated PBMCs (day 0) and 12 days after stimulation with αGalCer and in vitro expansion in culture. (1B) Kinetics of CD62L expression in NKTs at the indicated intervals after primary stimulation (as in 1A) from individual donors (n=10). (1C) Expression of PD-1, TIM-3 and LAG-3 on NKT-cell surface was measured by FACS on days 0 and 12. Representative plots from one of 4 donors (upper panel) or Mean±SD of MFI for all donors (lower panel). (1D) On day 12 after primary stimulation, NKTs were magnetically sorted into CD62L+ and CD62L− subsets followed by RNA isolation and gene expression analysis using Human Immunology Panel v.2 and nCounter Analysis System. The heat map shows the log 2 fold changes (CD62+/CD62L−) of genes with p-values less than 0.02 and average fold change greater than 2. Data were generated from 6 NKT-cell donors (12 paired samples).

The present application incorporates by reference herein 62/151,690, filed Apr. 23, 2015.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

I. General Embodiments

The disclosure provides NKT cells suitable for use in immunotherapy because they are able to be expanded to sufficient levels and persist in vivo at sufficient levels to achieve a therapeutic effect. The NKT cells of the present disclosure are manipulated to express and maintain expression of CD62L that at least in part allows them to have enhanced therapeutic applicability. Such preservation of expression of CD62L in the NKT cells occurs at least in part upon costimulation, including upon exposure to one or more costimulatory agents.

II. NKT Cells and Costimulation Thereof

In particular embodiments, NKT cells are useful for therapeutic application because they have enhanced in vitro expansion and in vivo persistence following exposure to one or more costimulatory agents that allowed the cells to maintain CD62L expression. The one or more costimulatory agents may be of any kind, but in specific embodiments they comprise one or more cytokines; b) a substrate (bead, plate, and so forth, for example) that comprises one or more agonistic antibodies that target co-stimulatory receptors; and/or c) a cell, such as an antigen presenting cell, that comprises CD1d expression and that comprises expression of one or more ligands of one or more costimulatory receptors. In cases wherein the NKT cells are exposed to cytokines, the cytokines may be of any suitable kind, but in specific cases the cytokine is IL-21, IL-2, IL-7, IL-15, IL-12, IL-18, TNFalpha, or a combination thereof. In specific embodiments, the CD62L+ NKT cells express IL-21 receptor and upon culture in the presence of IL-2 and IL-21 retain CD62L expression.

In cases wherein the NKT cells are exposed to one or more costimulatory agents that are agonistic antibodies (in at least some cases that are monoclonal) that immunologically recognize a co-stimulatory receptor, the receptor may be any co-stimulatory receptor. However, in specific embodiments the receptor is CD28, 4-1BB, OX-40, ICOS, CD2, CD27, CD30, GITR, TIM1, LFA1, ICAM1, or HVEM, for example. The antibodies may be affixed to a substrate that allows a population of cells, such as a population of NKT cells, to be sufficiently exposed to the antibodies. The antibodies may be obtained commercially, obtained as a gift, or produced by standard means in the art.

In cases wherein the NKT cells are exposed to a therapeutically effective amount of cells that have antigen presenting cell activity, such as an artificial antigen presenting cell (such as a non-natural cell with antigen presenting cell activity), the cell may be transduced with one or more polynucleotides to express one or more ligands of one or more costimulatory receptors. The cell may be of any kind so long as it expresses one or more ligands of one or more costimulatory receptors, but in at least some cases the cell expresses CD1d also. The cell is an antigen presenting cell, in particular embodiments. In specific cases, a cell that expresses CD1d and/or that expresses one or more ligands of one or more costimulatory receptors is naturally occuring and may be used in the methods encompassed herein. In other cases, a cell that naturally does not naturally express CD1d and/or that does not naturally express one or more ligands of one or more costimulatory receptors is transduced to express the respective component(s) and is used in methods encompassed herein. The ligand of the costimulatory receptor may be of any kind, but in specific embodiments the ligand is CD80, CD86, 4-1BBL, OX40L, ICOSL, CD30L, GITRL, TIM4, LIGHT, and so forth. In cases wherein the cell that has antigen presenting cell activity is transduced with one or more polynucleotides, the polynucleotides maybe comprised on a vector, including a viral vector or non-viral vector (such as a plasmid). Viral vectors include retroviral vectors, lentiviral vectors, adenoviral vectors, adeno-associated viral vectors, and so forth. The vectors will comprise suitable regulatory element(s) for expression in the cell that has antigen presenting cell activity. In some cases the polynucleotide transduced into the cell that has antigen presenting cell activity encodes two or more coding regions, such as encoding two costimulatory receptor ligands. In such a case, the separate coding regions may or may not be regulated by the same regulatory element(s).

In embodiments wherein expression of CD62L on NKT cells is sustained because of co-stimulation of the NKT cells, there may or may not be a general order to the steps for preparing the desired NKT cells. In particular embodiments, NKT cells are obtained from an appropriate source (for example, blood (including peripheral blood, cord blood, and so forth), by sorting (e.g. magnetic bead or FACS sorting) and are present in a mixed population of cells. Following this, the NKT cells are activated via TCR stimulation using a substrate containing agonistic antibody or ligand for T-cell receptor (e.g. OKT3 mAb, 6B11 mAb, or recombinant human CD1d with bound agonistic glycolipid such as alpha-galactosylceramide) or antigen-presenting cells expressing CD1d and bound agonistic glycolipid such as alpha-galactosylceramide. TCR-activated NKT cells may be exposed to co-stimulation to produce higher levels of CD62L+ NKT cells from the population than would occur in the absence of co-stimulation. In some embodiments, prior to delivery to an individual in need thereof and following exposure to one or more costimulatory agents, the NKT cells are manipulated by recombinant means to incorporate one or more characteristics, such as to express one or more therapeutic agents or entities that render the NKT cells therapeutic. In certain embodiments, the cells are genetically modified to provide them with the ability to target an antigen-bearing cell. In specific embodiments, the manipulation is to transduce the NKT cells to express one or more chimeric antigen receptors and/or a T-cell receptor, either or which target a specific antigen of interest. In specific embodiments, the antigen is a tumor antigen.

NKT cells to be utilized for treatment of a medical condition in an individual may originate from the individual to which they will be administered, they may originate from another individual, or they may be obtained from a cell depository. The NKT cells are type 1 NKT cells, in specific embodiments.

NKT cells may or may not be sorted prior to delivery to an individual. In specific embodiments, CD62L-positive NKT cells are not sorted from CD62L-negative NKT cells, but in alternative embodiments they may be sorted. In cases where cells are not sorted, for example based on whether or not they express CD2L, when the cells are not sorted by physical separation they can be enriched using co-stimulation of the cells that results in maintenance of CD62L expression.

In most cases the cells are not sorted based on a particular phenotype, but in some cases where cells are sorted, they may do so by methods that allow enrichment of the desired cells, such as by collecting the desired cells upon exposure to one or more substrates that are able to specifically bind the cells. For example, one may utilize separation of the desired cells using an antibody on a substrate (such as a bead, particle, plate, gel matrix, and so forth), wherein the antibody may directly or indirectly bind the cells. In specific embodiments, magnetic separation may be employed.

III. Genetic Modification of NKT Cells

In particular embodiments, the NKT cells are genetically modified prior to delivery to an individual in need thereof. NKT cells are usually modified after TCR-stimulation and co-stimulation; in particular embodiments the genetic modification occurs within 1, 2, 3, 4, 5, or more days after stimulation (and this may depend on the type of transduction used; for example with retroviral vectors it is within 2 days).

The genetic modification of the NKT cells can occur by the hand of man, and in particular embodiments the genetic modification renders the cells able to specifically target one or more cancer cells, such as cancer cells that express a particular antigen, for example. In specific embodiments, the modification provides the NKT cells with a particular non-natural receptor for a certain cancer antigen. The receptor may be of any kind, but in specific embodiments the receptor is a T-cell receptor or a chimeric antigen receptor, for example. In some cases, the chimeric antigen receptor is for CD19, CD22, CD30, GD2, GPC3, CSPG4, HER2, CEA, Mesothelin, etc.

T-cell receptor for MHC/peptide complexes from non-mutated tumor-associated antigens (e.g. Survivin, MYCN, NY-ESO1, MAGE, PRAME, WT1, etc) or patient-specific mutated tumor antigens revealed by sequencing of tumor DNA.

In some cases, the NKT cells are modified to express a CAR. Genetic engineering of the NKT cells to express tumor-directed chimeric antigen receptors (CAR) can produce antitumor effector cells that bypass tumor immune escape mechanisms that are due to abnormalities in protein-antigen processing and presentation. Moreover, these transgenic receptors can be directed to tumor-associated antigens that are not protein-derived. In certain embodiments of the disclosure there are NKT cells that are modified to comprise at least a CAR. In specific aspects, a particular NKT cell comprises expression of two or more CARs.

The present disclosure includes NKT cells that express an artificial T cell receptor referred to as a CAR (that also may be called chimeric T cell receptors or chimeric immunoreceptors). In embodiments of the disclosure it is specific for a cancer antigen. The CAR generally may include an ectodomain, transmembrane domain, and endodomain. It may be first generation, second generation, or third generation, in specific embodiments.

In particular cases, NKT cells include a CAR that is chimeric, non-natural, engineered at least in part by the hand of man, and directed to a particular cancer antigen of interest. In particular cases, the engineered CAR has one, two, three, four, or more components, and in some embodiments the one or more components facilitate targeting or binding of the NKT cell to the cancer antigen-comprising cancer cell. In specific embodiments, the CAR comprises an antibody for the cancer antigen, part or all of a cytoplasmic signaling domain, and/or part or all of one or more co-stimulatory molecules, for example endodomains of co-stimulatory molecules. In specific embodiments, the antibody is a single-chain variable fragment (scFv). In certain aspects the antibody is directed at cancer antigens on the cell surface of cancer cells that express an antigen of interest, for example. In certain embodiments, a cytoplasmic signaling domain, such as those derived from the T cell receptor ζ-chain, is employed as at least part of the chimeric receptor in order to produce stimulatory signals for NKT cell proliferation and effector function following engagement of the chimeric receptor with the target antigen. Examples would include, but are not limited to, endodomains from co-stimulatory molecules such as CD27, CD28, 4-1BB, and OX40 or the signaling components of cytokine receptors such as IL7 and IL15. In particular embodiments, co-stimulatory molecules are employed to enhance the activation, proliferation, and cytotoxicity of the NKT cells produced by the CAR after antigen engagement. In specific embodiments, the co-stimulatory molecules are CD28, OX40, and 4-1BB.

In general, an ectodomain of the CAR encompasses a signal peptide, antigen recognition domain, and a spacer that links the antigen recognition domain to the transmembrane domain. The antigen recognition domain generally will comprise a single chain variable fragment (scFv) specific for a particular cancer antigen. However, in cases wherein there are two or more CARs in the same cell, the second CAR may comprise an scFv specific for another particular antigens. Examples of cancer antigens include any one of Melanoma-associated antigen (MAGE), Preferentially expressed antigen of melanoma (PRAME), CD19, CD20, CD22, κ-light chain, CD30, CD33, CD123, CD38, CD138, ROR1, ErbB2, ErbB3/4, EGFr vIII, carcinoembryonic antigen, EGP2, EGP40, HER2, mesothelin, TAG72, PSMA, NKG2D ligands, B7-H6, IL-13 receptor a2, MUC1, MUC16, CA9, GD2, GD3, HMW-MAA, CD171, Lewis Y, G250/CAIX, HLA-AI MAGE Al, HLA-A2 NY-ESO-1, PSC1, folate receptor-a, CD44v6, CD44v7/8, 8H9, NCAM, VEGF receptors, 5T4, Fetal AchR, NKG2D ligands, or CD44v6, for example.

Examples of hinge regions for the ectodomain include the CH2CH3 region of immunoglobulin, the hinge region from IgGl, and portions of CD3. The transmembrane region may be of any kind, although in some cases it is CD28.

In general, the endodomain of the CAR of the disclosure is utilized for signal transmission in the cell after antigen recognition and cluster of the receptors. The most commonly used endodomain component is CD3-zeta that contains 3 ITAMs and that transmits an activation signal to the T cell after the antigen is bound. In some embodiments, additional co-stimulatory signaling is utilized, such as CD3-zeta in combination with CD28, 4-1BB, and/or OX40.

IV. Cells Generally

Cells of the disclosure include both CD62L-positive NKT cells that have been co-stimulated by one or more costimulatory agents as well as the particular costimulatory agent that itself is an artificial antigen presenting cell (which may be referred to as a non-natural cell that has antigen presenting cell activity). In some embodiments, there is as a composition of matter, an artificial antigen presenting cell that is a non-natural cell expressing CD1d and that expresses one or more ligands of one or more costimulatory receptors.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, a "host cell" can refer to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells used in the disclosure are eukaryotic, including mammalian, although prokaryotic cells may be employed for manipulation in recombinant engineering of vectors or DNA to integrate into the vectors. The cells are particularly human, but can be associated with any animal of interest, particularly domesticated animals, such as equine, bovine, murine, ovine, canine, feline, etc. for use in their respective animal.

The cells can be autologous cells, syngeneic cells, allogenic cells and even in some cases, xenogeneic cells, such as in relation to the individual that is receiving the cells. The cells may be modified by changing the major histocompatibility complex ("MHC") profile, by inactivating 132-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

Expression vectors that encode a CAR can be introduced into the cells as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In many situations one may wish to be able to kill the modified cells, where one wishes to terminate the treatment, the cells become neoplastic, in research where the absence of the cells after their presence is of interest, or other event. For this purpose one can provide for the expression of certain gene products in which one can kill the modified cells under controlled conditions. Suicide gene products, such as caspase 9, are examples of such products.

By way of illustration, cancer patients or patients susceptible to cancer or suspected of having cancer may be treated as follows. Cells modified as described herein may be administered to the patient and retained for extended periods of time. The individual may receive one or more administrations of the cells. The cell(s) would be modified and provided to the individual in need thereof.

V. Polynucleotides

The present disclosure also encompasses a composition comprising a nucleic acid sequence encoding an antigen-specific CAR as defined herein and cells harboring the nucleic acid sequence. The nucleic acid molecule is a recombinant nucleic acid molecule, in particular aspects and may be synthetic. It may comprise DNA, RNA as well as PNA (peptide nucleic acid) and it may be a hybrid thereof.

Furthermore, it is envisaged for further purposes that nucleic acid molecules may contain, for example, thioester bonds and/or nucleotide analogues. The modifications may be useful for the stabilization of the nucleic acid molecule against endo- and/or exonucleases in the cell. The nucleic acid molecules may be transcribed by an appropriate vector comprising a chimeric gene that allows for the transcription of said nucleic acid molecule in the cell. In this respect, it is also to be understood that such polynucleotides can be used for "gene targeting" or "gene therapeutic" approaches. In another embodiment the nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

The nucleic acid molecule(s) may be a recombinantly produced chimeric nucleic acid molecule comprising any of the aforementioned nucleic acid molecules either alone or in combination. In specific aspects, the nucleic acid molecule is part of a vector.

The present disclosure therefore also relates to a composition comprising a vector comprising the nucleic acid molecule described in the present disclosure.

Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994). Alternatively, the polynucleotides and vectors of the disclosure can be reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In specific embodiments, there is a vector that comprises a nucleic acid sequence that is a regulatory sequence operably linked to the nucleic acid sequence encoding an antigen-specific CAR defined herein. Such regulatory sequences (control elements) are known to the artisan and may include a promoter, a splice cassette, translation initiation codon, translation and insertion site for introducing an insert into the vector. In specific embodiments, the nucleic acid molecule is operatively linked to said expression control sequences allowing expression in eukaryotic or prokaryotic cells.

It is envisaged that a vector is an expression vector comprising the nucleic acid molecule encoding an antigen-specific CAR as defined herein. In specific aspects, the vector is a viral vector, such as a lentiviral vector. Lentiviral vectors are commercially available, including from Clontech (Mountain View, Calif.) or GeneCopoeia (Rockville, Md.), for example.

The term "regulatory sequence" refers to DNA sequences that are necessary to effect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is an expression vector, in certain embodiments. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in E. coli, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements that are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art. The leader sequence (s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pEF-Neo, pCDM8, pRc/CMV, pcDNA1, pcDNA3 (Invitrogen), pEF-DHFR and pEF-ADA, (Raum et al. Cancer Immunol Immunother (2001) 50(3), 141-150) or pSPORT1 (GIBCO BRL).

In some embodiments, the expression control sequences are eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the disclosure may follow. In particular embodiments, one or more encodable sequences are regulated by expression control sequences that are responsive to hypoxic environments.

Additional regulatory elements may include transcriptional as well as translational enhancers. Advantageously, the above-described vectors of the disclosure comprises a selectable and/or scorable marker. Selectable marker genes useful for the selection of transformed cells are well known to those skilled in the art and comprise, for example, antimetabolite resistance as the basis of selection for dhfr, which confers resistance to methotrexate (Reiss, Plant Physiol. (Life-Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used in a cell, alone, or as part of a vector to express the encoded polypeptide in cells. The nucleic acid molecules or vectors containing the DNA sequence(s) encoding any one of the specific CAR constructs is introduced into the cells that in turn produce the polypeptide of interest. The recited nucleic acid molecules and vectors may be designed for direct introduction or for introduction via liposomes, or viral vectors (e.g., adenoviral, retroviral) into a cell.

In accordance with the above, the present disclosure relates to methods to derive vectors, particularly plasmids, cosmids, viruses and bacteriophages used conventionally in genetic engineering that comprise a nucleic acid molecule encoding the polypeptide sequence of an antigen-specific CAR defined herein. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods which are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

XII. Pharmaceutical Compositions

In accordance with this disclosure, the term "pharmaceutical composition" relates to a composition for administration to an individual. In specific aspects of the disclosure, the pharmaceutical composition comprises a plurality of NKT cells. In a preferred embodiment, the pharmaceutical composition comprises a composition for parenteral, transdermal, intraluminal, intra-arterial, intrathecal or intravenous administration or for direct injection into a cancer. It is in particular envisaged that said pharmaceutical composition is administered to the individual via infusion or injection. Administration of the suitable compositions may be effected by different ways, e.g., by intravenous, subcutaneous, intraperitoneal, intramuscular, topical or intradermal administration.

The pharmaceutical composition of the present disclosure may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. CAR-modified NKT may be administered via intravenous infusion. Doses can range from $1\times10^7/m^2$ to $2\times10^8/m^2$, and in specific embodiments up to $10^9$ cells may be utilized.

The compositions of the disclosure may be administered locally or systemically. Administration will generally be parenteral, e.g., intravenous; DNA may also be administered directly to the target site, e.g., by biolistic delivery to an internal or external target site or by catheter to a site in an artery. In a preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. It is envisaged that the pharmaceutical composition of the disclosure might comprise, in addition to the CAR constructs or nucleic acid molecules or vectors encoding the same (as described in this disclosure), further biologically active agents, depending on the intended use of the pharmaceutical composition.

XII. Therapeutic Uses of NKT Cells

By way of illustration, cancer patients or patients susceptible to cancer or suspected of having cancer may be treated as described herein. NKT cells modified as described herein may be administered to the individual and retained for extended periods of time. The individual may receive one or more administrations of the cells. In some embodiments, the genetically modified cells are encapsulated to inhibit immune recognition and placed at the site of the tumor.

In various embodiments the expression constructs, nucleic acid sequences, vectors, host cells and/or pharmaceutical compositions comprising the same are used for the prevention, treatment or amelioration of a cancerous disease, such as a tumorous disease. In particular embodiments, the pharmaceutical composition of the present disclosure may be particularly useful in preventing, ameliorating and/or treating cancer, including cancer having solid tumors, for example.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In particular embodiments, the present disclosure contemplates, in part, cells harboring expression constructs, nucleic acid molecules and/or vectors that can administered either alone or in any combination with another therapy, and in at least some aspects, together with a pharmaceutically acceptable carrier or excipient. In certain embodiments, prior to administration of the cells, said nucleic acid molecules or vectors may be stably integrated into the genome of the cells. In specific embodiments, viral vectors may be used that are specific for certain cells or tissues and persist in said cells. Suitable pharmaceutical carriers and excipients are well known in the art. The compositions prepared according to the disclosure can be used for the prevention or treatment or delaying the above identified diseases.

Furthermore, the disclosure relates to a method for the prevention, treatment or amelioration of a cancerous (including tumorous) disease comprising the step of administering to a subject in need thereof an effective amount of cells harboring an antigen recognition moiety molecule and a chemotherapy resistance molecule, nucleic acid sequence that encodes them, vector(s) that encodes them, as contemplated herein and/or produced by a process as contemplated herein.

Possible indications for administration of the composition(s) of the exemplary modified immune cells are cancerous diseases, including tumorous diseases, including breast, prostate, lung, and colon cancers or epithelial cancers/carcinomas such as MM, breast cancer, colon cancer, prostate cancer, head and neck cancer, skin cancer, cancers of the genito-urinary tract, e.g. ovarian cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivary glands and cancer of the thyroid gland, neuroblastoma, medulloblastoma, glioblastoma, hematopoetic malignancies, and so forth. Exemplary indications for administration of the composition(s) of cells are cancerous diseases, including any malignancies that express a particular antigen, for example. In addition, it includes malignancies that aberrantly express other tumor antigens and those may also be targeted. The administration of the composition(s) of the disclosure is useful for all stages and types of cancer, including for minimal residual disease, early cancer, advanced cancer, and/or metastatic cancer and/or refractory cancer, for example.

The disclosure further encompasses co-administration protocols with other compounds, e.g. bispecific antibody constructs, targeted toxins or other compounds, which act via immune cells. The clinical regimen for co-administration of the inventive compound(s) may encompass co-administration at the same time, before and/or after the administration of the other component. Particular combination therapies include chemotherapy, radiation, surgery, hormone therapy, or other types of immunotherapy.

Embodiments relate to a kit comprising one or more NKT cells as described herein, a nucleic acid sequence as described herein, a vector as described herein and/or a host as described herein. It is also contemplated that the kit of this disclosure comprises a pharmaceutical composition as described herein above, either alone or in combination with further medicaments to be administered to an individual in need of medical treatment or intervention.

The NKT cells that have been modified with the construct(s) are then grown in culture under selective conditions and cells that are selected as having the construct may then be expanded and further analyzed, using, for example; the polymerase chain reaction for determining the presence of the construct(s) in the host cells. Once the modified host cells have been identified, they may then be used as planned, e.g., expanded in culture or introduced into a host organism.

Depending upon the nature of the cells, the cells may be introduced into a host organism, e.g., a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

The cells may be administered as desired. Depending upon the response desired, the manner of administration, the life of the cells, the number of cells present, various protocols may be employed. The number of administrations will depend upon the factors described above at least in part.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

VI. Kits of the Disclosure

Any of the compositions described herein may be comprised in a kit. In a non-limiting example, cells or reagents to manipulate cells may be comprised in a kit. In certain embodiments, NKT cells or a population of cells that comprises NKT cells may be comprised in a kit. Such a kit may or may not have one or more reagents for manipulation of cells. Such reagents include small molecules, proteins, nucleic acids, antibodies, buffers, primers, nucleotides, salts, and/or a combination thereof, for example. Nucleotides that encode one or more cytokines, or cytokines themselves, may be included in the kit. Proteins, such as cytokines or antibodies, including agonistic monoclonal antibodies, may be included in the kit. Substrates that comprise the antibodies, or naked substrates themselves, may be included in the kit, and in some embodiments reagents to generate antibody-bearing substrates are included in the kit. The substrates may be of any kind including a bead or plate. Cells that comprise antigen presenting cell activity or reagents to generate same may be included in the kit. Nucleotides that encode chimeric antigen receptors or T-cell receptors may be included in the kit, including reagents to generate same.

In particular aspects, the kit comprises the cell therapy of the disclosure and also another cancer therapy. In some cases, the kit, in addition to the cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

The kits may comprise suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also may generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The Identification of the NKT-Cell Subset Responsible for in Vivo Persistence and Therapeutic Activity and Defining the Conditions Required for Propagation of this Subset in Culture The adoptive transfer of invariant Natural Killer T cells (NKTs) is being developed as a promising therapeutic modality for immunotherapy of cancer, autoimmunity, and other diseases. Because NKT-cell frequency is low in human peripheral blood, such therapies require extensive ex vivo expansion of primary NKTs while preserving their longevity and function. However, cellular and molecular mechanisms responsible for the maintenance of NKTs either in vivo or ex vivo remain largely unknown. Here it is demonstrated that antigen-induced in vitro expansion of primary human NKTs is associated with the progressive accumulation of CD62L-positive subset in all 5 examined individuals regardless of the initial frequency of that subset. Following magnetic sorting of NKTs into CD62L-positive and CD62L-negative subsets, only CD62L-positive cells survived and proliferated in response to TCR-stimulation whereas about 90% of CD62L-negative cells underwent apoptosis within 3 days. Moreover, CD62L-positive NKTs persisted 5 times longer than CD62L-negative ones after adoptive transfer to NSG mice. Importantly, CD62L-positive NKTs had much higher therapeutic activity and significantly prolonged survival of mice in a xenogenic lymphoma model. Proliferating CD62L-positive cells downregulated or maintained CD62L expression when they were activated via TCR alone or with co-stimulatory receptors, respectively. In particular, certain combinations of agonistic mAbs for CD3, CD28, and/or 4-1BB enable stable CD62L expression on in vitro stimulated NKTs that is associated with the maximal rate of their expansion and subsequent in vivo persistence. Therefore, the results reveal previously unanticipated functional hierarchy in human NKTs that can be exploited for their effective ex vivo expansion for cell therapy applications.

Thus, identified herein is CD62L as a marker of human NKT cells with high proliferative potential and superior therapeutic activity. In vitro stimulation conditions were determined that prevent CD62L downregulation on NKTs during ex vivo expansion that is useful for the generation of NKT-cell products with high therapeutic activity.

Example 2

CD62L+ NKT Cells have Superior in Vivo Persistence and Anti-Tumor Activity

Figure 1B:
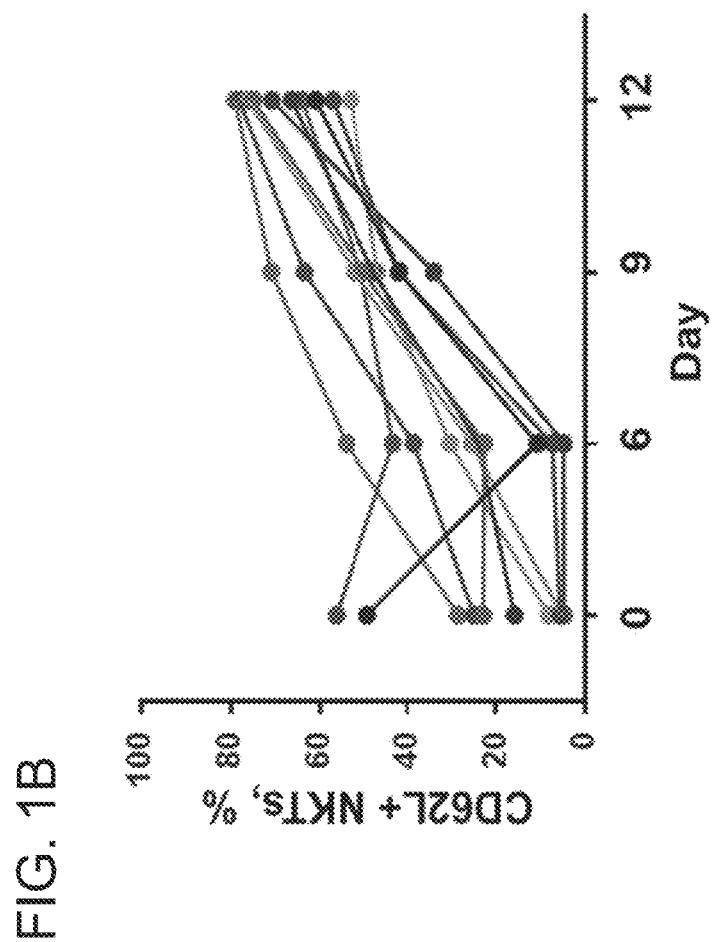
Figure 1C:
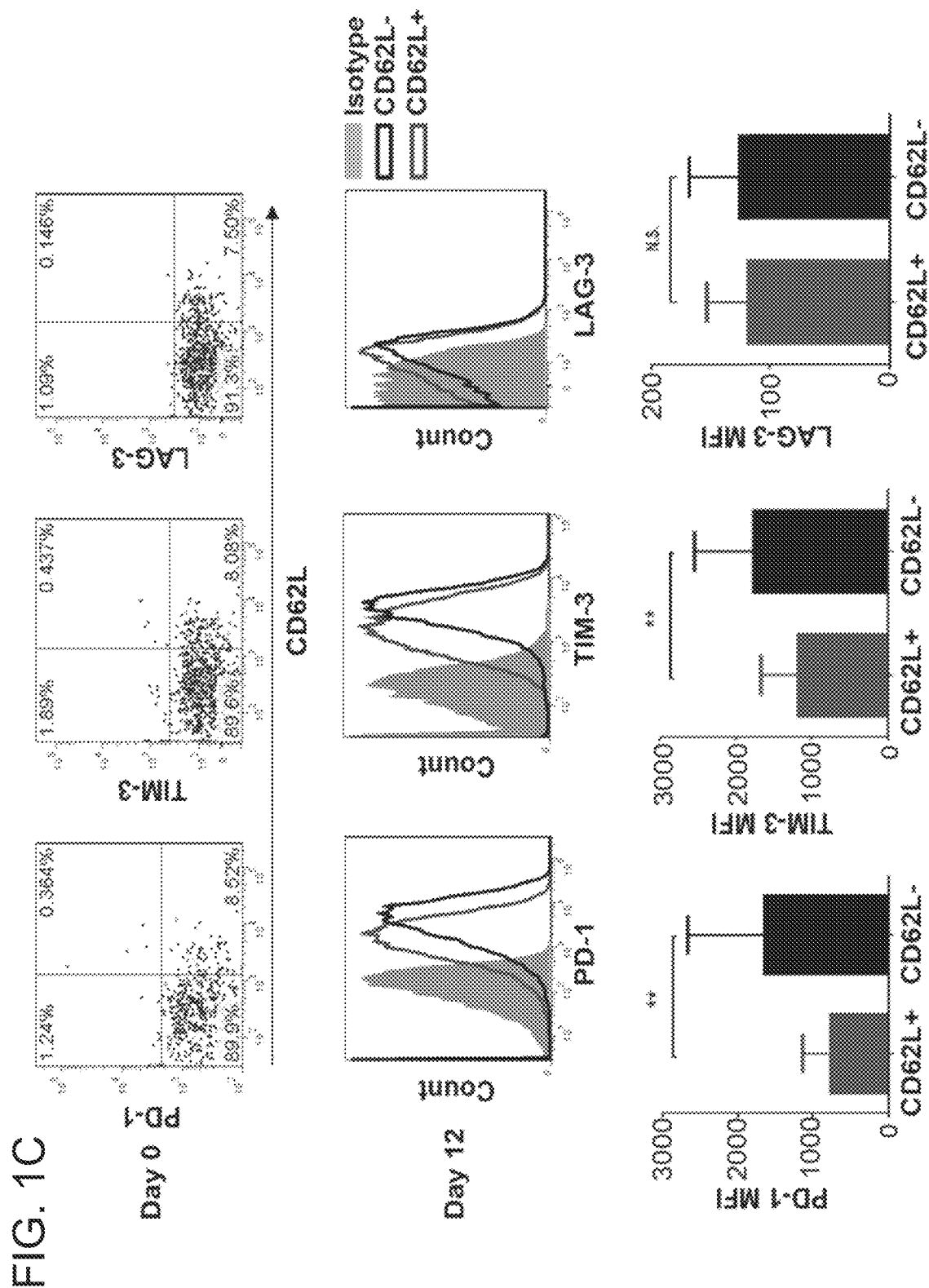
Figure 1D:
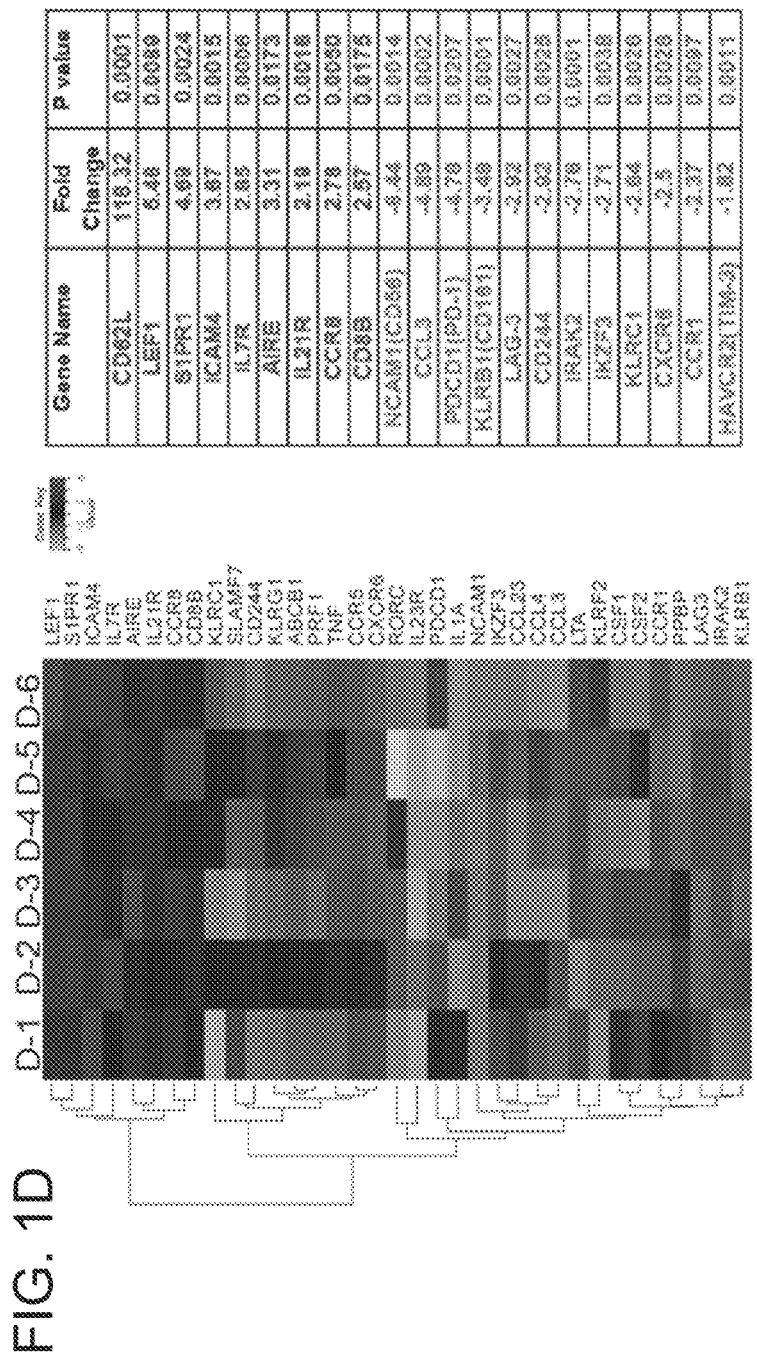
Figure 5A:
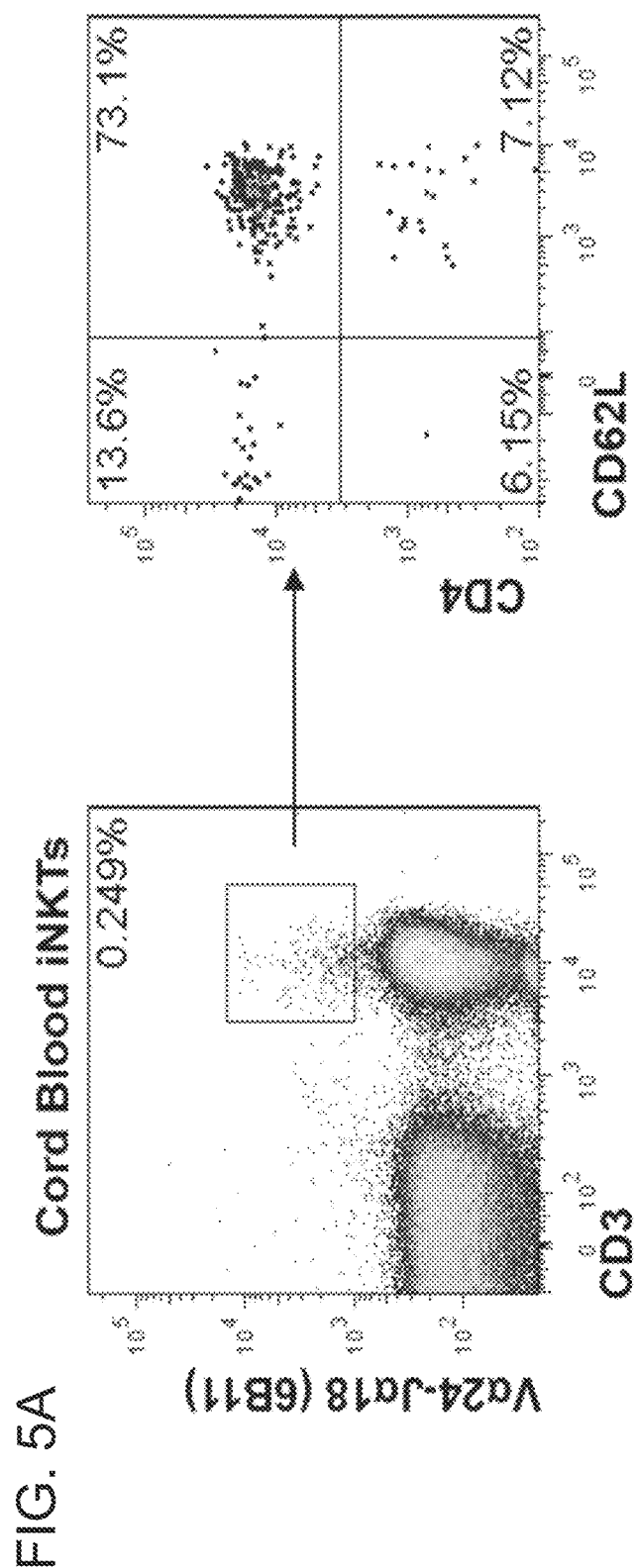
Figure 5B:
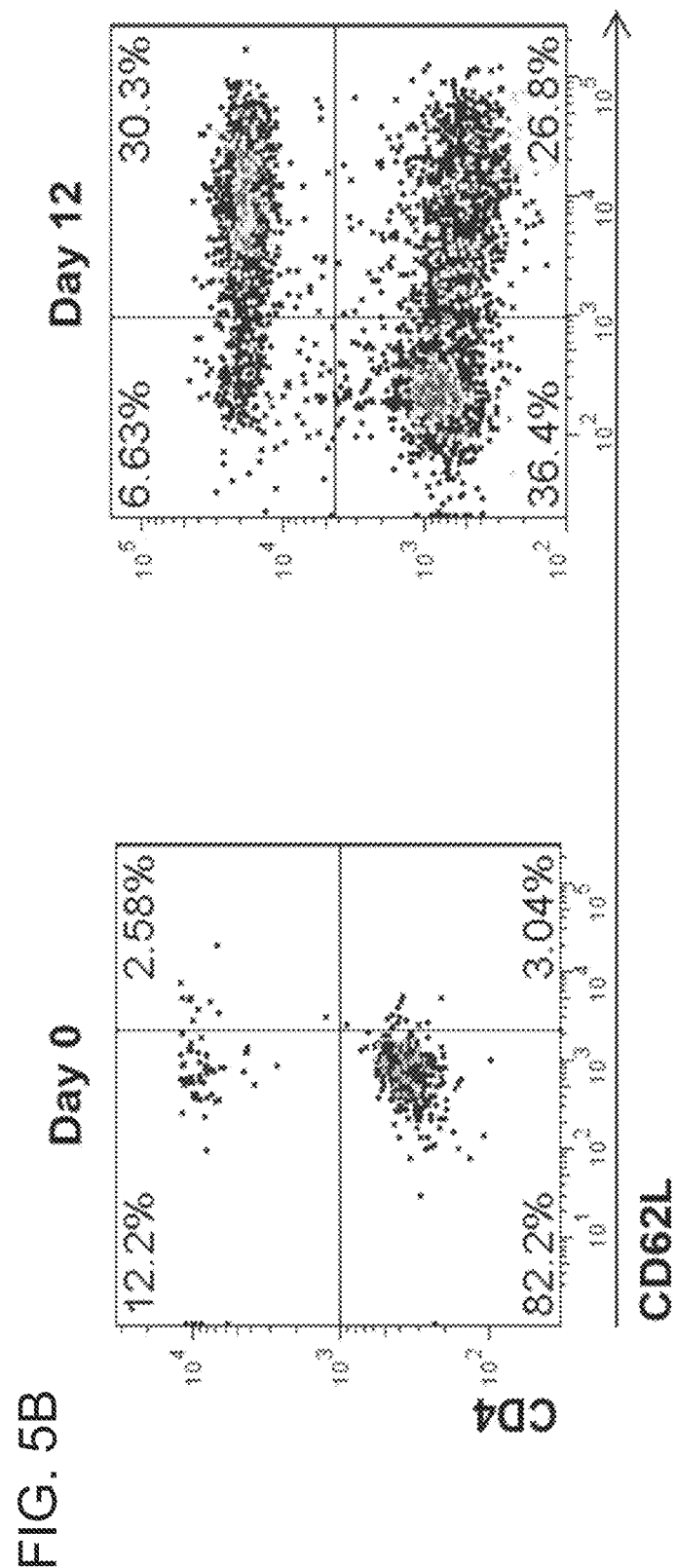
Figure 5C:
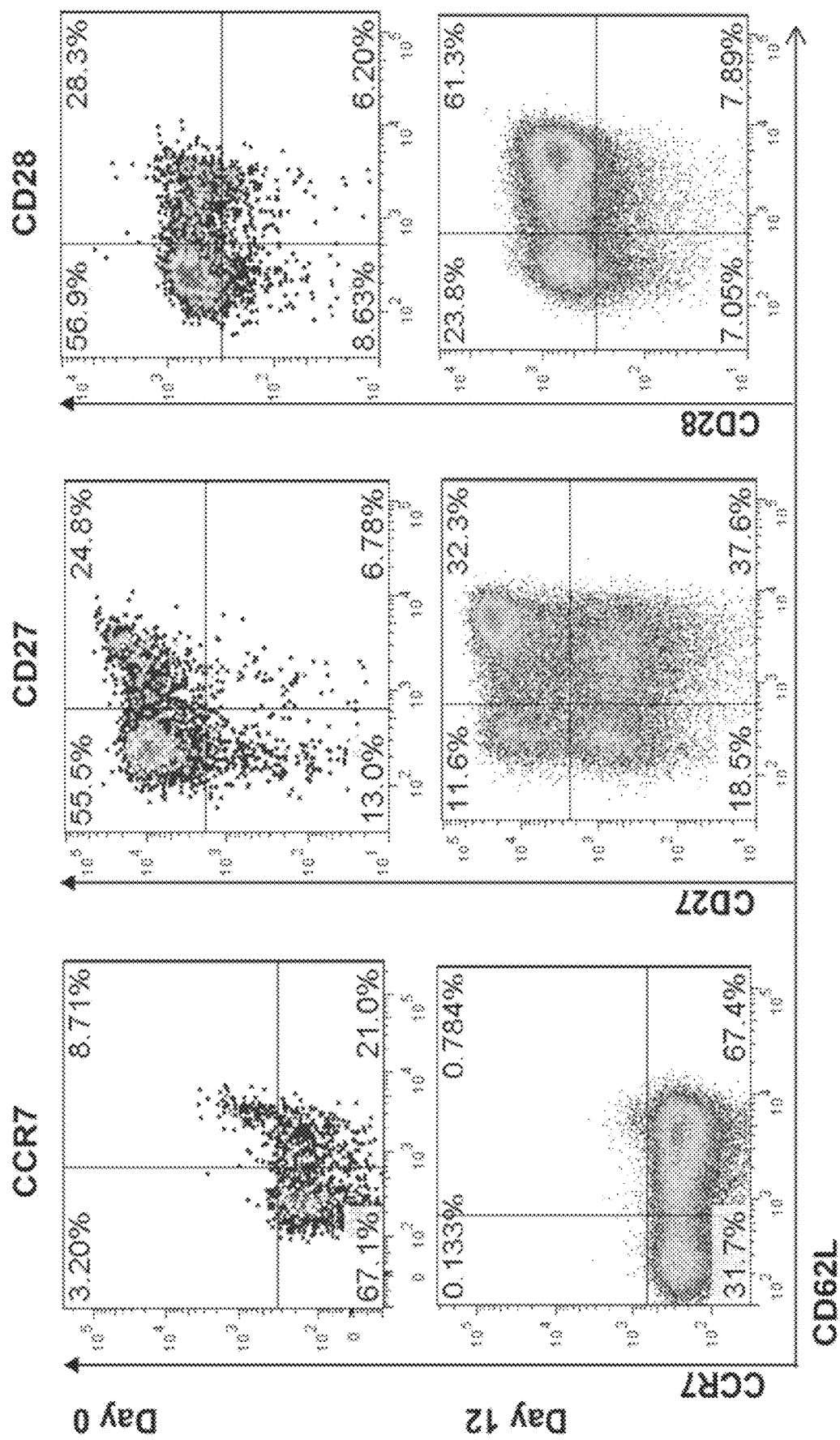
Figure 5D:
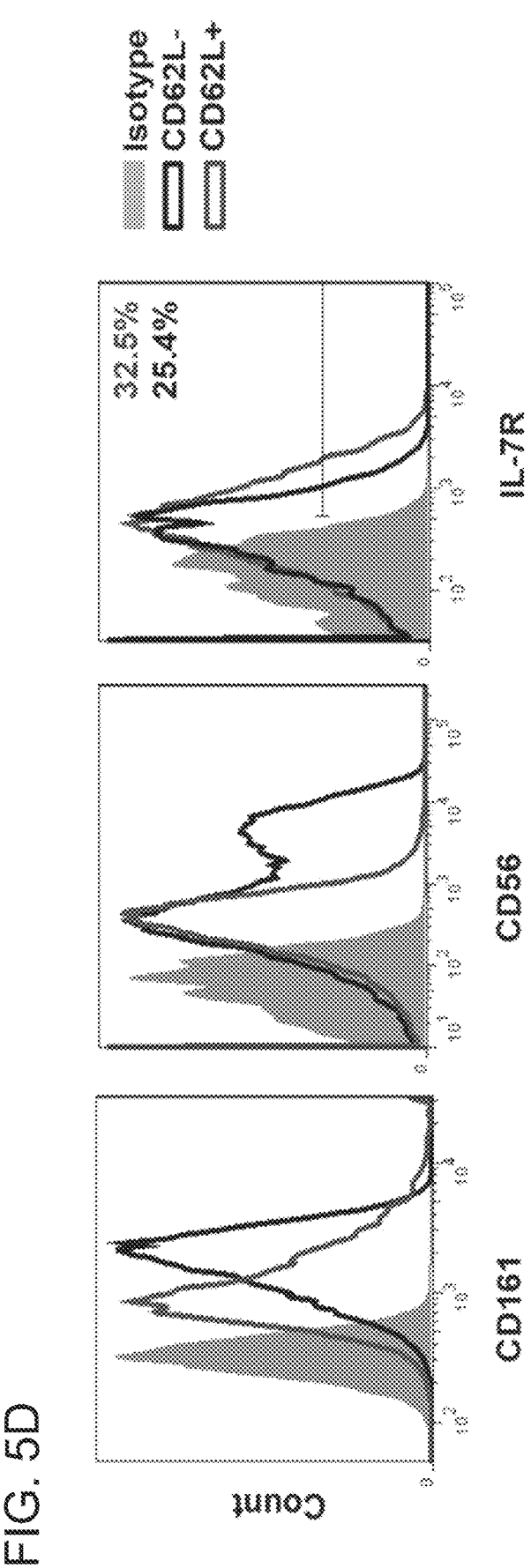
Figure 6A:
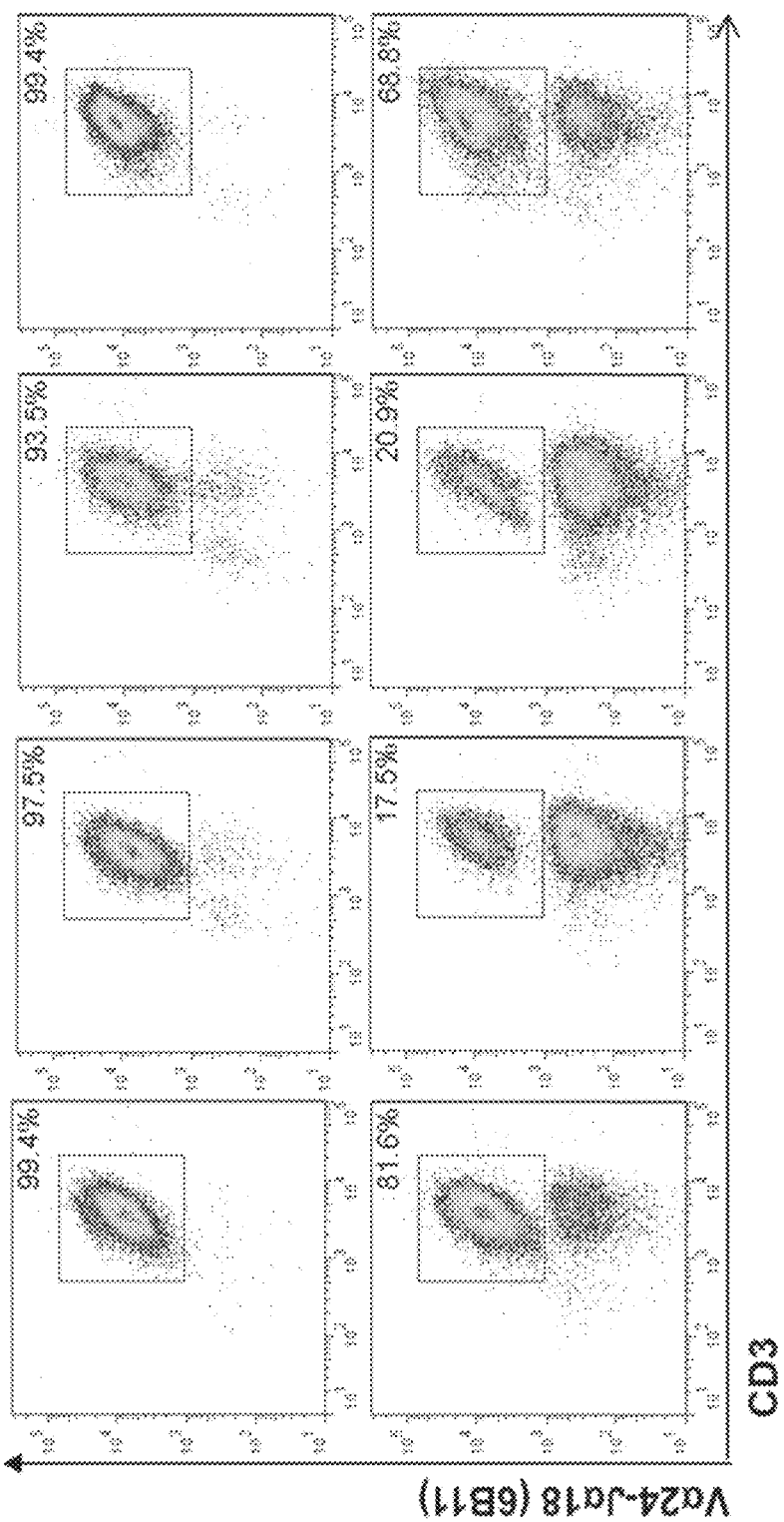
FIGS. 6A-6B. The comparison of NKT-cell purity and absolute numbers after expansion with CD3/CD28 agonistic mAbs vs. αGalCer-pulsed irradiated PBMC. NKTs were isolated from four PBMCs. Half of them were stimulated using autologous irradiated PBMC pulsed with αGalCer, another half were stimulated with CD3/CD28 mAb-coated plate. In both cases, cells were propagated in culture with the IL-2 (200 U/ml) added every other day. At day 12, cultures were analyzed for: (6A) NKT-cell purity was determined by flow cytometry as percent cells expressing CD3 and iTCRα. (6B) NKT-cell absolute cell count was performed using trypan blue exclusion assay in triplicates. * $P<0.05$, data were analyzed after Log(2) transformation using paired t test.
Figure 6B:
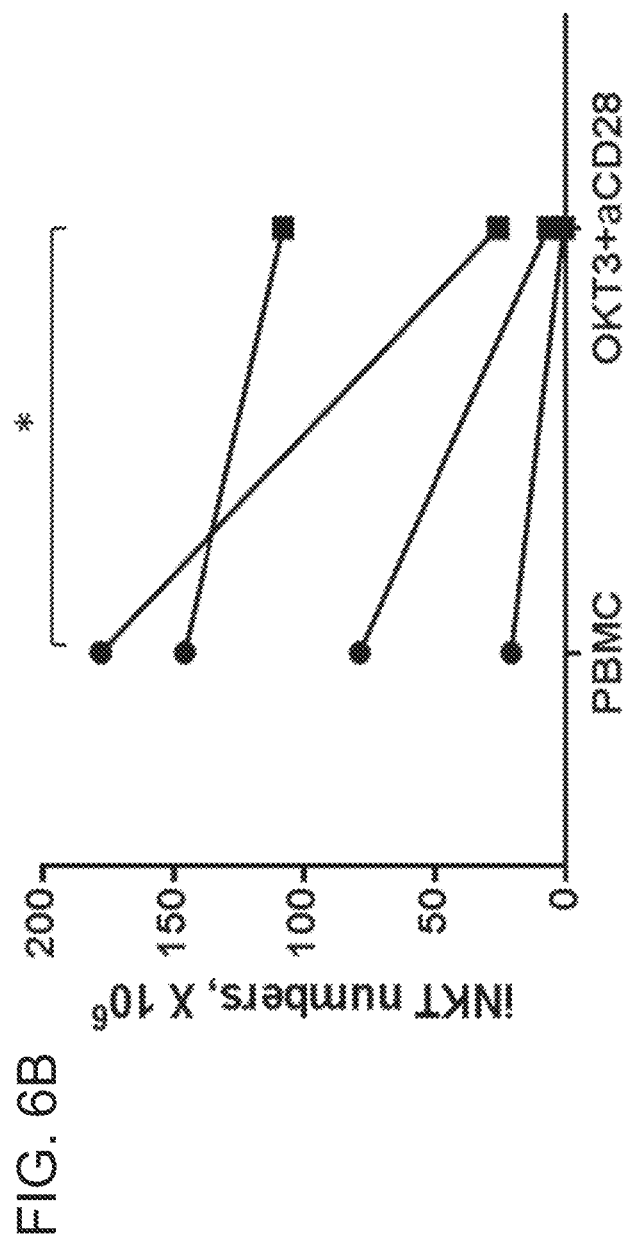

CD62L+ cells accumulate in culture upon antigenic stimulation of primary NKTs. Previous studies that compared the phenotype of human NKTs in adult peripheral blood with that in cord blood observed much higher proportions of CD4+ and CD62L+ NKTs in neonates (Baev et al., 2004; D'Andrea et al., 2000; Eger et al., 2006) (FIG. 5A). The prevalence of CD4+CD62L+ NKTs in cord blood suggests that the expression of CD4 or/and CD62L marks a subset of NKTs that has superior developmental potential and could support ex vivo expansion of NKTs for therapeutic applications. To test this embodiment, immunophenotyping was performed of primary NKTs immediately after isolation from peripheral blood and at different time intervals in culture after stimulation with αGalCer, which consistently produced higher frequency and absolute numbers of NKTs compared to the use of a T-cell expansion protocol based on CD3/CD28 stimulation (FIG. 6). Despite a notable inter-individual variability of CD62L expression in freshly isolated NKTs, there was a striking accumulation of CD62L+ fraction of NKTs from 33.63%±27.62% in freshly isolated NKTs to 69.92%±10.57% on day 12 of the culture (P<0.001, FIGS. 1A, 1B). Although CD62L was more frequently expressed on CD4+ NKTs both before and after culture, the accumulation of CD62L+ cells could not be explained by a preferential expansion of CD4+ NKTs. Indeed, at the end of a 12-day culture, the frequency of CD62L+, CD4+, and CD62L+CD4+ NKTs increased 3.9±1.8, 1.9±0.7, and 3.8±1.9 fold, respectively. Consistent with these results, there was an enrichment of the CD62L+ CD4− subset at day 12 compared to day 0 (FIG. 5B). Further multi-parameter characterization of NKTs showed that CD62L was often co-expressed with CCR7 before culture, but CCR7 expression was progressively lost during culture (FIG. 5C). Nearly all NKTs expressed both CD27 and CD28 before culture. While CD27 was down-regulated in about half of NKTs by day 12 of culture irrespective to CD62L status, CD28 expression remained intact (FIG. 5C). CD62L− cells expressed higher levels of CD161 and CD56 (NK-like differentiation), but a lower level of IL-7Rα (FIG. 5D). While freshly isolated NKTs rarely expressed exhaustion markers (PD-1, LAG-3, or 6 TIM-3) in either the CD62L+ or CD62L− subsets, the CD62L− subset preferentially expressed PD-1 and TIM-3 at day 12 of NKT-cell culture (P=0.0043, 0.0184, FIG. 5C). Moreover, immune-related gene expression analysis (nCounter® platform) of CD62L+ and CD62L− NKTs sorted on day 12 revealed mRNA up-regulation of genes associated with T-cell survival/memory (e.g. LEF1, S1PR1, IL-7Rα, IL21R) in CD62L+ NKTs and with exhaustion/terminal differentiation in CD62L− NKTs (e.g. PD-1, LAG-3, TIM-3, CD244, CD161, CD56, FIG. 1D). The transcription factor lymphoid enhancer factor 1 (LEF1) was the top immune-related gene overexpressed in CD62L+ compared to CD62L− NKTs. Intracellular flow cytometry analysis demonstrated that CD62L+ NKTs uniformly expressed LEF1, whereas a major fraction of CD62L− cells was LEF1-negative. Since LEF1 was recently shown to mediate expansion of murine NKT cell precursors in part via transcriptional activation of GATA3 gene expression (Carr et al., 2015), the level of GATA3 protein was analyzed in human NKTs in relation to LEF1 and CD62L levels. GATA3 expression strongly correlated with the expression of LEF1 and CD62L in human NKTs (FIG. 5E). Of interest, CD62L+ and CD62L− NKTs expressed the same level of PLZF, a transcriptional master regulator of NKT-cell functional differentiation (Cohen et al., 2013). Thus, the CD62L+ subset predominantly accumulates in culture upon antigenic stimulation of primary NKTs and loss of CD62L expression is associated with NK-like terminal differentiation, exhaustion, and down-regulation of proproliferative transcriptional regulators.

Figure 2A:
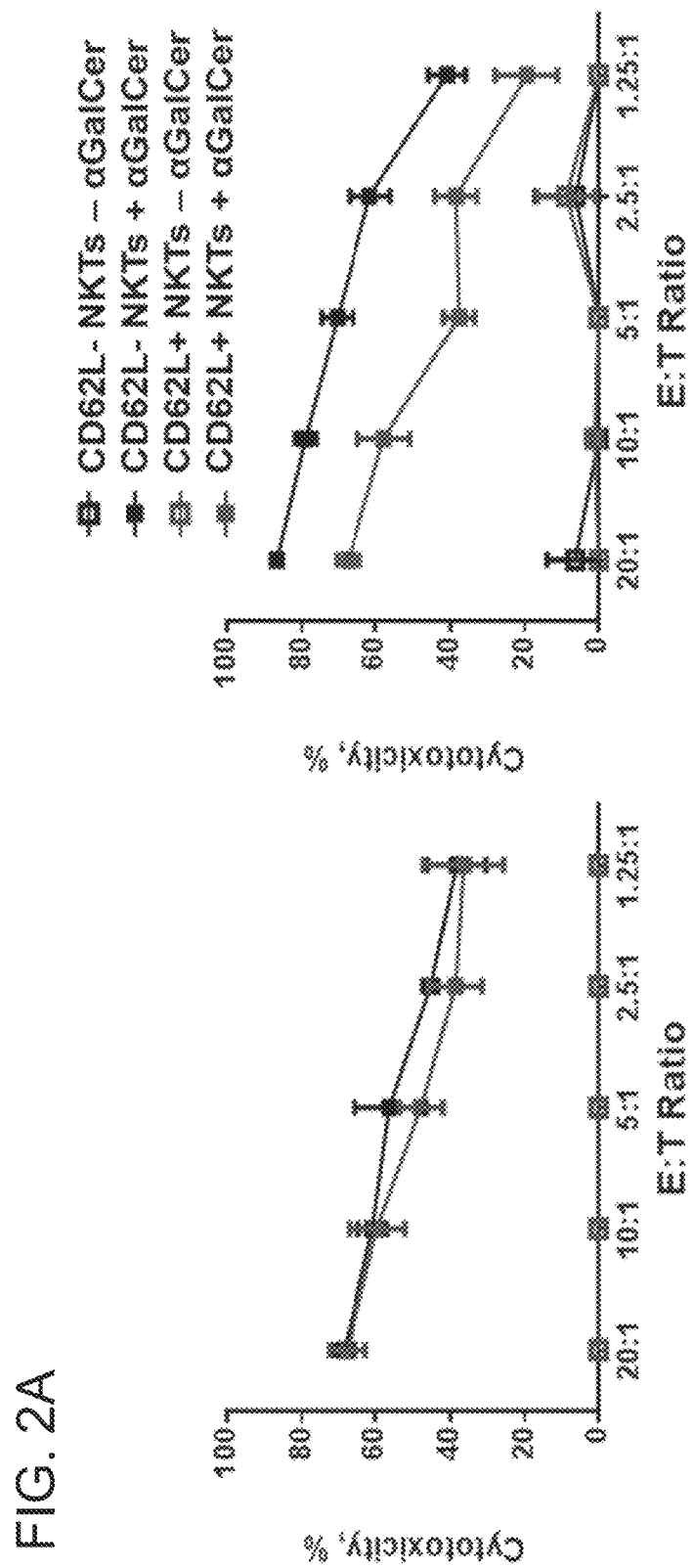
Figure 2B:
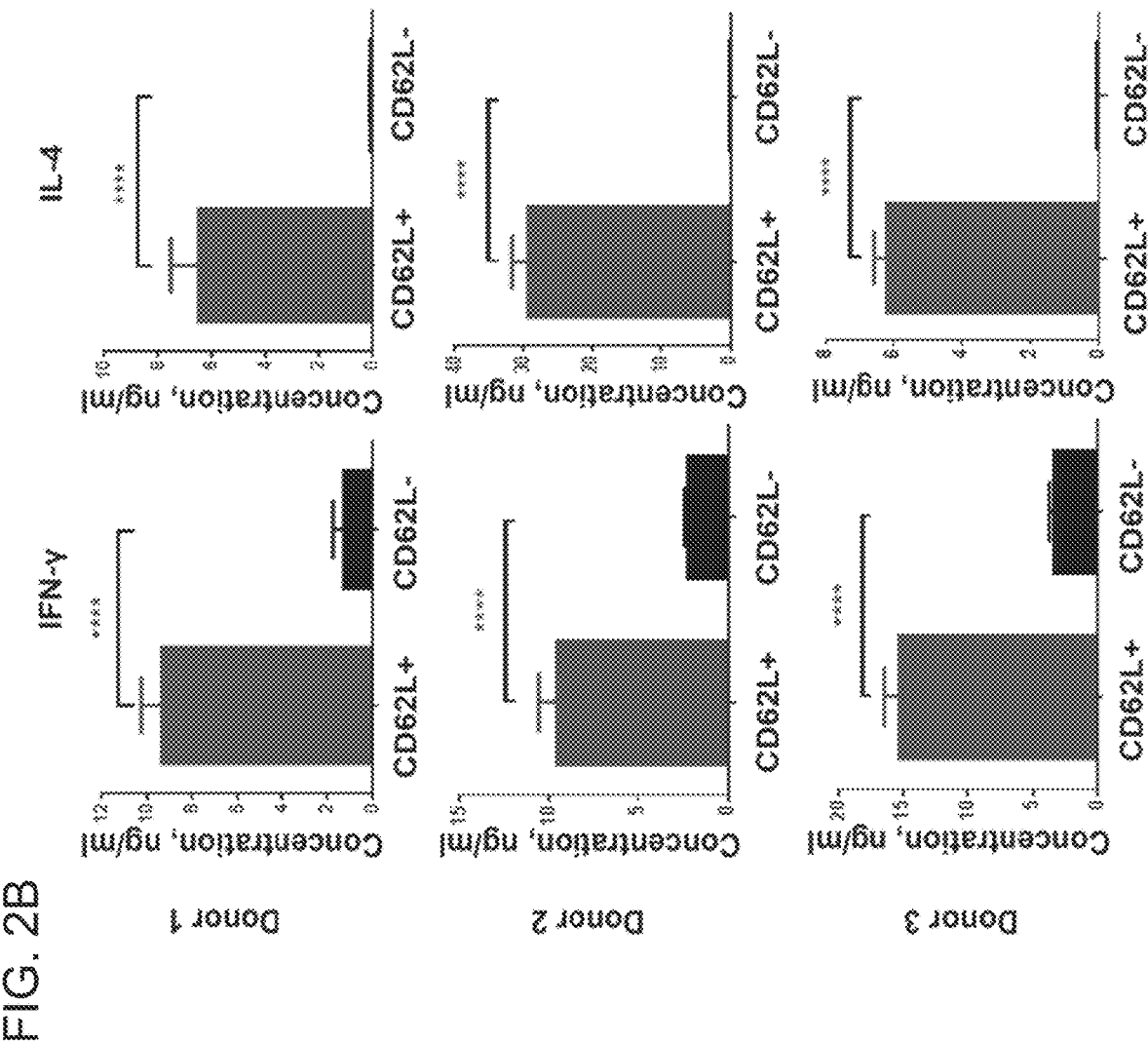

CD62L+ NKTs are Th-0-like cells capable of numeric expansion. Next, NKTs were magnetically sorted from primary culture into CD62L+ and CD62L− subsets and examined their functional properties. FIG. 2A demonstrates that both subsets were either equally cytotoxic (three of six donors) or CD62L− NKTs were more cytotoxic than CD62L+ NKTs (three of six donors) against CD1d+ DAOY medulloblastoma cells when the target cells were pulsed with αGalCer. The analysis of cytokine production in αGalCer-stimulated NKTs revealed much higher levels of both IFN-γ and IL-4 production by CD62L+ compared to CD62L− subsets (P<0.001, FIG. 2B). CD62L+ cells exhibited a Th-0-like polarization (a balanced production of IFN-γ and IL-4, typical of whole population of peripheral blood NKTs) whereas the polarization profile of CD62L− cells could not be determined unambiguously because of the low absolute amounts of each cytokine. Despite strong up-regulation of IL-23R mRNA expression in the CD62L− subset as determined by the nCounter analysis (FIG. 1D, a potential Th17 polarization), neither IL-23R protein expression on the cell surface of NKTs by FACS nor production of IL-17 upon TCR stimulation by ELISA were detected.

Figure 2D:
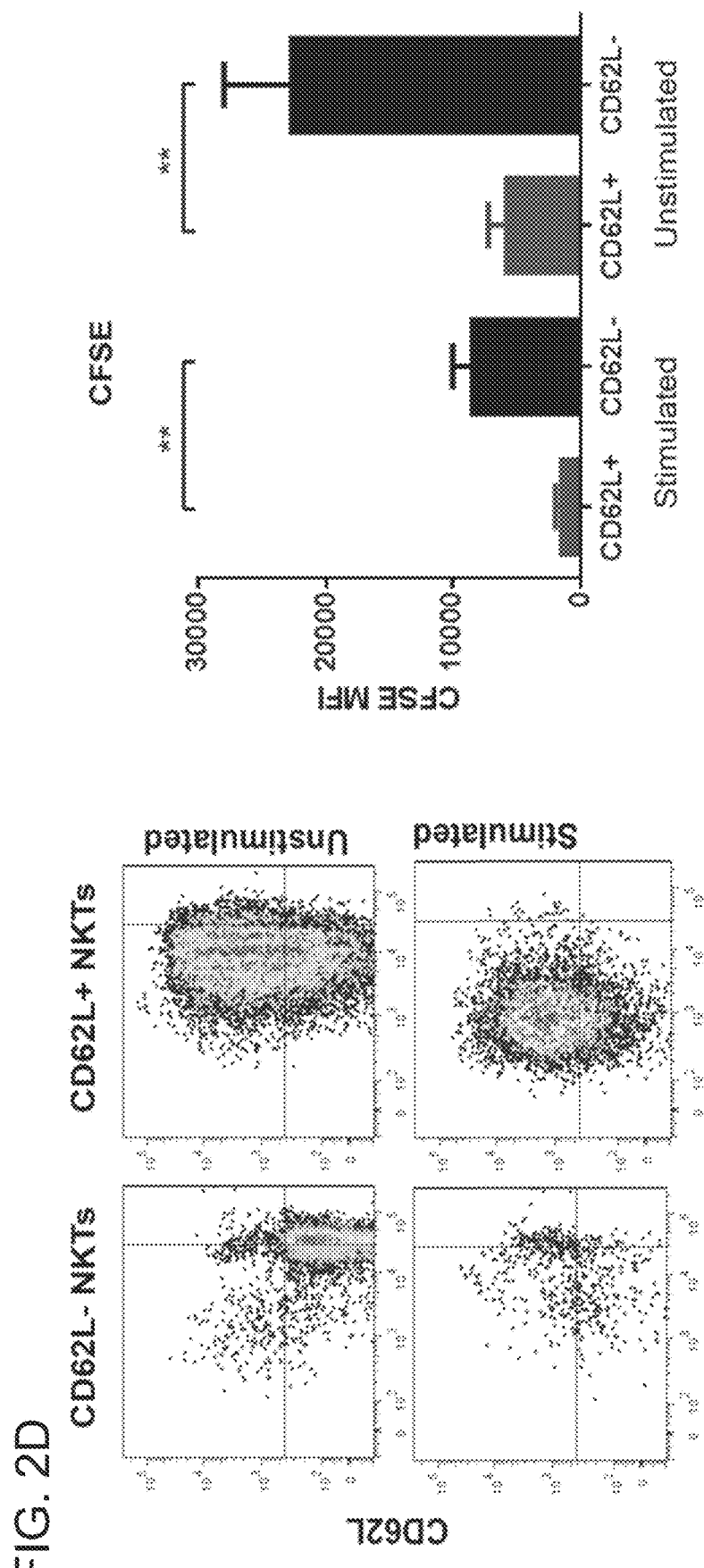
Figure 2E:
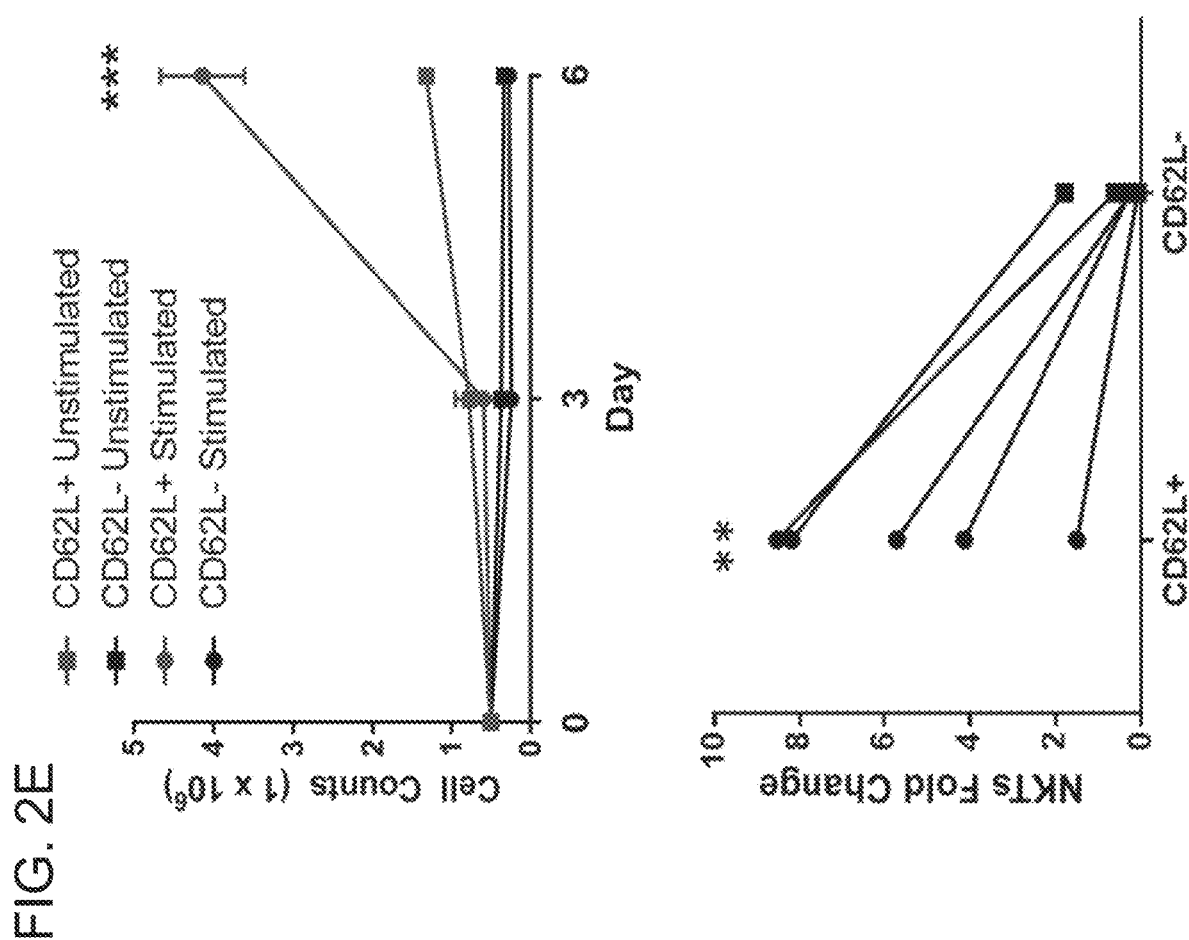

To examine whether the accumulation of CD62L+ NKTs during in vitro expansion is because of their preferential survival or proliferation in response to antigenic stimulation, their rate of cell death and proliferation was measured after stimulation of the sorted cells with antigen-presenting cells that had been pulsed with αGalCer. On day 3 after stimulation, 31%±21% and 74% ±7.5% of CD62L+ and CD62L− NKTs underwent apoptosis, respectively (FIG. 2C). There was a much greater rate of proliferation in CD62L+ vs. CD62L− subsets as measured by CFSE dilution on day 6 (FIG. 2D). Moreover, the majority of cells that survived and proliferated in the CD62L− group expressed CD62L, suggesting that these cells were progenies of a small subset of CD62L+ cells in the original CD62L− fraction. Consistent with these results, there was a striking difference in the numbers of NKTs generated after a 6-day culture of sorted CD62L+ vs. CD62L− NKTs with IL-2 alone or with TCR-stimulation. Indeed, FIG. 2E (upper panel) demonstrates that CD62L+ cells underwent 2.5 and 8 fold numeric expansion with IL-2 alone or with TCR-stimulation, respectively. In contrast, CD62L− NKTs failed to expand in either condition. Although the degree of NKT-cell proliferation in response to antigenic stimulation varied from donor to donor, the CD62L− subset contributed little or nothing to NKT-cell expansion in all five tested donors (FIG. 2E, lower panel). Therefore, CD62L+ NKTs survive and proliferate in response to antigenic stimulation and are responsible for NKT-cell numeric expansion in culture.

Figure 3B:
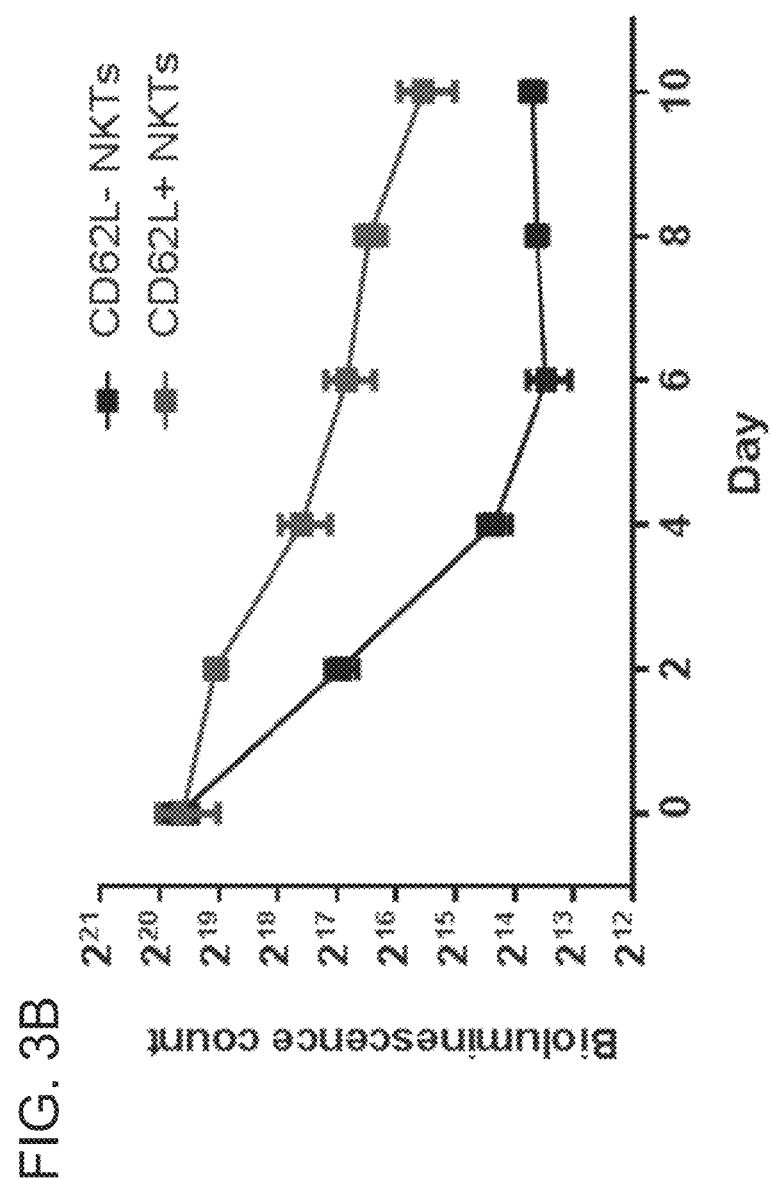
Figure 7A:
FIGS. 7A-7B. NKT-cell transduction with CAR.CD19. (7A) Schematic presentation of CAR.CD19 construct. (7B) NKTs were re-stimulated with autologous PBMC (irradiated with 40 Gy). On day 3 after re-stimulation, 24 well, non-tissue culture plates were coated with retronectin and after washing inoculated with 1 ml of retroviral supernatant containing CAR.CD19. The viral supernatant was then removed and NKTs were added to the wells in complete media and 200 U/ml rhIL-2. NKTs were then magnetically sorted to CD62L+ and CD62L− subsets and CAR.CD19 surface expression was analyzed with 2D3 mAb staining by FACS 12 days after transduction. Shown are FACS plots from a representative of 3 independent experiments.
Figure 7B:
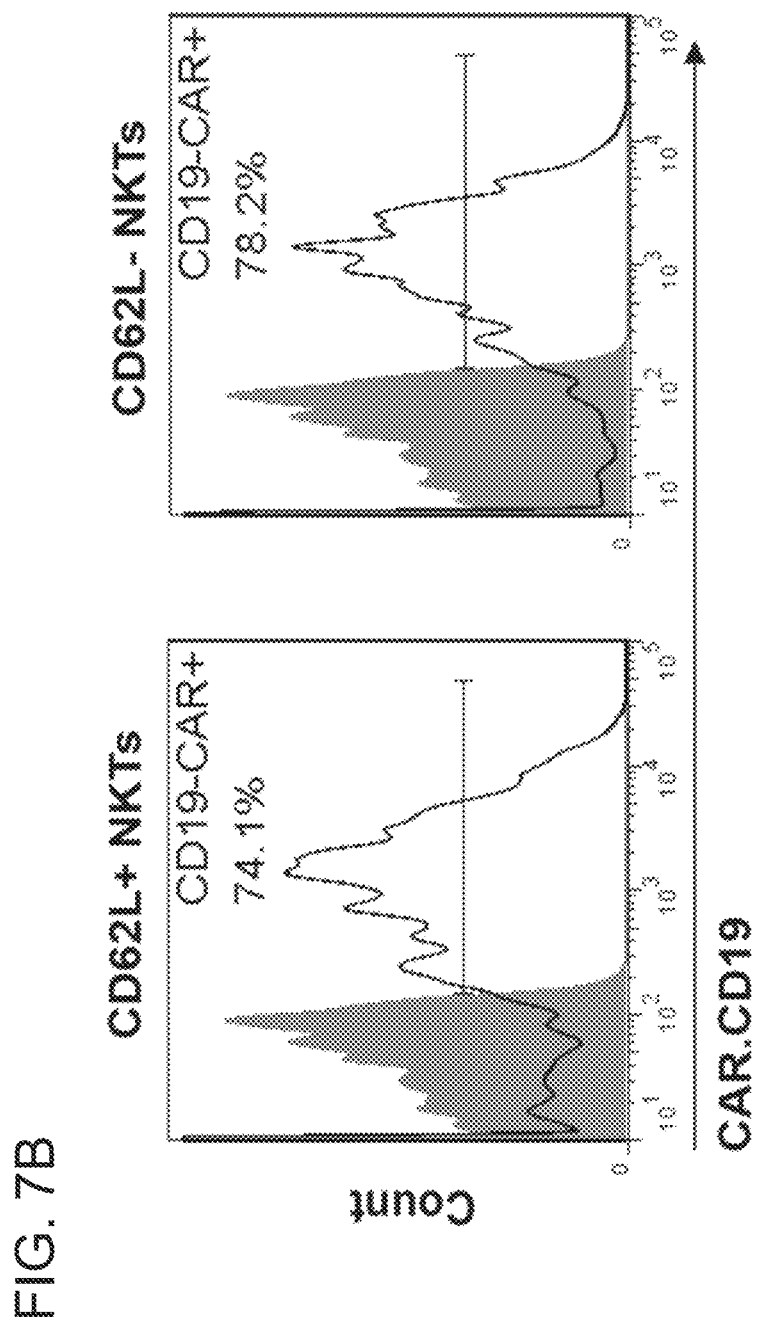

CD62L+ subset is responsible for NKTs in vivo persistence and therapeutic activity. To determine the role of the CD62L+ subset in the in vivo persistence of adoptively transferred NKTs, NKTs were transduced with firefly luciferase and they were magnetically sorted into CD62L+ and CD62L− subsets. The inventors then adoptively transferred the sorted cells to NSG mice. Longitudinal bioluminescent imaging demonstrated that the signal from CD62L− cells could be detected until day 2, whereas CD62L+ cells remained detectable up to day 10 (P<0.001, FIGS. 3A,B). Next, the in vivo therapeutic potential of CD62L+ and CD62L− NKT-cell subsets were compared in a model of CAR-redirected immunotherapy for lymphoma. NKTs were transduced with a CD19-specific CAR containing 4-1BB co-stimulatory endodomain (CAR.CD19, FIG. 7) followed by sorting into CD62L+ and CD62L− subsets. NOD/SCID/IL2Rγ(null) (NSG) mice were i.v. injected with luciferase-transduced CD19+ Daudi lymphoma cells and four days later were divided into two groups to receive CD62L+ or CD62L− CAR.CD19 NKT cells. Both CD62L+ and CD62L− CAR.CD19 NKTs prolonged the survival of treated animals compared with untreated control (P<0.001). Importantly, only CD62L+ CAR-NKTs induced sustained tumor regression with 7 of 9 treated animals alive, 5 of which were tumor-free, for at least three months. In contrast, all 10 mice treated with CD62L− CAR-NKTs succumbed to tumor progression (P<0.001, FIGS. 3C,D). Thus, CD62L+ NKTs have extended in vivo persistence and superior therapeutic potential compared with CD62L− NKTs.

Figure 8B:
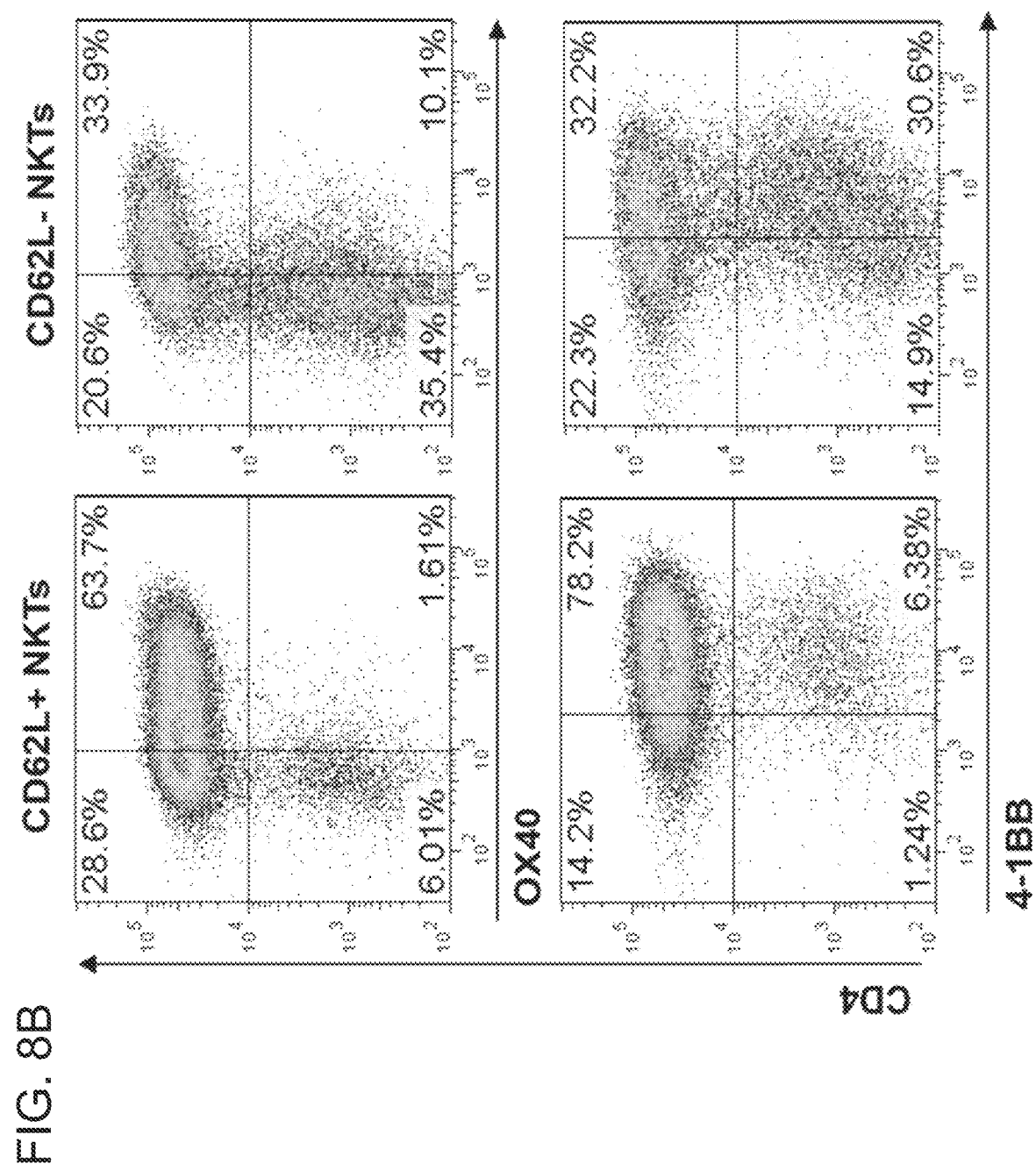

Co-stimulation maintains CD62L+ NKTs and prevents exhaustion. There is growing evidence that costimulation plays a role in the activation, survival, and expansion of NKTs (van den Heuvel et al., 2011). While resting NKTs express CD28, (FIG. 5C), they express little or no late co-stimulatory receptors such as 4-1BB and OX40 (FIG. 8A). However, stimulation of NKTs with αGalCer-pulsed autologous PBMC resulted in rapid induction of 4-1BB in all NKTs and OX40 in CD4+ NKTs (FIG. 8A). Because CD62L is transiently down-regulated within the first 24-48 h after TCR-stimulation (data not shown), the kinetics of 4-1BB and OX40 expression were analyzed in CD62L+ and CD62L− NKTs that were sorted prior to stimulation. It was found that 71.13%±18.66% and 51.98%±18.83% of CD62L+ and CD62L− NKTs up-regulated OX40 within 72 h after stimulation (P=0.0072, FIG. 4A). Similarly, stimulated CD62L+ NKTs expressed a higher level of 4-1BB compared to CD62L− NKTs (P=0.011, FIG. 4A). OX40 was preferentially up-regulated in CD4+ subset of either CD62L+ or CD62L− NKTs whereas 4-1BB was up-regulated in all NKTs (FIG. 8B).

Next, it was considered whether co-stimulation could counteract exhaustion of in vitro expanded NKTs. CD62L+ sorted NKTs were stimulated on plates coated with an anti-CD3 agonistic mAb OKT3 alone or in combination with mAbs for CD28, 4-1BB, or both. OX40 was not tested in these settings because the inventors could not obtain an anti-OX40 mAb with an agonistic activity. First, co-stimulation with either anti-CD28, anti-4-1BB mAb or both increased the number of NKTs generated in culture within 7 days compared with stimulation with anti-CD3 alone at 20 ng/ml (P<0.001, FIG. 4B). In the absence of co-stimulation, increasing the concentration of OKT3 from 20 ng/ml to 1 µg/ml did not affect the number of NKTs generated, while co-stimulation was effective in increasing NKT-cell number only when it was combined with the lower concentration of OKT3 (FIG. 9). Importantly, on day 7 after stimulation with OKT3 alone less than half the NKTs were positive for CD62L. The addition of anti-CD28, anti-4-1BB, or anti-CD28 with anti-4-1BB mAbs resulted in the retention of CD62L expression on 58%±7.1% (P=0.026), 73%±9.2% (P=0.0036), and 73%±6.1% (P=0.0002) of NKTs, respectively (FIG. 4C). Coordinately with the retention of CD62L expression, NKTs provided with costimulatory signals expressed significantly less PD-1 (P<0.05, FIG. 4D). Therefore, engagement of costimulatory receptors during antigenic stimulation supports CD62L expression in proliferating NKTs and prevents their exhaustion.

Significance of Certain Embodiments of the Disclosure

A critical gap in knowledge of human NKT-cell biology has slowed down the development of effective NKT cell-based cancer immunotherapy. NKT-cell numeric ex vivo expansion and subsequent in vivo persistence—essential requirements for effective NKT-cell based cell and gene therapy applications—depend on the CD62L+ subset of peripheral blood NKTs. Only CD62L+ NKTs survive and proliferate in response to repeated TCR-stimulation, while CD62L− cells undergo early exhaustion and cell death. Although continuous stimulation of NKTs is associated with the loss of CD62L expression, activation of co-stimulatory receptors during TCR-stimulation can counteract this process. Specifically, the inventors experimentally determined a unique combination of CD86, 4-1BBL and OX40L molecules and the levels of their co-expression on the surface of an aAPC that enable highly efficient clinical-scale NKT-cell expansion with maximal preservation of CD62L expression. In certain embodiments, CAR-NKTs generated using aAPC such as are encompassed by this disclosure exhibit extended in vivo persistence and superior therapeutic activity against in vivo models of lymphoma and neuroblastoma (as examples of cancer types).

The CD62L+ subset is responsible for the numeric expansion of NKTs upon antigenic stimulation ex vivo. The following findings support the above conclusion: i) the fraction of CD62L+ cells is dramatically increased after primary NKT-cell stimulation, ii) the majority of sorted CD62L− cells undergo apoptosis, whereas sorted CD62L+ cells proliferate in response to identical stimulation; iii) CD62L− NKTs exhibit signs of terminal differentiation (CD161 and CD56 expression) in freshly isolated PBMC and rapidly acquire an exhaustion phenotype upon in vitro stimulation as evidenced by marked up-regulation of PD-1 and TIM-3 expression and diminished ability to produce cytokines. When similar characteristics are observed in T-cell therapeutic products, they are associated with a subsequent lack of persistence or of objective responses after adoptive transfer to cancer patients (Gattinoni et al., 2005; Klebanoff et al., 2005).

Proliferating NKTs eventually down-regulate CD62L expression and acquire an exhaustion phenotype during in vitro culture. This observation likely reflects the ontogeny of human peripheral NKTs, as the frequency of CD62L+ NKTs is lower in adult peripheral blood compared with cord blood (Eger et al., 2006; Der Vliet et al., 2000). In one report, cord blood NKTs were found not to express CD62L (D'Andrea et al., 2000). The reason for the discrepancy between that report and others and with the present results is technical, in certain embodiments. M. Constantinides et al. identified a very rare naive-like population of CD1d-restricted T cells with a high level of CD62L in peripheral blood (Constantinides et al., 2011). However, these cells do not express the invariant Vα24 chain and have a lower level of PLZF expression compared with the classical NKTs. Both CD62L+ and CD62L− NKTs in this study expressed equally high levels of PLZF.

CD62L may represent a common marker of cells responsible for the long-term maintenance of peripheral NKT and T cells. P. Graef et al. demonstrated that CD62L+ central memory T cells possess stem cell properties; they could propagate themselves while giving rise to effector-memory and effector T cells (Graef et al., 2014). In the most recently published study, D. Sommermeyer et al. demonstrated that human CAR.CD19 expressing CD8 or CD4 T cells generated from naïve and central memory subsets were more effective against Raji lymphoma xenografts compared to those generated from effector-memory subsets (Sommermeyer et al., 2015). The authors also found that combining the most potent CD4+ and CD8+ CAR-expressing subsets produced synergistic antitumor activity in vivo. Activation of NKTs has been shown to lead to transactivation of NK and CD8 T cells in murine models and in human clinical trials (Dhodapkar et al., 2009; Vivier et al., 2012), so that the combination of CAR NKTs with other defined subsets of CAR-expressing lymphocytes may be a useful therapeutic strategy.

LEF1 and IL-7Rα were among the immune-related genes that were most overexpressed in CD62L+ compared to CD62L− NKTs. In a recent report, Carr et al. demonstrated a unique function of LEF1 in the expansion of murine Vα14-invariant (iNKT) cells during stage-2 of their thymic development via direct transcriptional activation of CD127 and c-myc gene expression (Carr et al., 2015). Consistent with the observation of the coordinated expression of LEF1 and GATA3 in human NKTs, these investigators also found that LEF1 up-regulates transcription factor GATA3, which is required for IL-4 production in iNKT2 cells as well as for dual production of IL-4 and INFγ in iNKT1 cells. The latter cells closely resemble human peripheral blood NKTs, in which it was found that CD62L+ cells preferentially express GATA3 and produce high levels of both cytokines. Taking the Carr et al. study with murine NKTs and the results with human NKTs, in specific embodiments LEF1 plays a critical role at early stages of NKT-cell development and controls their number and function. The high level of LEF1 expression in CD62L+ and its loss in CD62L− subsets of human NKTs is consistent with a model of linear progression from a less differentiated CD62L+ NKTs with a preserved proliferative potential and Th-0-like cytokine profile towards terminally differentiated CD62L− NKT cells with diminished ability to proliferate and produce cytokines.

There is growing evidence that co-stimulation plays a critical role in the development, activation, and functional responses of NKTs in murine models (van den Heuvel et al., 2011; Uldrich et al., 2005). However, little is known about the expression of co-stimulatory receptors in human NKTs. In this disclosure, the inventors focused on a set of co-stimulatory receptors that have pronounced pro-survival properties in human T cells: CD28, 4-1BB, and OX40 (Acuto et al., 2003; Kroczek et al., 2004; Redmond et al., 2009). First, it was confirmed that freshly isolated human NKTs express CD28 (34) and it was shown that they co-express CD27, thereby resembling the corresponding stage of memory T cell differentiation with preserved functional potential (Okada et al., 2008). The disclosure is the first to characterize the baseline and post-stimulation kinetics of 4-1BB and OX40 in human NKTs. Both receptors are undetectable in freshly isolated NKTs but are induced following TCR-stimulation. Similar to T cells (Croft, 2010), human NKTs preferentially up-regulated OX40 in the CD4+ subset. The majority of NKTs also up-regulated 4-1BB, which is preferentially up-regulated in the CD8+ subset of T cells (Lynch, 2008). Importantly, co-stimulation of individual co-stimulatory receptors could inhibit the loss of CD62L expression and rescue NKTs from exhaustion. There was an additive effect on the maintenance of CD62L+ NKTs when CD28 and 4-1BB were simultaneously activated.

Example 3

Examples of Methods and Materials

Cell lines and culture conditions. Daudi, Raji, DAOY, Ramos and 293T cells were purchased from ATCC. Daudi, Raji, and Ramos cells were cultured in RPMI, whereas DAOY and 293T cells were maintained in IMDM (Invitrogen). Both types of medium were supplemented with 10% FBS (Hyclone), 2 mM GlutaMAX-1 (Gibco-BRL).

NKT-cell isolation, transduction, expansion and sorting. To analyze the cord blood NKT cells discarded cord blood units obtained from MD Anderson Cancer Center Cord Blood Bank were used according to the protocols approved by the Institutional Review Boards at MD Anderson Cancer Center and Baylor College of Medicine. PBMC of healthy donors (at least 18 years old) were isolated by gradient centrifugation from buffy coats purchased from Gulf Coast Regional Blood Center. NKTs were purified by anti-iNKT microbeads (Miltenyi Biotec). The negative PBMC fraction was irradiated (40 Gy) and aliquoted. NKTs were stimulated with an aliquot of autologous PBMCs pulsed with 100 ng/mL αGalCer (Kyowa Hakko Kirin). Recombinant IL-2 (200 U/ml, National Cancer Institute Frederick) was added every other day in complete RPMI (HyClone RPMI 1640, 10% heat inactivated fetal bovine serum and 2 mM Glutamax). NKTs were expanded for 10 days and then re-stimulated with autologous PBMC (irradiated with 40 Gy) or Ramos cells as aAPC (irradiated with 100 Gy) when indicated. On day 3 after re-stimulation, 24 well, non-tissue culture plates were coated with retronectin (Takara Bio) and after washing inoculated with 1 ml of retroviral supernatant containing CAR.CD19 and spun for 60 min at 4600 G. The viral supernatant was then removed and stimulated NKTs were added to the wells in complete media and 200 U/ml rhIL-2. Cells were removed from the plate after 48 h, washed, re-suspended at the concentration $10^6$ cell/ml in complete RPMI with 200 U/ml IL-2 and plated for continued expansion. NKT-cell number was determined by Trypan Blue (Life technologies) counting. When indicated, NKTs or CAR-NKTs were labeled with CD62L-PE mAb (GREG-56, BD Biosciences) and anti-PE microbeads (Miltenyi) followed by magnetic sorting into CD62L+ and CD62L− subsets according to the manufacturer's instructions. The phenotype of the sorted cells was determined by FACS.

Retroviral constructs and retrovirus production. CAR.CD19 and CAR.GD2 constructs was made as previously described (Heczey et al., 2014; Pule et al., 2005) and contained a scFv from the CD19-specific antibody FMC-63 or the GD2-specific antibody 14G2a connected via a short spacer derived from the IgG1 hinge region to the transmembrane domain derived from CD8α, followed by signaling endodomain sequences of 4-1BB fused with chain. Retroviral supernatants were produced by transfection of 293T cells with a combination of chimeric antigen containing plasmids, RDF plasmid encoding the RD114 envelope and PegPam3 plasmid encoding the MoMLV gag-pol as previously described (Vera et al., 2006).

Proliferation and apoptosis assays. NKTs were labeled with CFSE (Invitrogen) and stimulated with αGalCerpulsed PBMC, or plates coated with 20 ng/ml anti-CD3 (OKT3) alone or in combination with 0.5 ug/ml anti-CD28 (CD28.2), and/or 1.5 ug/ml anti-4-1BB (h41BB-M127) (BD Biosciences). Cell proliferation was examined on day 3 and 6 by measuring CFSE dilution using flow cytometry. In addition, early and late stages of apoptosis were measured on day 3 by staining with Annexin-V and 7-AAD (BD Biosciences) followed by flow cytometry.

Multiplex cytokine quantification assay. NKTs were stimulated for 24 hours with either APCs or agonistic antibody-coated plates (clone 6B11, BD Biosciences). Supernatants were collected and analyzed with Human Cytokine/Chemokine Immunoassay kit (Millipore) using the Luminex® assay according to the manufacturer's instructions.

Flow cytometry. Immunophenotyping was performed using the following mAbs to: HLA-C EMR8-5, CD1d CD1d42, CD86 2331, 4-1BBL C65-485, OX40L ik-1, CD3 OKT, Vα24-Jα18 6B11, CD4 SK3, CD62L DREG-56, CD134 ACT35, CD137 4B4-1, PD-1 EH12.1, GATA3 L50-823 (BD Biosciences), LAG-3 Polyclonal, TIM-3 344823 (R&D System), and rabbit anti-LEF1 EP2030Y mAb (AB-CAM). BD or R&D-suggested fluorochrome and isotype-matching Abs were used as negative controls. The expression of CAR.CD19 on NKTs was determined using anti-Id (clone 136.20.1) CD19-CAR specific mAb (Torikai et al., 2013) and goat anti-mouse IgG (BD Biosciences). The analysis was performed on a LSR-II five-laser flow cytometer (BD Biosciences) using BD FACSDiva software v.6.0 and FlowJo 7.2.5 (Tree Star).

In vitro cytotoxicity assay. The cytotoxicity of parental and CAR.CD19 NKTs against DAOY or Raji cells was evaluated using 4-hour Luciferase Assay as previously described (Liu et al., 2013).

Gene expression analysis. Total RNA was collected using TRIzol reagent (Qiagen). Gene expression analysis was performed using Immunology Panel v.2 (NanoString) at BCM Genomic and RNA Profiling Core using nCounter Analysis System. Data were analyzed using nSolver 2.0 software (NanoString).

In vivo experiments. The colony of NSG mice was originally obtained from The Jackson Laboratory and maintained at BCM Animal Care facility. Tumor growth was initiated by i.v. injection of $2 \times 10^5$ luciferase-transduced Raji lymphoma cells. On day 3, mice were treated with $4-8 \times 10^6$ CAR-NKTs followed by i.p. injection of IL-2 (1000 U/mouse) every 3 days. Tumor growth was assessed twice per week by bioluminescent imaging (Small Animal Imaging Core facility, Texas Children's Hospital). For the in vivo persistence experiments, NKTs were co-transduced with CAR.CD19 and luciferase using retroviral constructs, i.v. injected to tumor-free or tumor-bearing mice, and monitored using bioluminescent imaging twice per week. Animal experiments were performed according to IACUC approved protocols.

Statistics. For in vitro and in vivo experiments, the inventors used 2-sided, paired Student's t test to evaluate continuous variable of 2 groups, and one-way ANOVA with post-test Bonferroni to evaluate continuous variables of more than 2 groups. Survival was analyzed by the Kaplan-Meier method and the Log-rank (Mantel-Cox) test to compare pairs of groups. Statistics were computed using GraphPad™ Prism 5.0 (GraphPad Software). Differences were considered significant when the p value was less than 0.05.

Study approval. The cord blood units were obtained from MD Anderson Cancer Center Cord Blood Bank according to the protocols approved by the Institutional Review Boards at MD Anderson Cancer Center (H-16320) and Baylor College of Medicine (H-20911). Written informed consent was received from all participating women prior to inclusion in the study under the protocol H-16320. Cord blood units not suitable for clinical use (usually due to low cell counts) were either discarded or used for research purposes under the protocol H-20911 at Baylor College of Medicine. Animal experiments were performed according to the protocol AN-5194 approved by the Institutional Animal Care and Use Committees of Baylor College of Medicine.

Example 4

Effect of IL-21 on NKT Cells

Figure 10:
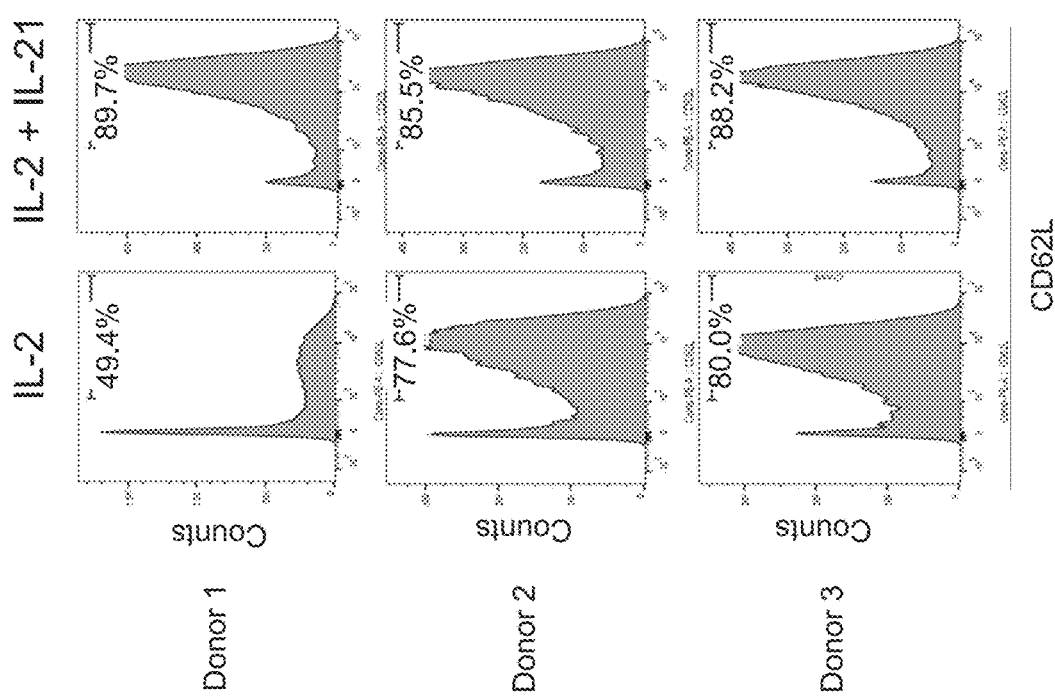
FIG. 10 shows that IL-21 increases frequency of CD62L+ NKT cells during primary expansion.
Figure 11:
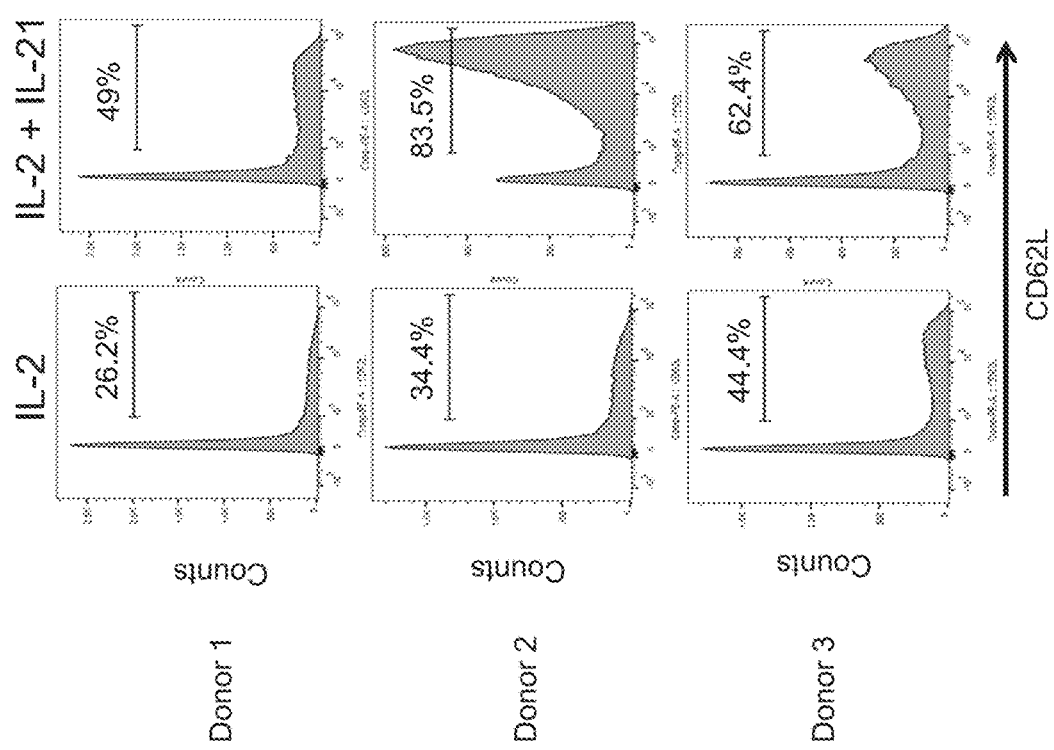
FIG. 11 demonstrates that IL-21 increases frequency of CD62L+ NKT cells during secondary expansion.
Figure 12:
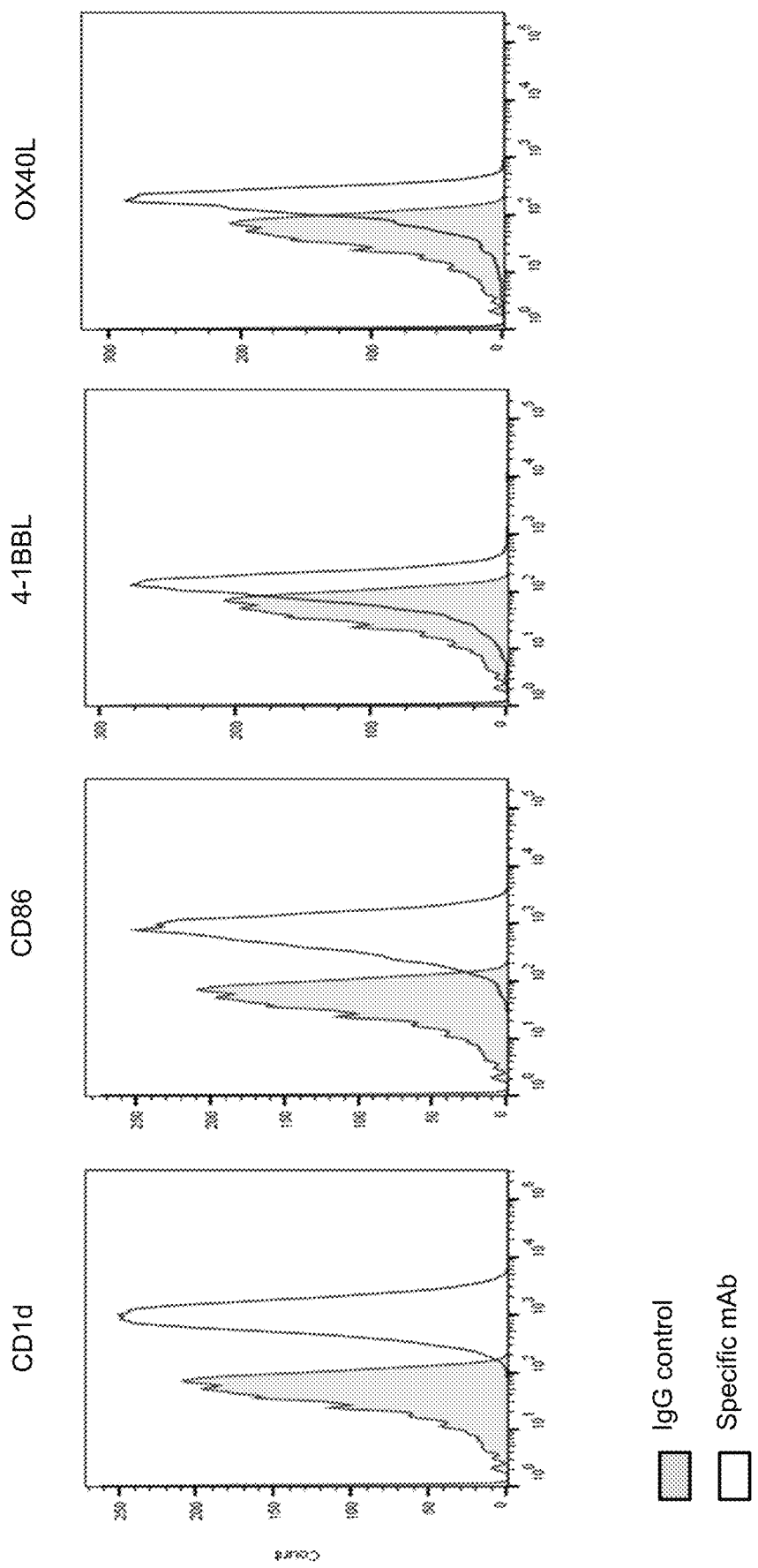
FIG. 12 shows expression of CD1d and co-stimulatory molecules on Ramos cells, as an example.
Figure 13:
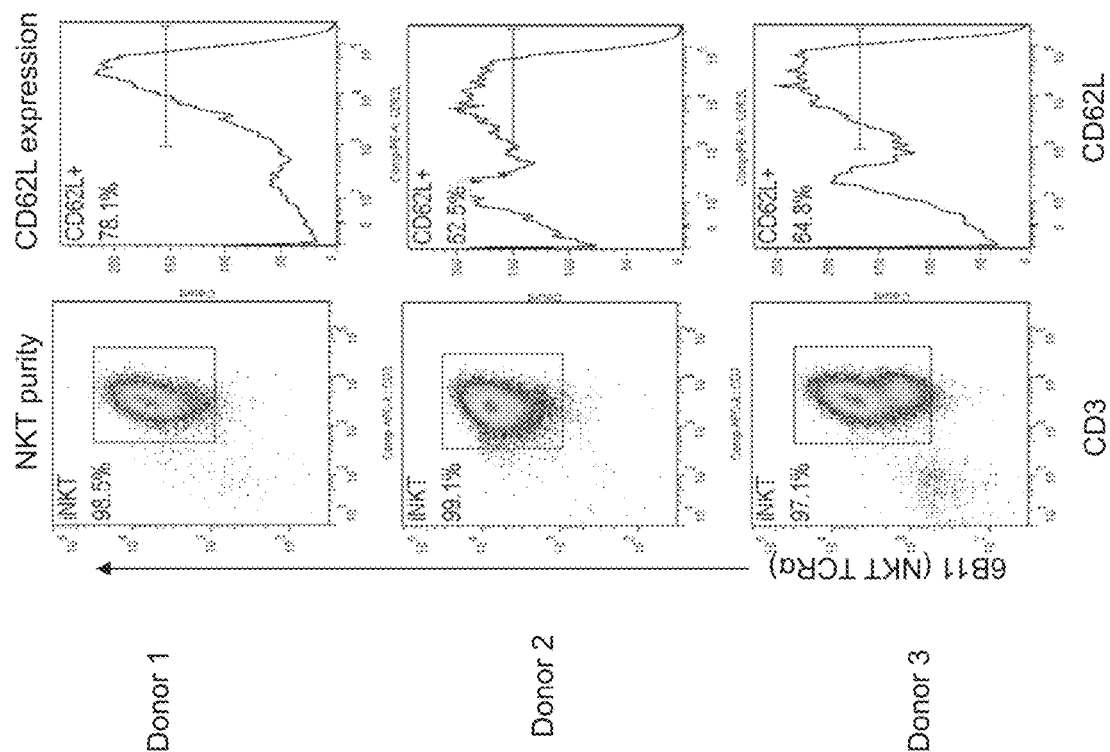
FIG. 13 demonstrates that Ramos cells can expand primary NKTs with high-level CD62L expression.

This example demonstrates that IL-21 has a beneficial effect on NKT cells upon exposure of the cells to IL-21. FIG. 10 shows that IL-21 increases the frequency of CD62L+ NKT cells during primary expansion. NKTs were isolated from three donors and stimulated with αGalCer-loaded PBMCs and IL-2 (100 U/ml) or IL-2 with IL-21 (long/ml) for 12 days. NKTs were collected and stained for CD62L followed by FACS analysis. FIG. 11 demonstrates that IL-21 increases the frequency of CD62L+ NKT cells during secondary expansion. Following primary expansion (FIG. 10), NKTs from three donors were re-stimulated with αGalCer-loaded PBMCs and IL-2 (100 U/ml) or IL-2 with IL-21 (10 ng/ml) for 12 days. NKTs were collected and stained for CD62L followed by FACS analysis. FIG. 12 shows expression of CD1d and co-stimulatory molecules on Ramos cells. Ramos B-cell lymphoma cell line was obtained from ATCC and analyzed by FACS for expression of CD1d, CD86, 4-1BBL, and OX40L using corresponding mAbs or IgG control. Ramos cells can expand primary NKTs with high-level CD62L expression (FIG. 13). NKTs were isolated from three donors and stimulated with aGalCer-loaded Ramos cells ($2 \times 10^6$/well) in IL-2 containing media for 10 days. NKTs were collected, counted and stained for CD3, 6B11 and CD62L. Finally, in FIG. 14 it is shown that Ramos cells expand NKTs upon secondary stimulation with significant retention of CD62L expression. Following primary expansion with PBMC (as in FIG. 10), NKTs (1×10-/well) were re-stimulated with aGalCer-loaded Ramos cells ($2 \times 10^6$/well) in IL-2 containing media for 10 days. NKTs were collected, counted and stained for CD3, 6B11 and CD62L.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Acuto O, Michel F. CD28-mediated co-stimulation: a quantitative support for TCR signalling. *Nat. Rev. Immunol.* 2003; 3(12):939-951.

Ara T, et al. Critical role of STAT3 in IL-6-mediated drug resistance in human neuroblastoma. *Cancer Res.* 2013; 73(13):3 S52-3 S64.

Baev D V, et al. Distinct homeostatic requirements of CD4+ and CD4− subsets of Valpha24-invariant natural killer T cells in humans. *Blood* 2004; 104(13): 4150-4156.

Barakonyi A, et al. Cutting edge: engagement of CD160 by its HLA-C physiological ligand triggers a unique cytokine profile secretion in the cytotoxic peripheral blood NK cell subset. *J. Immunol.* 2004; 173(9):5349-5354.

Bendelac A, Lantz O, Quimby M E, Yewdell J W, Bennink J R, Brutkiewicz R R. CD1 recognition by mouse NK1+ T lymphocytes. *Science* 1995; 268(5212):863-865.

Brentjens R J, et al. CD19-targeted T cells rapidly induce molecular remissions in adults with chemotherapy-refractory acute lymphoblastic leukemia. *Sci. Transi. Med.* 013; 5(177):177ra13S.

Cariani E, et al. Immunological and molecular correlates of disease recurrence after liver resection for hepatocellular carcinoma. *PLoS. One.* 2012; 7(3):e32493.

Carr T, Krishnamoorthy V, Yu S, Xue H H, Kee B L, Verykokakis M. The transcription factor lymphoid enhancer factor 1 controls invariant natural killer T cell expansion and Th2-type effector differentiation. *J. Exp. Med.* 2015; 212(5): 793-807.

Casorati G, de L C, Dellabona P. Invariant natural killer T cells reconstitution and the control of leukemia relapse in pediatric haploidentical hematopoietic stem cell transplantation. *Oncoimmunology.* 2012; 1(3):355-357.

Chan W K, et al. Chimeric antigen receptor-redirected CD45RA-negative T cells have potent antileukemia and pathogen memory response without graft-versus-host activity. *Leukemia* 2015; 29(2):387-395.

Cohen N R, et al. Shared and distinct transcriptional programs underlie the hybrid nature of iNKT cells. *Nat. Immunol.* 2013; 14(1):90-99.

Constantinides M G, Bendelac A. Transcriptional regulation of the NKT cell lineage. *Curr. Opin. Immunol.* 2013; 25(2):161-167.

Constantinides M G, Picard D, Savage A K, Bendelac A. A naive-like population of human CD1d-restricted T cells expressing intermediate levels of promyelocytic leukemia zinc finger. *J. Immunol.* 2011; 187(1):309-315.

Croft M. Control of immunity by the TNFR-related molecule OX40 (CD134). *Annu. Rev. Immunol.* 2010; 28:57-78.

D'Andrea A, et al. Neonatal invariant Valpha24+ NKT lymphocytes are activated memory cells. *Eur. J. Immunol.* 2000; 30(6):1544-1550.

de L C, et al. Invariant NKT cell reconstitution in pediatric leukemia patients given HLA-haploidentical stem cell transplantation defines distinct CD4+ and CD4− subset dynamics and correlates with remission state. *J./mmuno/.* 2011; 186 (7):4490-4499.

DelaRosa O, et al. Valpha24+ NKT cells are decreased in elderly humans. *Exp. Gerontol.* 2002; 37(2-3):213-217.

Der Vliet H. J., et al. Human natural killer T cells acquire a memory-activated phenotype before birth. *Blood* 2000; 95(7):2440-2442.

Dhodapkar M V, et al. A Reversible Defect in Natural Killer T Cell Function Characterizes the Progression of Premalignant to Malignant Multiple Myeloma. *J. Exp. Med.* 2003; 197(12): 1667-76.

Dhodapkar M V. Harnessing human CD1d restricted T cells for tumor immunity: progress and challenges. *Front Biosci.* 2009; 14:796-807.

Dotti G, Gottschalk S, Savoldo 8, Brenner M K. Design and development of therapies using chimeric antigen receptor-expressing T cells. *Immuno/.Rev.* 2014; 257(1):107-126.

Eger K A, Sundrud M S, Motsinger A A, Tseng M, Van K L, Unutmaz D. Human natural killer T cells are heterogeneous in their capacity to reprogram their effector functions. *PLoS. One.* 2006; 1:e50.

ExleyMA, Nakayama T. NKT-cell-based immunotherapies in clinical trials. *Clin. Immunol.* 2011; 140(2):117-118.

Exley M A, et al. Selective activation, expansion, and monitoring of human iNKT cells with a monoclonal antibody specific for the TCR alpha-chain CDR3 loop. *Eur. J. Immunol.* 2008; 38(6):1756-1766.

Gapin L, Matsuda J L, Surh C D, Kronenberg M. NKT cells derive from double-positive thymocytes that are positively selected by CD1d. *Nat. Immunol.* 2001; 2(10):971-978.

Gattinoni L, et al. Acquisition of full effector function in vitro paradoxically impairs the in vivo antitumor efficacy of adoptively transferred CDS+ T cells. J. Ciin. Invest 2005; 115(6):1616-1626.

Graef P, et al. Serial transfer of single-cell-derived immunocompetence reveals sternness of CDS(+)central memory T cells. *Immunity.* 2014; 41(1):116-126.

Grupp S A, et al. Chimeric antigen receptor-modified T cells for acute lymphoid leukemia. *N. Engi. J. Med.* 2013; 365(16):1509-1515.

Heczey A, et al. Invariant NKT cells with chimeric antigen receptor provide a novel platform for safe and effective cancer immunotherapy. *Blood* 2014; 124(18):2824-2833.

Jena B, et al. Chimeric antigen receptor (CAR)-specific monoclonal antibody to detect CD19-specific T cells in clinical trials. *PLoS.One.* 2013; 8(3):e57838.

Kalas M, June C H. Adoptive T cell transfer for cancer immunotherapy in the era of synthetic biology. *Immunity* 2013; 39(1):49-60.

Kim E Y, Lynch L, Brennan P J, Cohen N R, Brenner M B. The transcriptional programs of iNKT cells. *Semin. Immunol.* 2015; 27(1):26-32.

King M A, et al. Human peripheral blood leucocyte non-obese diabetic-severe combined immunodeficiency interleukin-2 receptor gamma chain gene mouse model of xenogeneic graft-versus-host-like disease and the role of host major histocompatibility complex. *Clin. Exp. Immunol.* 2009; 157(1):104-118.

Klebanoff C A, et al. Central memory self/tumor-reactive CDS+ T cells confer superior antitumor immunity compared with effector memory T cells. *Proc. Natl. Acad. Sci. U.S.A* 2005; 102(27): 9571-9576.

Kochenderfer J N, et al. B-cell depletion and remissions of malignancy along with cytokine-associated toxicity in a clinical trial of anti-CD19 chimeric-antigen-receptor-transduced T cells. *Blood* 2012; 119(12):2709-2720.

Kroczek R A, Mages H W, Hutloff A. Emerging paradigms off-cell co-stimulation. *Curr. Opin. Immunol.* 2004; 16(3):321-327.

Kronenberg M, Gapin L. The unconventional lifestyle of NKT cells. *Nat. Rev. Immunol.* 2002; 2(8):557-568.

Lantz O, Bendelac A. An invariant T cell receptor alpha chain is used by a unique subset of major histocompatibility complex class !—specific CD4+ and CD4-8− T cells in mice and humans. *J. Exp. Med.* 1994; 180(3): 1097-1106.

Lee P T, Benlagha K, Teyton L, Bendelac A. Distinct functional lineages of human V(alpha)24 natural killer T cells. *J. Exp. Med.* 2002; 195(5):637-641.

Liu D, et al. Medulloblastoma expresses CD1d and can be targeted for immunotherapy with NKT cells. *Clin. Immunol.* 2013; 149(1):55-64.

Loza M J, Metelitsa L S, Perussia B. NKT and T cells: coordinate regulation of NK-like phenotype and cytokine production. *Eur. J. Immunol.* 2002; 32(12):3453-3462.

Lynch D H. The promise of 4-1BB (CD137)-mediated immunomodulation and the immunotherapy of cancer. *Immunoi. Rev.* 2008; 222:277-286.

Matsuda J L, et al. Homeostasis of V alpha 14i NKT cells. *Nat. Immunol.* 2002; 3(10):966-974.

Maus M V, et al. Ex vivo expansion of polyclonal and antigen-specific cytotoxic T lymphocytes by artificial APCs expressing ligands for the T-cell receptor, CD28 and 4-188. *Nat. Biotechnol.* 2002; 20(2):143-148.

McEwen-Smith R M, Salio M, Cerundolo V. The regulatory role of invariant NKT cells in tumor immunity. *Cancer Immunoi. Res.* 2015; 3(5):425-435.

Metelitsa L S, et al. Human NKT cells mediate antitumor cytotoxicity directly by recognizing target cell CD1d with bound ligand or indirectly by producing IL-2 to activate NK cells. *J. Immunol.* 2001; 167(6):3114-3122.

Metelitsa L S. Anti-tumor potential of type I NKT cells against CD1d-positive and CD1d-negative tumors in humans. *Clin. Immuno/.* 2011; 140(2):119-129.

Metelitsa L S, et al. Natural killer T cells infiltrate neuroblastomas expressing the chemokine CCL2. *J. Exp. Med.* 2004; 199(9):1213-1221.

Moiling J W, et al. Low levels of circulating invariant natural killer T cells predict poor clinical outcome in patients with head and neck squamous cell carcinoma. *J. Clin. Onco/.* 2007; 25(7):862-868.

Morris E S, et al. NKT cell-dependent leukemia eradication following stem cell mobilization with potent G-CSF analogs. *J. Clin. Invest* 2005; 115(11):3093-3103.

Motohashi S, Okamoto Y, Yoshino I, Nakayama T. Anti-tumor immune responses induced by iNKT cell-based immunotherapy for lung cancer and head and neck cancer. *Clin. Immunol.* 2011; 140(2):167-176.

Okada R, Kondo T, Matsuki F, Takata H, Takiguchi M. Phenotypic classification of human CD4+ T cell subsets and their differentiation. *Int. Immunol.* 2008; 20(9):1189-1199.

Pegram H J, Smith E L, Rafiq S, Brentjens R J. CAR therapy for hematological cancers: can success seen in the treatment of 8-cell acute lymphoblastic leukemia be applied to other hematological malignancies? *Immunotherapy.* 2015; 7(5): 545-561.

Porcelli S, Yockey C E, Brenner M B, Balk S P. Analysis of T cell antigen receptor (TCR) expression by human peripheral blood CD4-8-alpha/beta T cells demonstrates preferential use of several V beta genes and an invariant TCR alpha chain. *J. Exp. Med.* 1993; 178(1):1-16.

Pillai A B, George T I, Dutt S, Teo P, Strober S. Host NKT cells can prevent graft-versus-host disease and permit graft antitumor activity after bone marrow transplantation. *J./Immunol.* 2007; 178(10):6242-6251.

Porter D L, Levine B L, Kalos M, Bagg A, June C H. Chimeric antigen receptor-modified T cells in chronic lymphoid leukemia. *N. Engi. J. Med.* 2011; 365(S):725-733.

Pule M A, Straathof K C, Dotti G, Heslop H E, Rooney C M, Brenne M K. A chimeric T cell antigen receptor that augments cytokine release and supports clonal expansion of primary human T cells. *Mol. Ther.* 2005; 12(5):933-941.

Ramos C A, Heslop H E, Brenner M K. CAR-T Cell Therapy for Lymphoma. *Annu. Rev. Med.* 2015.

Redmond W L, Ruby C E, Weinberg A D. The role of OX40-mediated co-stimulation in T-cell activation and survival. *Crit Rev. Immunol.* 2009; 29(3):187-201.

Sallusto F, Geginat J, Lanzavecchia A. Central memory and effector memory T cell subsets: function, generation, and maintenance. *Annu. Rev. Immunol.* 2004; 22:745-763.

Savage A K, et al. The transcription factor PLZF directs the effector program of the NKT cell lineage. *Immunity.* 2008; 29(3):391-403.

Savoldo B, et al. CD2S costimulation improves expansion and persistence of chimeric antigen receptor-modified T cells in lymphoma patients. *J.C/in. Invest* 2011; 121(5): 1S22-1S26.

Sommermeyer D, et al. Chimeric antigen receptor-modified T cells derived from defined COB and CD4 subsets confer superior antitumor reactivity in vivo. *Leukemia* 2015.

Suhoski M M, et al. Engineering artificial antigen-presenting cells to express a diverse array of co-stimulatory molecules. *Mol. Ther.* 2007; 15(5):981-988.

Tachibana T, et al. Increased intratumor Valpha24-positive natural killer T cells: a prognostic factor for primary colorectal carcinomas. *Clin. Cancer Res.* 2005; 11(20): 7322-7327.

Tahir S M, et al. Loss of IFN-gamma production by invariant NK T cells in advanced cancer. *J. Immunol.* 2001; 167(7):4046-4050.

Taniguchi M, Harada M, Dashtsoodol N, Kojo $.Discovery of NKT cells and development of NKT cell-targeted anti-tumor immunotherapy. *Proc. Jpn. Acad. Ser. B Phys. Bio/.Sci.* 2015; 91(7):292-304.

Thomas A K, Maus M V, Shalaby W S, Jun. C H, Riley J L. A cell-based artificial antigen-presenting cell coated with anti-CD3 and CD28 antibodies enables rapid expansion and long-term growth of CD4 T lymphocytes. *Clin. Immunol.* 2002; 105(3):259-272.

Torikai H, et al. Toward eliminating HLA class I expression to generate universal cells from allogeneic donors. *Blood.* 2013; 122(8):1341-1349.

Uldrich A P, et al. NKT cell stimulation with glycolipid antigen in vivo: costimulation-dependent expansion, Bim-dependent contraction, and hyporesponsiveness to further antigenic challenge. *J. Immunol.* 2005; 175(5):3092-3101.

van den Heuvel M J, Garg N, Van K L, Haeryfar S M. NKT cell costimulation: experimental progress and therapeutic promise. *Trends Mo/Med.* 2011; 17(2):65-77.

Vera J, et al. T lymphocytes redirected against the kappa light chain of human immunoglobulin efficiently kill mature B lymphocyte-derived malignant cells. *Blood* 2006; 108 (12):3890-3897.

Vivier E, Ugolini S, Blaise D, Chabannon C, Brossay L. Targeting natural killer cells and natural killer Tcells in cancer. *Nat. Rev. Immunol.* 2012; 12(4):239-252.

Wang X, et al. Phenotypic and functional attributes of lentivirus-modified CD19-specific human COB+central memory T cells manufactured at clinical scale. *J. Immunother.* 2012; 35(9):689-701.

Xu Y, et al. Closely related T-memory stem cells correlate with in vivo expansion of CAR.CD19-T cells and are preserved by IL-7 and IL-15. *Blood* 2014; 123(24):3750-3759.

Yamasaki K, et al. Induction of NKT cell-specific immune responses in cancer tissues after NKT cell-targeted adoptive immunotherapy. *Clin. Immunol.* 2011; 138(3):255-265

What is claimed is:

1. A method of preparing human Type I natural killer T (NKT) cells for use in immunotherapy, comprising the steps of: isolating human NKT cells from human peripheral blood mononuclear cells (PBMCs), to generate an NKT-selected cell fraction and an NKT-depleted cell fraction, and expanding said NKT-selected cell fraction by culturing in the presence of at least:
   (1) IL-21 and second cytokine selected from the group consisting of IL-2, IL-7, IL-15, IL-12, TNF-alpha; and
   (2) irradiated NKT-depleted PBMCs loaded with alpha-Galactosylceramide (aGalCer) or irradiated artificial antigen-presenting cells (aAPCs) expressing CD1-d loaded with aGalCer;
   wherein the majority of human Type I NKT cells in said expanded NKT-selected cell fraction are CD62L positive human Type I NKT cells.

2. The method according to claim 1, wherein the NKT-selected cell fraction is expanded in media comprising IL-2.

3. The method according to claim 1, wherein the NKT-selected cell fraction is expanded in the presence of irradiated aAPCs expressing CD1-d loaded with aGalCer.

4. The method according to claim 1, wherein a subset of said CD62L positive human Type I NKT cells in said expanded NKT-selected cell fraction are 4-1BB positive.

5. The method according to claim 1, wherein the NKT-selected cell fraction is expanded by culturing in media comprising IL-2, IL-21, and aGalCer.

6. The method according to claim 2, wherein the irradiated NKT-depleted PBMCs are autologous to said NKT-selected cell fraction.

7. The method according to claim 1, wherein the NKT cells are isolated using anti-NKT microbeads.

8. The method according to claim 1, wherein the irradiated NKT-depleted PBMCs are not autologous to said NKT-selected cell fraction.

9. The method according to claim 3, wherein the irradiated aAPCs expressing CD1-d are Ramos cells.

10. The method according to claim 1, wherein the NKT-selected cell fraction is modified to express at least one chimeric antigen receptor (CAR).

11. The method according to claim 1, wherein said majority of said human Type I NKT cells in said expanded NKT-selected cell fraction are CD62L positive human Type I NKT on day 12 of culture.

12. The method according to claim 1, wherein said cells in said NKT-selected cell fraction are uncultured human NKT cells.

13. The method according to claim 1, wherein the NKT-selected cell fraction is cultured in media containing fetal bovine serum.

14. A method of preparing human CD62L-positive enriched human Type I natural killer T (NKT) cells for use in immunotherapy, comprising the steps of:
   isolating human NKT cells from uncultured human peripheral blood mononuclear cells (PBMCs), to generate an NKT-selected cell fraction and an NKT-depleted cell fraction, and expanding said NKT-selected cell fraction by culturing in the presence of at least:
   (1) IL-21 and second cytokine selected from the group consisting of IL-2, IL-7, IL-15, IL-12, TNF-alpha; and
   (2) irradiated NKT-depleted PBMCs loaded with alpha-Galactosylceramide (aGalCer) or irradiated artificial antigen-presenting cells (aAPCs) expressing CD1-d loaded with aGalCer;
   wherein the majority of human Type I NKT cells in said expanded NKT-selected cell fraction are CD62L positive human Type I NKT cells.

15. The method according to claim 14, wherein the NKT cells are isolated using anti-NKT microbeads.

16. The method according to claim 14, wherein the NKT-selected cell fraction is expanded by culturing in media comprising IL-2 and IL-21.

17. The method according to claim 14, wherein the irradiated aAPCs are Ramos cells.

18. The method according to claim 14, wherein the NKT-selected cell fraction is modified to express at least one chimeric antigen receptor (CAR).

19. The method according to claim 14, wherein the NKT-selected cell fraction is expanded by culturing in media comprising IL-2, IL-21, and aGalCer.

20. The method according to claim 14, wherein the irradiated NKT-depleted PBMCs are autologous with respect to an individual that receives the immunotherapy.

21. The method according to claim 14, wherein a subset of said CD62L positive human Type I NKT cells in said expanded NKT-selected cell fraction are 4-1BB positive said human Type I NKT cells.

22. The method according to claim 14, wherein the NKT-selected cell fraction is cultured in media containing fetal bovine serum.

23. A method of preparing human Type I natural killer T (NKT) cells for use in immunotherapy, comprising the steps of: isolating human NKT cells from uncultured human peripheral blood mononuclear cells (PBMCs), to generate an NKT-selected cell fraction and an NKT-depleted cell fraction, and expanding the NKT-selected cell fraction by culturing in the presence of at least:
   (1) IL-21 and second cytokine selected from the group consisting of IL-2, IL-7, IL-15, IL-12, TNF-alpha; and
   (2) irradiated NKT-depleted PBMCs loaded with alpha-Galactosylceramide (aGalCer) or irradiated artificial antigen-presenting cells (aAPCs) expressing CD1-d loaded with aGalCer;
   wherein said expanded NKT-selected cell fraction comprises a subset of 4-1BB positive human Type I NKT cells.

24. The method according to claim 23, wherein the NKT cells are isolated using anti-NKT microbeads.

25. The method according to claim 23, wherein the majority of human Type I NKT cells in said expanded NKT-selected cell fraction are CD62L positive human Type I NKT cells on day 12 of culture.

26. The method according to claim 23, wherein said second cytokine is IL-2.

27. The method according to claim 23, wherein the irradiated aAPCs are Ramos cells.

28. The method according to claim 23, wherein the NKT-selected cell fraction is modified to express at least one chimeric antigen receptor (CAR).

29. The method according to claim 23, wherein said irradiated NKT-depleted PBMCs are not autologous to said NKT-selected cell fraction.

30. The method according to claim 23, wherein the irradiated NKT-depleted PBMCs are autologous with respect to an individual that receives the immunotherapy.

31. The method according to claim 23, wherein the NKT-selected cell fraction is cultured in media containing fetal bovine serum.

32. The method according to claim 23, wherein the NKT-selected cell fraction is expanded by culturing in media comprising IL-2, IL-21, and aGalCer.

33. The method according to claim 1, wherein said CD62L positive human Type I NKT cells are modified to express at least one chimeric antigen receptor (CAR).

34. The method according to claim 14, wherein said CD62L positive human Type I NKT cells are modified to express at least one chimeric antigen receptor (CAR).

35. The method according to claim 23, wherein said subset of 4-1BB positive human Type I NKT cells is modified to express at least one chimeric antigen receptor (CAR).

* * * * *